(12) United States Patent
Ben-Moshe et al.

(10) Patent No.: US 10,550,196 B2
(45) Date of Patent: Feb. 4, 2020

(54) HUMANIZED ANTIBODIES AGAINST CEACAM1

(71) Applicant: CCAM BIOTHERAPEUTICS LTD., Hod HaSharon (IL)

(72) Inventors: Tehila Ben-Moshe, Koranit (IL); Yair Sapir, Manof (IL); Ilana Mandel, Carmiel (IL); Gal Markel, Ramat Gan (IL); Jacob Schachter, Givataim (IL); Rona Ortenberg, Yokne'am Illit (IL); Francis Joseph Carr, Balmedie (GB); Robert George E. Holgate, Royston (GB); Timothy David Jones, Babraham (GB)

(73) Assignee: Famewave Ltd., Tel Aviv (IL)

( * ) Notice: Subject to any disclaimer, the term of this patent is extended or adjusted under 35 U.S.C. 154(b) by 108 days.

(21) Appl. No.: 15/306,664

(22) PCT Filed: Apr. 27, 2015

(86) PCT No.: PCT/IL2015/050433
§ 371 (c)(1),
(2) Date: Oct. 25, 2016

(87) PCT Pub. No.: WO2015/166484
PCT Pub. Date: Nov. 5, 2015

(65) Prior Publication Data
US 2017/0044270 A1    Feb. 16, 2017

Related U.S. Application Data

(60) Provisional application No. 61/984,786, filed on Apr. 27, 2014, provisional application No. 62/099,155, filed on Jan. 1, 2015.

(51) Int. Cl.
| | |
|---|---|
| *C07K 16/42* | (2006.01) |
| *C07K 16/30* | (2006.01) |
| *A61K 35/17* | (2015.01) |
| *A61K 39/395* | (2006.01) |
| *A61K 45/06* | (2006.01) |
| *G01N 33/68* | (2006.01) |
| *A61K 39/00* | (2006.01) |
| *G01N 33/574* | (2006.01) |
| *C07K 16/28* | (2006.01) |

(52) U.S. Cl.
CPC .......... *C07K 16/3007* (2013.01); *A61K 35/17* (2013.01); *A61K 39/39558* (2013.01); *A61K 45/06* (2013.01); *C07K 16/2827* (2013.01); *G01N 33/57492* (2013.01); *A61K 2039/505* (2013.01); *A61K 2039/507* (2013.01); *A61K 2039/545* (2013.01); *C07K 2317/24* (2013.01); *C07K 2317/56* (2013.01); *C07K 2317/565* (2013.01); *C07K 2317/567* (2013.01); *C07K 2317/73* (2013.01); *C07K 2317/92* (2013.01); *G01N 2333/70503* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs |
| 3,839,153 A | 10/1974 | Schuurs |
| 3,850,578 A | 11/1974 | McConnell |
| 3,850,752 A | 11/1974 | Schuurs |
| 3,853,987 A | 12/1974 | Dreyer |
| 3,867,517 A | 2/1975 | Ling |
| 3,879,262 A | 4/1975 | Schuurs |
| 3,901,654 A | 8/1975 | Gross |
| 3,935,074 A | 1/1976 | Rubenstein |
| 3,984,533 A | 10/1976 | Uzgiris |
| 3,996,345 A | 12/1976 | Ullman |
| 4,034,074 A | 7/1977 | Miles |
| 4,036,945 A | 7/1977 | Haber |
| 4,098,876 A | 7/1978 | Piasio |
| 4,331,647 A | 5/1982 | Goldenberg |
| 4,348,376 A | 9/1982 | Goldenberg |
| 4,666,828 A | 5/1987 | Gusella |
| 4,683,202 A | 7/1987 | Mullis |
| 4,801,531 A | 1/1989 | Frossard |
| 4,816,567 A | 3/1989 | Cabilly |
| 4,879,219 A | 11/1989 | Wands |
| 4,946,778 A | 8/1990 | Ladner |
| 5,011,771 A | 4/1991 | Bellet |

(Continued)

FOREIGN PATENT DOCUMENTS

| | | |
|---|---|---|
| EP | 0404097 | 12/1990 |
| EP | 1133311 | 10/2006 |

(Continued)

OTHER PUBLICATIONS

Almagro & Fransson, Frontiers in Bioscience 2008; 13:1619-33.*
De Genst et al., Developmental and Comparative Immunology, 2006, 30:187-98.*
Barthelemy et al. (Journal of Biological Chemistry, 2008, 283:3639-3654).*
Choi et al., 2011, Molecular BioSystems, 2011, 7:3327-334.*
Griffiths et al. (The EMBO Journal, 1993, 12:725-734).*
Klimka et al., British Journal of Cancer, 2000, 83:252-260.*
Beiboer et al. (Journal of Molecular Biology, 2000, 296:833-849).*
Ward et al. (Nature, 1989, 341:544-546).*

(Continued)

*Primary Examiner* — Julie Wu
(74) *Attorney, Agent, or Firm* — Rothwell, Figg, Ernst & Manbeck, P.C.

(57) ABSTRACT

Humanized antibodies, capable of specific binding to human CEACAM1 molecules containing human-to-murine back-mutations in non-CDR variable regions, and their encoding polynucleotide sequences are provided. Pharmaceutical compositions comprising these antibodies as well as methods of their use in treating and diagnosing cancer and other conditions are also provided.

16 Claims, 16 Drawing Sheets
Specification includes a Sequence Listing.

(56) References Cited

U.S. PATENT DOCUMENTS

| | | | |
|---|---|---|---|
| 5,091,513 A | 2/1992 | Huston | |
| 5,096,815 A | 3/1992 | Ladner | |
| 5,192,659 A | 3/1993 | Simons | |
| 5,225,539 A | 7/1993 | Winter | |
| 5,272,057 A | 12/1993 | Smulson | |
| 5,281,521 A | 1/1994 | Trojanowski | |
| 5,530,101 A | 6/1996 | Queen | |
| 5,545,806 A | 8/1996 | Lonberg | |
| 5,545,807 A | 8/1996 | Surani | |
| 5,569,825 A | 10/1996 | Lonberg | |
| 5,585,089 A | 12/1996 | Queen | |
| 5,625,126 A | 4/1997 | Lonberg | |
| 5,633,425 A | 5/1997 | Lonberg | |
| 5,641,870 A | 6/1997 | Rinderknecht | |
| 5,661,016 A | 8/1997 | Lonberg | |
| 5,693,761 A | 12/1997 | Queen | |
| 5,693,762 A | 12/1997 | Queen | |
| 5,750,373 A | 5/1998 | Garrard | |
| 5,910,573 A | 6/1999 | Plueckthun | |
| 6,013,772 A | 1/2000 | Barnett | |
| 7,579,392 B2 | 8/2009 | Gan | |
| 7,820,410 B2 | 10/2010 | Benes | |
| 8,062,636 B2 | 11/2011 | Goldenberg | |
| 8,598,322 B2 | 12/2013 | Markel | |
| 2002/0028203 A1 | 3/2002 | Blumberg | |
| 2003/0022292 A1 | 1/2003 | Gray-Owen | |
| 2003/0190600 A1 | 10/2003 | Holmes | |
| 2004/0047858 A1 | 3/2004 | Blumberg | |
| 2004/0214184 A1 | 10/2004 | Skubitz | |
| 2005/0107324 A1 | 5/2005 | Bennett | |
| 2005/0169922 A1 | 8/2005 | Blumberg | |
| 2006/0039913 A1 | 2/2006 | Das | |
| 2006/0058257 A1 | 3/2006 | Wagener | |
| 2007/0071758 A1 | 3/2007 | Markel | |
| 2007/0110668 A1 | 5/2007 | Markel | |
| 2008/0102071 A1 | 5/2008 | Blumberg | |
| 2008/0108140 A1 | 5/2008 | Markel | |
| 2009/0081239 A1* | 3/2009 | Staunton | C07K 16/36 424/172.1 |
| 2009/0136528 A1 | 5/2009 | Singh | |
| 2009/0226444 A1 | 9/2009 | Rau | |
| 2010/0004431 A1* | 1/2010 | Bernett | C07K 16/00 530/387.9 |
| 2011/0104148 A1 | 5/2011 | Moessner | |
| 2014/0120554 A1 | 5/2014 | Markel | |
| 2014/0161870 A1* | 6/2014 | Rabuka | C07K 16/2851 424/450 |
| 2015/0337037 A1* | 11/2015 | Kim | C07K 16/2866 424/172.1 |
| 2015/0353628 A1* | 12/2015 | Maynard | C07K 16/1225 424/450 |
| 2017/0355781 A1* | 12/2017 | Markel | C07K 16/3007 |

FOREIGN PATENT DOCUMENTS

| | | |
|---|---|---|
| EP | 1276770 | 10/2007 |
| EP | 1558284 | 9/2013 |
| WO | 8601533 | 3/1986 |
| WO | 9007861 | 7/1990 |
| WO | 9222653 | 12/1992 |
| WO | 9311161 | 6/1993 |
| WO | 9315210 | 8/1993 |
| WO | 9613583 | 5/1996 |
| WO | 9637621 | 11/1996 |
| WO | 9952552 | 10/1999 |
| WO | 0113937 | 3/2001 |
| WO | 0212535 | 2/2002 |
| WO | 02068601 | 9/2002 |
| WO | 03087319 | 10/2003 |
| WO | 03093315 | 11/2003 |
| WO | 2004032857 | 4/2004 |
| WO | 2007063424 | 6/2007 |
| WO | 2007071426 A1 | 6/2007 |
| WO | 2008029271 | 3/2008 |
| WO | 2009141679 | 11/2009 |
| WO | 2010125571 | 11/2010 |
| WO | 2011010309 | 1/2011 |
| WO | 2013054320 | 4/2013 |
| WO | 2013054331 | 4/2013 |
| WO | 2013082366 | 6/2013 |
| WO | 2014055967 | 4/2014 |
| WO | 2014059251 | 4/2014 |
| WO | 2015075710 | 5/2015 |
| WO | 2015075725 | 5/2015 |
| WO | 2015101996 | 7/2015 |

OTHER PUBLICATIONS

Riley et al., (2009) Design and activity of a murine and humanized anti-CEACAM6 single-chain variable fragment in the treatment of pancreatic cancer. Cancer research, 69(5), 1933-1940.

Tilki et al., (2006) CEA-related cell adhesion molecule-1 is involved in angiogenic switch in prostate cancer. Oncogene, 25(36), 4965-4974.

Albarran-Somoza et al., (2006) CEACAM1 in cervical cancer and precursor lesions: association with human papillomavirus infection. J Histochem Cytochem 54(12): 1393-9.

Almagro & Fransson., (2008) Humanization of antibodies. Front Biosci, 13(1), 1619-1633.

Azuz-Lieberman et al., (2005) The involvement of NK cells in ankylosing spondylitis. Int Immunol 17(7): 837-45.

Besser et al., (2009) Minimally cultured or selected autologous tumor-infiltrating lymphocytes after a lympho-depleting chemotherapy regimen in metastatic melanoma patients. J Immunother 32(4): 415-423.

Besser et al., (2010) Clinical responses in a phase II study using adoptive transfer of short-term cultured tumor infiltration lymphocytes in metastatic melanoma patients. Clin Cancer Res 16(9): 2646-2655.

Bird et al., (1988) Single-chain antigen-binding proteins. Science (New York, NY), 242(4877), 423-426.

Boerner et al., (1991) Production of antigen-specific human monoclonal antibodies from in vitro-primed human splenocytes. J Immunol 147(1): 86-95.

Brand et al., (2006) Prospect for anti-HER2 receptor therapy in breast cancer. Anticancer Res 26(1B): 463-470.

Brennan et al., (1985) Preparation of bispecific antibodies by chemical recombination of monoclonal immunoglobulin G1 fragments. Science 229(4708): 81-3.

Brüggemann et al., (1993) Designer mice: the production of human antibody repertoires in transgenic animals. Year Immunol 7: 33-40.

Bryson et al., (2010) Prediction of Immunogenicity of Therapeutic Proteins. BioDrugs, 24(1), 1-8.

Carter et al., (1992) High level *Escherichia coli* expression and production of a bivalent humanized antibody fragment. Biotechnology (N Y) 10(2):163-7.

Carter et al., (1992) Humanization of an anti-p185HER2 antibody for human cancer therapy. Proc Natl Acad Sci U S A 89(10): 4285-9.

Chothia and Lesk (1987) Canonical structures for the hypervariable regions of immunoglobulins. J Mol Biol 196(4): 901-17.

Clackson et al., (1991) Making antibody fragments using phage display libraries. Nature, 352(6336), 624-628.

Clark (1997) IgG effector mechanisms. Chem Immunol 65: 88-110.

Cruse JM and Lewis RE (2003) "Illustrated Dictionary of Immunology", 2nd Ed., CRC Press, p. 42.

Dolan & Gupta., (2014) PD-1 pathway inhibitors: changing the landscape of cancer immunotherapy. Cancer control: journal of the Moffitt Cancer Center, 21(3), 231-237.

Douillard et al., (2000) Irinotecan combined with fluorouracil compared with fluorouracil alone as first-line treatment for metastatic colorectal cancer: a multicentre randomised trial. Lancet 355(9209): 1041-7.

Duchosal et al., (1992) Immunization of hu-PBL-SCID mice and the rescue of human monoclonal Fab fragments through combinatorial libraries. Nature 355(6357): 258-62.

Duffy (2001) Carcinoembryonic antigen as a marker for colorectal cancer: is it clinically useful? Clin Chem 47(4): 624-30.

(56) References Cited

OTHER PUBLICATIONS

Fishwild et al., (1996) High-avidity human IgG kappa monoclonal antibodies from a novel strain of minilocus transgenic mice. Nat Biotechnol 14(7): 845-51.
Gelao et al., (2014) Immune checkpoint blockade in cancer treatment: a double-edged sword cross-targeting the host as an "innocent bystander". Toxins, 6(3), 914-933.
Gong et al., (2011) Diagnostic value of serum CEACAM1 in patients with pancreatic cancer. J South Med Univ 31: 164-167.
Gray-Owen and Blumberg (2006) CEACAM1: contact-dependent control of immunity. Nat Rev Immunol 6(6): 433-46.
Hamid et al., (2013) Safety and tumor responses with lambrolizumab (anti-PD-1) in melanoma. New England Journal of Medicine, 369(2), 134-144.
Hansen et al., (1993) Characterization of second-generation monoclonal antibodies against carcinoembryonic antigen. Cancer 71(11): 3478-3485.
Holliger et al., (1993) "Diabodies": small bivalent and bispecific antibody fragments. Proceedings of the National Academy of Sciences, 90(14), 6444-6448.
Hoogenboom and Winter (1992) By-passing immunisation. Human antibodies from synthetic repertoires of germline VH gene segments rearranged in vitro. J Mol Biol 227(2): 381-8.
Hussain et al., (1995) Selective increases in antibody isotypes and immunoglobulin G subclass responses to secreted antigens in tuberculosis patients and healthy household contacts of the patients. Clin Diagn Lab Immunol 2(6): 726-32.
Huston et al., (1988) Protein engineering of antibody binding sites: recovery of specific activity in an anti-digoxin single-chain Fv analogue produced in *Escherichia coli*. Proceedings of the National Academy of Sciences, 85(16), 5879-5883.
Imakiire et al., (2004) Generation, immunologic characterization and antitumor effects of human monoclonal antibodies for carcinoembryonic antigen. International journal of cancer 108(4): 564-570.
Inbar et al., (1972) Localization of antibody-combining sites within the variable portions of heavy and light chains. Proc Natl Acad Sci USA 69(9): 2659-6262.
Jakobovits et al., (1993) Analysis of homozygous mutant chimeric mice: deletion of the immunoglobulin heavy-chain joining region blocks B-cell development and antibody production. Proc Natl Acad Sci U S A 90(6): 2551-5.
Jakobovits et al., (1993) Germ-line transmission and expression of a human-derived yeast artificial chromosome. Nature 362(6417): 255-8.
Jin et al., (2008) The research progress of carcino-embryonic antigen related cellular adhesion molecule 1. China Oncology 18(4) 310-314 Translated abstract.
Jones et al., (1986) Replacing the complementarity-determining regions in a human antibody with those from a mouse. Nature 321(6069): 522-5.
Kammerer et al., (2004) The tumour suppressor gene CEACAM1 is completely but reversibly downregulated in renal cell carcinoma J Pathol 204(3): 258-267.
Kataja et al., (2009) Primary breast cancer: ESMO clinical recommendations for diagnosis, treatment and follow-up. Ann Oncol 20(Suppl 4): iv10-4.
Khatib et al., (2011) Carcinoembryonic antigen cell adhesion molecule-1 (CEACAM1) in posterior uveal melanoma: correlation with clinical and histological survival markers. Invest Ophthalmol Vis Sci 52(13): 9368-72.
Kim et al., (2005) Antibody engineering for the development of therapeutic antibodies. Mol Cells 20(1).
Köhler & Milstein., (1975) Continuous cultures of fused cells secreting antibody of predefined specificity. nature, 256, 495-497.
Köhler (1980) Immunoglobulin chain loss in hybridoma lines. Proc Natl Acad Sci U S A 77(4): 2197-2199.
Kozbor and Roder (1983) The production of monoclonal antibodies from human lymphocytes. Immunology Today 4(3): 72-79.
Kromenaker and Srienc (1994) Stability of producer hybridoma cell lines after cell sorting: A case study. Biotechnology 10(3): 299-307.
Laack et al., (2002) Expression of CEACAM1 in adenocarcinoma of the lung: a factor of independent prognostic significance. J Clin Oncol 20(21): 4279-84.
Larrick and Fry (1991) PCR amplification of antibody genes. Methods 2(2): 106-110.
Lefranc et al., (1999) IMGT, the international ImMunoGeneTics database. Nucleic Acids Res 27(1): 209-12.
Liersch et al., (2005) Phase II trial of carcinoembryonic antigen radioimmunotherapy with 131I-labetuzumab after salvage resection of colorectal metastases in the liver: five-year safety and efficacy results. J Clin Oncol 23(27): 6763-70.
Lonberg and Huszar (1995) Human antibodies from transgenic mice. Int Rev Immunol 13(1): 65-93.
Whitlow and Filpula (1991) Single-chain Fv proteins and their fusion proteins. Methods 2(2): 97-105.
Wu and Kabat (1970) An analysis of the sequences of the variable regions of Bence Jones proteins and myeloma light chains and their implications for antibody complementarity. J Exp Med 132(2): 211-50.
Ychou et al., (2008) Adjuvant radioimmunotherapy trial with iodine-131-labeled anti-carcinoembryonic antigen monoclonal antibody F6 F(ab')2 after resection of liver metastases from colorectal cancer. Clin Cancer Res 14(11): 3487-93.
Zapata et al., (1995) Engineering linear F (ab') 2 fragments for efficient production in *Escherichia coli* and enhanced antiproliferative activity. Protein engineering, 8(10), 1057-1062.
Zheng et al., (2011) A novel anti-CEACAM5 monoclonal antibody, CC4, suppresses colorectal tumor growth and enhances NK cells-mediated tumor immunity. PLoS One 6(6): e21146.
Lonberg et al., (1994) Antigen-specific human antibodies from mice comprising four distinct genetic modifications. Nature 368(6474): 856-9.
Mariuzza et al., (1987) The structural basis of antigen-antibody recognition. Annu Rev Biophys Biophys Chem 16: 139-59.
Markel et al., (2002) CD66a interactions between human melanoma and NK cells: a novel class I MHC-independent inhibitory mechanism of cytotoxicity. J Immunol 168(6): 2803-10.
Markel et al., (2004) Biological function of the soluble CEACAM1 protein and implications in TAP2-deficient patients. Eur J Immunol 34(8): 2138-2148.
Markel et al., (2004) The critical role of residues 43R and 44Q of carcinoembryonic antigen cell adhesion molecules-1 in the protection from killing by human NK cells. J Immunol 173(6): 3732-9.
Markel et al., (2004) The mechanisms controlling NK cell autoreactivity in TAP2-deficient patients. Blood 103(5): 1770-1778.
Markel et al., (2006) Inhibition of human tumor-infiltrating lymphocyte effector functions by the homophilic carcinoembryonic cell adhesion molecule 1 interactions. J Immunol 177(9): 6062-71.
Markel et al., (2009) Dynamic expression of protective CEACAM1 on melanoma cells during specific immune attack. Immunology 126(2): 186-200.
Markel et al., (2010) Systemic dysregulation of CEACAM1 in melanoma patients. Cancer Immunol Immunother 59(2): 215-30.
Marks et al., (1991) By-passing immunization: human antibodies from V-gene libraries displayed on phage. Journal of molecular biology, 222(3), 581-597.
Marks et al., (1992) By-passing immunization: building high affinity human antibodies by chain shuffling. Biotechnology (N Y) 10(7): 779-83.
McCafferty et al., (1990) Phage antibodies: filamentous phage displaying antibody variable domains. Nature 348(6301): 552-4.
McCarthy and Hill (2001) Altering the fine specificity of an anti-Legionella single chain antibody by a single amino acid insertion. J Immunol Methods 251(1-2): 137-49.
Morales et al., (1999) Regulation of human intestinal intraepithelial lymphocyte cytolytic function by biliary glycoprotein (CD66a). J Immunol 163(3): 1363-70.
Morimoto and Inouye (1992) Single-step purification of F(ab')2 fragments of mouse monoclonal antibodies (immunoglobulins G1)

(56) References Cited

OTHER PUBLICATIONS by hydrophobic interaction high performance liquid chromatography using TSKgel Phenyl-5PW. J Biochem Biophys Methods 24(1-2): 107-170.
Morrison (1994) Immunology. Success in specification. Nature 368(6474): 812-3.
Müller et al., (1998) A dimeric bispecific miniantibody combines two specificities with avidity. FEBS Lett 432(1-2): 45-9.
Nelson et al., (2009) Screening for breast cancer: an update for the U.S. Preventive Services Task Force. Ann Intern Med 151(10): 727-737.
Neuberger (1996) Generating high-avidity human Mabs in mice. Nat Biotechnol 14(7): 826.
Oikawa et al., (1992) homotypic and heterotypic Ca++-independent cell adhesion activities of biliary glycoprotein, a member of carcinoembryonic antigen family, expressed on Cho cell surface. Biochemical and Biophysical Research Communications 186(2): 881-887.
Ozturk and Palsson (1990) Loss of antibody productivity during long-term cultivation of a hybridoma cell line in low serum and serum-free media. Hybridoma 9(2): 167-175.
Pack et al., (1993) Improved bivalent miniantibodies, with identical avidity as whole antibodies, produced by high cell density fermentation of *Escherichia coli*. BioTechnology (N Y) 11(11): 1271-1277.
Pardoll ., (2012) The blockade of immune checkpoints in cancer immunotherapy. Nature Reviews Cancer, 12(4), 252-264.
Pavoni et al., (2006) Selection, affinity maturation, and characterization of a human scFv antibody against CEA protein. BMC Cancer 6: 41.
Perry et al., (2008) New approaches to prediction of immune responses to therapeutic proteins during preclinical development. Drugs in R & D, 9(6), 385-396.
Porter (1959) The hydrolysis of rabbit y-globulin and antibodies with crystalline papain. Biochem J 73: 119-126 application.
Presta (1992) Antibody engineering. Current Opinion in Structural Biology 2(4): 593-596.
Presta et al., (1993) Humanization of an antibody directed against IgE. J Immunol 151(5): 2623-32.
Presta et al., (1997) Humanization of an anti-vascular endothelial growth factor monoclonal antibody for the therapy of solid tumors and other disorders. Cancer Res 57(20): 4593-9.
Primus et al., (1983) Immunological heterogeneity of carcinoembryonic antigen: antigenic determinants on carcinoembryonic antigen distinguished by monoclonal antibodies. Cancer Research 43: 686-692.
Riechmann et al., (1988) Reshaping human antibodies for therapy. Nature 332(6162): 323-7.
Robert et al., (2011) Ipilimumab plus dacarbazine for previously untreated metastatic melanoma. New England Journal of Medicine, 364(26), 2517-2526.
Roder, John C. et al., (1985) Recent advances in the ebv-hybridoma technique. In: Monoclonal antibodies and cancer therapy. Journal of Cellular Biochemistry Supplement: UCLA Symposia on Molecular & Cellular Biology 29(9A): 33-74 abstract #0106.
Roitt I.M., Brostoff J. & Male D. (1998) Immunology. 5th edition, 1998 Mosby International Ltd., London. p. 80.
Rudikoff et al., (1982) Single amino acid substitution altering antigen-binding specificity. Proc Natl Acad Sci U S A 79(6): 1979-1983.
Saltz et al., (1999) Weekly irinotecan (CPT-11), leucovorin (LV), and fluorouracil (FU) is superior to daily x5 LV/FU in patients (pts) with previously untreated metastatic colorectal cancer. Proc Am Soc Clin Oncol 18: 233a.

Schillbach et al., (1993) Modulation of antibody affinity by a non-contact residue. Protein Sci 2(2): 206-14.
Sheets et al., (1998) Efficient construction of a large nonimmune phage antibody library: the production of high-affinity human single-chain antibodies to protein antigens. Proc Natl Acad Sci U S A 95(11): 6157-62.
Sienel et al., (2003) Elevated expression of carcinoembryonic antigen-related cell adhesion molecule 1 promotes progression of non-small cell lung cancer Clin Cancer Res 9(6): 2260-6.
Simeone et al., (2007) CEACAM1, a novel serum biomarker for pancreatic cancer. Pancreas 34(4): 436-43.
Sims et al., (1993) A humanized CD18 antibody can block function without cell destruction. J Immunol 151(4): 2296-308.
Slootstra et al., (1996) Structural aspects of antibody-antigen interaction revealed through small random peptide libraries. Mol Divers 1(2): 87-96.
Stern et al., (2005) Carcinoembryonic antigen (CEA) inhibits NK killing via interaction with CEA-related cell adhesion molecule 1. J Immunol 174(11): 6692-701.
Thies et al., (2002) CEACAM1 expression in cutaneous malignant melanoma predicts the development of metastatic disease. J Clin Oncol 20(10): 2530-2536.
Thompson et al., (1991) Carcinoembryonic antigen gene family: molecular biology and clinical perspectives. J Clin Lab Anal 5(5): 344-66.
Timmerman et al., (2007) Functional reconstruction and synthetic mimicry of a conformational epitope using CLIPS technology. J Mol Recognit 20(5): 283-99.
Vaughan et al., (1996) Human antibodies with sub-nanomolar affinities isolated from a large non-immunized phage display library. Nat Biotechnol 14(3): 309-14.
Verhoeyen et al., (1988) Reshaping human antibodies: grafting an antilysozyme activity. Science 239(4847): 1534-6.
Ward et al., (1989) Binding activities of a repertoire of single immunoglobulin variable domains secreted from *Escherichia coli*. Nature, 341(6242), 544-546.
Watt et al., (2001) Homophilic adhesion of human CEACAM1 involves N-terminal domain interactions: structural analysis of the binding site. Blood, 98(5), 1469-1479.
Bartolazzi et al., (2008) Galectin-3-expression analysis in the surgical selection of follicular thyroid nodules with indeterminate fine-needle aspiration cytology: a prospective multicentre study. The Lancet Oncology, 9(6), 543-549.
Ben Moshe (2016) CM-24 / MK-6018, a novel anti CEACAM1 therapy for treating cancer. ICI Meeting, Boston, Mar. 2016. 36 pages.
Carroll (2017); Endpoints News Mar. 24, 2017; That $95M Merck gamble to acquire cCAM? It didn't pay off. Retrieved on Mar. 1, 2018 from URL: https://endpts.com/that-95m-merck-gamble-to-acquire-ccam-it-didnt-pay-off/. 2 pages.
Ortenberg et al., (2012) Novel immunotherapy for malignant melanoma with a monoclonal antibody that blocks CEACAM1 homophilic interactions. Mol Cancer Ther 11(6): 1300-1310.
Warne (2011) Development of high concentration protein biopharmaceuticals: the use of platform approaches in formulation development. Eur J Pharm Biopharm 78(2): 208-212.
Koti, M. et al., "A single point mutation in framework region 3 of heavy chain affects viral neutralization dynamics of single-chain Fv against bovine herpes virus type 1", Vaccine 29 (2011) 7905-7912.
Honegger, A. et al., "The influence of the framework core residues on the biophysical properties of immunoglobulin heavy chain variable domains", Protein Engineering, Design & Selection vol. 22 No. 3 pp. 121-134, 2009.

* cited by examiner

```
  1  DIQMTQSPSS LSASVGDRVT ITCRTSQDIG NYLNWYQQKP GKAVKLLIYY
 51  TSRLHSGVPS RFSGSGSGTD YTLTISSLQP EDIATYFCQQ GKSLPRTFGG
101  GTKVEIKRTV AAPSVFIFPP SDEQLKSGTA SVVCLLNNFY PREAKVQWKV
151  DNALQSGNSQ ESVTEQDSKD STYSLSSTLT LSKADYEKHK VYACEVTHQG
201  LSSPVTKSFN RGEC
```

FIGURE 15A

```
  1  QVQLVQSGAE VKKPGASVKV SCKASGYAFT NNLIEWVRQA PGQGLEWIGV
 51  INPGSGDTNY NEKFKGRVTM TADKSISTAY MELSRLRSDD TAVYYCARGD
101  YYGGFAVDYW GQGTTVTVSS ASTKGPSVFP LAPCSRSTSE STAALGCLVK
151  DYFPEPVTVS WNSGALTSGV HTFPAVLQSS GLYSLSSVVT VPSSSLGTKT
201  YTCNVDHKPS NTKVDKRVES KYGPPCPPCP APEFLGGPSV FLFPPKPKDT
251  LMISRTPEVT CVVVDVSQED PEVQFNWYVD GVEVHNAKTK PREEQFNSTY
301  RVVSVLTVLH QDWLNGKEYK CKVSNKGLPS SIEKTISKAK GQPREPQVYT
351  LPPSQEEMTK NQVSLTCLVK GFYPSDIAVE WESNGQPENN YKTTPPVLDS
401  DGSFFLYSRL TVDKSRWQEG NVFSCSVMHE ALHNHYTQKS LSLSLGK
```

FIGURE 15B

```
  1  QVQLVQSGAE VKKPGASVKV SCKASGYAFT NNLIEWVRQA PGQGLEWIGV
 51  INPGSGDTNY NEKFKGRVTM TADKSISTAY MELSRLRSDD TAVYYCARGD
101  YYGGFAVDYW GQGTTVTVSS ASTKGPSVFP LAPSSKSTSG GTAALGCLVK
151  DYFPEPVTVS WNSGALTSGV HTFPAVLQSS GLYSLSSVVT VPSSSLGTQT
201  YICNVNHKPS NTKVDKRVEP KSCDKTHTCP PCPAPELLGG PSVFLFPPKP
251  KDTLMISRTP EVTCVVVDVS HEDPEVKFNW YVDGVEVHNA KTKPREEQYN
301  STYRVVSVLT VLHQDWLNGK EYKCKVSNKA LPAPIEKTIS KAKGQPREPQ
351  VYTLPPSREE MTKNQVSLTC LVKGFYPSDI AVEWESNGQP ENNYKTTPPV
401  LDSDGSFFLY SKLTVDKSRW QQGNVFSCSV MHEALHNHYT QKSLSLSPGK
```

FIGURE 15C

SEQUENCE LISTING

<160> NUMBER OF SEQ ID NOS: 59

<210> SEQ ID NO 1
<211> LENGTH: 10
<212> TYPE: PRT
<213> ORGANISM: Artificial Sequence
<220> FEATURE:
<223> OTHER INFORMATION: synthetic peptide

<400> SEQUENCE: 1

Gly Tyr Ala Phe Thr Asn Asn Leu Ile Glu
1               5                   10

<210> SEQ ID NO 2
<211> LENGTH: 17
<212> TYPE: PRT
<213> ORGANISM: Artificial Sequence
<220> FEATURE:
<223> OTHER INFORMATION: synthetic peptide

<400> SEQUENCE: 2

Val Ile Asn Pro Gly Ser Gly Asp Thr Asn Tyr Asn Glu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: synthetic sequence

<400> SEQUENCE: 3

Gly Asp Tyr Tyr Gly Gly Phe Ala Val Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic peptide

<400> SEQUENCE: 4

Arg Thr Ser Gln Asp Ile Gly Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Tyr Thr Ser Arg Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Gln Gln Gly Lys Ser Leu Pro Arg Thr
1               5

<210> SEQ ID NO 7
<211> LENGTH: 25
<212> TYPE: PRT
<213> ORGANISM: Artificial Sequence
<220> FEATURE:
<223> OTHER INFORMATION: synthetic peptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 8
<211> LENGTH: 14
<212> TYPE: PRT
<213> ORGANISM: Artificial Sequence
<220> FEATURE:
<223> OTHER INFORMATION: synthetic peptide

<400> SEQUENCE: 8

Trp Val Arg Gln Ala Pro Gly Gln Gly Leu Glu Trp Met Gly
1               5                   10

<210> SEQ ID NO 9
<211> LENGTH: 32
<212> TYPE: PRT
<213> ORGANISM: Artificial Sequence
<220> FEATURE:
<223> OTHER INFORMATION: synthetic peptide

<400> SEQUENCE: 9

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: synthetic peptide

<400> SEQUENCE: 10

Trp Gly Gln Gly Thr Thr Val Thr Val Ser Ser
1               5                   10

<210> SEQ ID NO 11
<211> LENGTH: 23
<212> TYPE: PRT
<213> ORGANISM: Artificial Sequence
<220> FEATURE:
<223> OTHER INFORMATION: synthetic peptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 12

```
<211> LENGTH: 15
<212> TYPE: PRT
<213> ORGANISM: Artificial Sequence
<220> FEATURE:
<223> OTHER INFORMATION: synthetic peptide

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: synthetic peptide

<400> SEQUENCE: 13

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
                20                  25                  30

<210> SEQ ID NO 14
<211> LENGTH: 10
<212> TYPE: PRT
<213> ORGANISM: Artificial Sequence
<220> FEATURE:
<223> OTHER INFORMATION: synthetic peptide

<400> SEQUENCE: 14

Phe Gly Gly Gly Thr Lys Val Glu Ile Lys
1               5                   10

<210> SEQ ID NO 15
<211> LENGTH: 25
<212> TYPE: PRT
<213> ORGANISM: Artificial Sequence
<220> FEATURE:
<223> OTHER INFORMATION: synthetic peptide

<400> SEQUENCE: 15

Gln Val Gln Leu Val Gln Ser Gly Ala Glu Leu Lys Lys Pro Gly Ala
1               5                   10                  15

Ser Val Lys Val Ser Cys Lys Ala Ser
                20                  25

<210> SEQ ID NO 16
<211> LENGTH: 14
<212> TYPE: PRT
<213> ORGANISM: Artificial Sequence
<220> FEATURE:
<223> OTHER INFORMATION: synthetic peptide

<400> SEQUENCE: 16

Trp Val Lys Gln Ala Pro Gly Gln Gly Leu Glu Trp Ile Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic peptide

<400> SEQUENCE: 17
```

Trp Val Arg Gln Ala Pro Gly Gln Gly Leu Glu Trp Ile Gly
1               5                   10

<210> SEQ ID NO 18
<211> LENGTH: 32
<212> TYPE: PRT
<213> ORGANISM: Artificial Sequence
<220> FEATURE:
<223> OTHER INFORMATION: synthetic peptide

<400> SEQUENCE: 18

Arg Ala Thr Leu Thr Ala Asp Lys Ser Ile Asn Thr Ala Tyr Met Glu
1               5                   10                  15

Leu Ser Ser Leu Thr Ser Asp Asp Ser Ala Val Tyr Phe Cys Ala Arg
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: synthetic peptide

<400> SEQUENCE: 19

Arg Ala Thr Leu Thr Ala Asp Lys Ser Ile Asn Thr Ala Tyr Met Glu
1               5                   10                  15

Leu Ser Arg Leu Arg Ser Asp Asp Thr Ala Val Tyr Phe Cys Ala Arg
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: synthetic peptide

<400> SEQUENCE: 20

Arg Ala Thr Leu Thr Ala Asp Lys Ser Ile Asn Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: synthetic peptide

<400> SEQUENCE: 21

Arg Ala Thr Leu Thr Ala Asp Lys Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: synthetic peptide

<400> SEQUENCE: 22

Arg Val Thr Met Thr Ala Asp Lys Ser Ile Ser Thr Ala Tyr Met Glu
1               5                   10                  15

```
Leu Ser Arg Leu Arg Ser Asp Asp Thr Ala Val Tyr Tyr Cys Ala Arg
        20                  25                  30
```

<210> SEQ ID NO 23
<211> LENGTH: 11
<212> TYPE: PRT
<213> ORGANISM: Artificial Sequence
<220> FEATURE:
<223> OTHER INFORMATION: synthetic peptide

<400> SEQUENCE: 23

```
Trp Gly Gln Gly Thr Ser Val Thr Val Ser Ser
1               5                   10
```

<210> SEQ ID NO 24
<211> LENGTH: 15
<212> TYPE: PRT
<213> ORGANISM: Artificial Sequence
<220> FEATURE:
<223> OTHER INFORMATION: synthetic peptide

<400> SEQUENCE: 24

```
Trp Tyr Gln Gln Lys Pro Gly Lys Ala Val Lys Leu Leu Ile Tyr
1               5                   10                  15
```

<210> SEQ ID NO 25
<211> LENGTH: 32
<212> TYPE: PRT
<213> ORGANISM: Artificial Sequence
<220> FEATURE:
<223> OTHER INFORMATION: synthetic peptide

<400> SEQUENCE: 25

```
Gly Val Pro Ser Arg Phe Ser Gly Ser Gly Ser Gly Thr Asp Tyr Thr
1               5                   10                  15

Leu Thr Ile Ser Ser Leu Gln Gln Glu Asp Ile Ala Thr Tyr Phe Cys
            20                  25                  30
```

<210> SEQ ID NO 26
<211> LENGTH: 32
<212> TYPE: PRT
<213> ORGANISM: Artificial Sequence
<220> FEATURE:
<223> OTHER INFORMATION: sythetic peptide

<400> SEQUENCE: 26

```
Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Ile Ala Thr Tyr Phe Cys
            20                  25                  30
```

<210> SEQ ID NO 27
<211> LENGTH: 32
<212> TYPE: PRT
<213> ORGANISM: Artificial Sequence
<220> FEATURE:
<223> OTHER INFORMATION: synthetic peptide

<400> SEQUENCE: 27

```
Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Phe Cys
            20                  25                  30
```

<210> SEQ ID NO 28
<211> LENGTH: 120
<212> TYPE: PRT
<213> ORGANISM: Artificial Sequence
<220> FEATURE:
<223> OTHER INFORMATION: synthetic peptide

<400> SEQUENCE: 28

```
Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Ala Phe Thr Asn Asn
            20                  25                  30

Leu Ile Glu Trp Val Lys Gln Ala Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Arg Ala Thr Leu Thr Ala Asp Lys Ser Ile Asn Thr Ala Tyr
65                  70                  75                  80

Met Glu Leu Ser Ser Leu Thr Ser Asp Asp Ser Ala Val Tyr Phe Cys
                85                  90                  95

Ala Arg Gly Asp Tyr Tyr Gly Gly Phe Ala Val Asp Tyr Trp Gly Gln
            100                 105                 110

Gly Thr Ser Val Thr Val Ser Ser
        115                 120
```

<210> SEQ ID NO 29
<211> LENGTH: 120
<212> TYPE: PRT
<213> ORGANISM: Artificial Sequence
<220> FEATURE:
<223> OTHER INFORMATION: synthetic peptide

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Asn
            20                  25                  30

Leu Ile Glu Trp Val Lys Gln Ala Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Arg Ala Thr Leu Thr Ala Asp Lys Ser Ile Asn Thr Ala Tyr
65                  70                  75                  80

Met Glu Leu Ser Arg Leu Arg Ser Asp Asp Thr Ala Val Tyr Phe Cys
                85                  90                  95

Ala Arg Gly Asp Tyr Tyr Gly Gly Phe Ala Val Asp Tyr Trp Gly Gln
            100                 105                 110

Gly Thr Thr Val Thr Val Ser Ser
        115                 120
```

<210> SEQ ID NO 30
<211> LENGTH: 120
<212> TYPE: PRT
<213> ORGANISM: Artificial Sequence
<220> FEATURE:
<223> OTHER INFORMATION: synthetic peptide

<400> SEQUENCE: 30

```
Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Ala Phe Thr Asn Asn
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Arg Ala Thr Leu Thr Ala Asp Lys Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Gly Phe Ala Val Asp Tyr Trp Gly Gln
            100                 105                 110

Gly Thr Thr Val Thr Val Ser Ser
            115                 120

<210> SEQ ID NO 31
<211> LENGTH: 120
<212> TYPE: PRT
<213> ORGANISM: Artificial Sequence
<220> FEATURE:
<223> OTHER INFORMATION: synthetic peptide

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Asn
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Arg Ala Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Gly Phe Ala Val Asp Tyr Trp Gly Gln
            100                 105                 110

Gly Thr Thr Val Thr Val Ser Ser
            115                 120

<210> SEQ ID NO 32
<211> LENGTH: 120
<212> TYPE: PRT
<213> ORGANISM: Artificial Sequence
<220> FEATURE:
<223> OTHER INFORMATION: synthetic peptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Asn
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Arg Val Thr Met Thr Ala Asp Lys Ser Ile Ser Thr Ala Tyr

```
                65                  70                  75                  80
Met Glu Leu Ser Arg Leu Arg Ser Asp Asp Thr Ala Val Tyr Tyr Cys
                    85                  90                  95

Ala Arg Gly Asp Tyr Tyr Gly Gly Phe Ala Val Asp Tyr Trp Gly Gln
                100                 105                 110

Gly Thr Thr Val Thr Val Ser Ser
            115                 120

<210> SEQ ID NO 33
<211> LENGTH: 107
<212> TYPE: PRT
<213> ORGANISM: Artificial Sequence
<220> FEATURE:
<223> OTHER INFORMATION: synthetic peptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Gln
65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Val Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: synthetic peptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
```

-continued

<223> OTHER INFORMATION: synthetic peptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Val Glu Ile Lys
            100                 105

<210> SEQ ID NO 36
<211> LENGTH: 25
<212> TYPE: PRT
<213> ORGANISM: Artificial Sequence
<220> FEATURE:
<223> OTHER INFORMATION: synthetic peptide

<400> SEQUENCE: 36

Gln Val Gln Leu Gln Gln Ser Gly Ala Glu Leu Val Arg Pro Gly Thr
1               5                   10                  15

Ser Val Lys Val Ser Cys Lys Ala Ser
            20                  25

<210> SEQ ID NO 37
<211> LENGTH: 14
<212> TYPE: PRT
<213> ORGANISM: Artificial Sequence
<220> FEATURE:
<223> OTHER INFORMATION: synthetic peptide

<400> SEQUENCE: 37

Trp Val Lys Gln Arg Pro Gly Gln Gly Leu Glu Trp Ile Gly
1               5                   10

<210> SEQ ID NO 38
<211> LENGTH: 32
<212> TYPE: PRT
<213> ORGANISM: Artificial Sequence
<220> FEATURE:
<223> OTHER INFORMATION: stnthetic peptide

<400> SEQUENCE: 38

Lys Ala Thr Leu Thr Ala Asp Lys Ser Ser Asn Thr Ala Tyr Met Gln
1               5                   10                  15

Leu Ser Ser Leu Thr Ser Asp Asp Ser Ala Val Tyr Phe Cys Ala Arg
            20                  25                  30

<210> SEQ ID NO 39
<211> LENGTH: 11
<212> TYPE: PRT
<213> ORGANISM: Artificial Sequence
<220> FEATURE:
<223> OTHER INFORMATION: synthetic peptide

<400> SEQUENCE: 39

```
Trp Gly Gln Gly Thr Ser Val Thr Val Ser Ser
1               5                   10

<210> SEQ ID NO 40
<211> LENGTH: 23
<212> TYPE: PRT
<213> ORGANISM: Artificial Sequence
<220> FEATURE:
<223> OTHER INFORMATION: synthetic peptide

<400> SEQUENCE: 40

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 41
<211> LENGTH: 15
<212> TYPE: PRT
<213> ORGANISM: Artificial Sequence
<220> FEATURE:
<223> OTHER INFORMATION: synthetic peptide

<400> SEQUENCE: 41

Trp Tyr Gln Gln Lys Pro Asp Gly Thr Val Lys Leu Leu Ile Tyr
1               5                   10                  15

<210> SEQ ID NO 42
<211> LENGTH: 32
<212> TYPE: PRT
<213> ORGANISM: Artificial Sequence
<220> FEATURE:
<223> OTHER INFORMATION: synthetic peptide

<400> SEQUENCE: 42

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30

<210> SEQ ID NO 43
<211> LENGTH: 10
<212> TYPE: PRT
<213> ORGANISM: Artificial Sequence
<220> FEATURE:
<223> OTHER INFORMATION: synthetic peptide

<400> SEQUENCE: 43

Phe Gly Gly Gly Thr Lys Leu Glu Ile Lys
1               5                   10

<210> SEQ ID NO 44
<211> LENGTH: 360
<212> TYPE: DNA
<213> ORGANISM: Artificial Sequence
<220> FEATURE:
<223> OTHER INFORMATION: Synthetic polynucleotide sequence

<400> SEQUENCE: 44
caggtgcagc tggtgcagtc tggcgccgag ctgaagaaac ctggcgcctc tgtgaaggtg      60
tcctgcaagg cctccggcta cgccttcacc aacaacctga tcgagtgggt caaacaggcc     120
ccaggccagg gcctggaatg gatcggcgtg atcaaccccg gctccggcga caccaactac     180
aacgagaagt tcaagggccg ggccaccctg accgccgaca gtccatcaa caccgcctac     240
```

```
atggagctgt cctccctgac ctccgacgac tccgccgtgt acttctgcgc cagaggcgac    300
tactacggcg gcttcgccgt ggattactgg ggccagggca cctccgtgac cgtgtcctca    360
```

<210> SEQ ID NO 45
<211> LENGTH: 360
<212> TYPE: DNA
<213> ORGANISM: Artificial Sequence
<220> FEATURE:
<223> OTHER INFORMATION: synthetic polynucleotide

<400> SEQUENCE: 45

```
caggtgcagc tggtgcagtc tggcgccgag gtgaagaaac ctggcgcctc tgtgaaggtg     60
tcctgcaagg cctccggcta cgccttcacc aacaacctga tcgagtgggt caaacaggcc    120
ccaggccagg gctggaatg gatcggcgtg atcaaccccg gctccggcga caccaactac    180
aacgagaagt tcaagggccg ggccaccctg accgccgaca agtccatcaa caccgcctac    240
atggagctgt ccagactgag gtccgacgac accgccgtgt acttctgcgc cagaggcgac    300
tactacggcg gcttcgccgt ggattactgg ggccagggca ccaccgtgac cgtgtcctca    360
```

<210> SEQ ID NO 46
<211> LENGTH: 360
<212> TYPE: DNA
<213> ORGANISM: Artificial Sequence
<220> FEATURE:
<223> OTHER INFORMATION: synthetic polynucleotide

<400> SEQUENCE: 46

```
caggtgcagc tggtgcagtc tggcgccgag gtgaagaaac ctggcgcctc tgtgaaggtg     60
tcctgcaagg cctccggcta cgccttcacc aacaacctga tcgagtgggt cagacaggcc    120
ccaggccagg gcctggaatg gatcggcgtg atcaaccccg gctccggcga caccaactac    180
aacgagaagt tcaagggccg ggccaccctg accgccgaca agtccatcaa caccgcctac    240
atggagctgt ccagactgag gtccgacgac accgccgtgt actactgcgc cagaggcgac    300
tactacggcg gcttcgccgt ggattactgg ggccagggca ccaccgtgac cgtgtcctca    360
```

<210> SEQ ID NO 47
<211> LENGTH: 360
<212> TYPE: DNA
<213> ORGANISM: Artificial Sequence
<220> FEATURE:
<223> OTHER INFORMATION: synthetic polynucleotide

<400> SEQUENCE: 47

```
caggtgcagc tggtgcagtc tggcgccgag gtgaagaaac ctggcgcctc tgtgaaggtg     60
tcctgcaagg cctccggcta cgccttcacc aacaacctga tcgagtgggt cagacaggcc    120
ccaggccagg gcctggaatg gatcggcgtg atcaaccccg gctccggcga caccaactac    180
aacgagaagt tcaagggccg ggccaccctg accgccgaca agtccatcag caccgcctac    240
atggagctgt ccagactgag gtccgacgac accgccgtgt actactgcgc cagaggcgac    300
tactacggcg gcttcgccgt ggattactgg ggccagggca ccaccgtgac cgtgtcctca    360
```

<210> SEQ ID NO 48
<211> LENGTH: 360
<212> TYPE: DNA
<213> ORGANISM: Artificial Sequence
<220> FEATURE:
<223> OTHER INFORMATION: synthetic polynucleotide

<400> SEQUENCE: 48

```
caggtgcagc tggtgcagtc tggcgccgag gtgaagaaac ctggcgcctc tgtgaaggtg      60
tcctgcaagg cctccggcta cgccttcacc aacaacctga tcgagtgggt cagacaggcc     120
ccaggccagg gcctggaatg gatcggcgtg atcaacccog ctccggcga caccaactac     180 aacgagaagt tcaagggccg ggtgaccatg accgccgaca agtccatcag caccgcctac     240
atggagctgt ccagactgag gtccgacgac accgccgtgt actactgcgc cagaggcgac     300
tactacggcg gcttcgccgt ggattactgg ggccagggca ccaccgtgac cgtgtcctca     360
```

<210> SEQ ID NO 49
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 49

```
gacatccaga tgacccagag cccttccagc ctgtccgcct ccgtgggcga cagagtgacc      60
atcacctgcc ggacctccca ggacatcggc aactacctga actggtatca gcagaaaccc     120
ggcaaggccg tgaagctgct gatctactac acctccoggc tgcactccgg cgtgccctcc     180
agattctccg gctctggctc cggcaccgac tacaccctga ccatcagcag cctgcagcag     240
gaagatatcg ctacctactt ctgtcagcag ggcaagtctc tgcctcggac ctttggcgga     300
ggcaccaagg tggaaatcaa a                                               321
```

<210> SEQ ID NO 50
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 50

```
gacatccaga tgacccagag cccttccagc ctgtccgcct ccgtgggcga cagagtgacc      60
atcacctgcc ggacctccca ggacatcggc aactacctga actggtatca gcagaaaccc     120
ggcaaggccg tgaagctgct gatctactac acctcccggc tgcactccgg cgtgccctcc     180
agattctccg gctctggctc cggcaccgac tacaccctga ccatcagcag cctgcagcct     240
gaagatatcg ctacctactt ctgtcagcag ggcaagtctc tgcctcggac ctttggcgga     300
ggcaccaagg tggaaatcaa a                                               321
```

<210> SEQ ID NO 51
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 51

```
gacatccaga tgacccagag cccttccagc ctgtccgcct ccgtgggcga cagagtgacc      60
atcacctgcc ggacctccca ggacatcggc aactacctga actggtatca gcagaaaccc     120
ggcaaggccg tgaagctgct gatctactac acctcccggc tgcactccgg cgtgccctcc     180
agattctccg gctctggctc cggcaccgac tacaccttca ccatcagcag cctgcagcct     240
gaagatatcg ctacctactt ctgtcagcag ggcaagtctc tgcctcggac ctttggcgga     300
ggcaccaagg tggaaatcaa a                                               321
```

<210> SEQ ID NO 52
<211> LENGTH: 214
<212> TYPE: PRT
<213> ORGANISM: Artificial Sequence
<220> FEATURE:
<223> OTHER INFORMATION: synthetic peptide

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 53
<211> LENGTH: 447
<212> TYPE: PRT
<213> ORGANISM: Artificial Sequence
<220> FEATURE:
<223> OTHER INFORMATION: synthetic peptide

<400> SEQUENCE: 53

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Asn
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Arg Val Thr Met Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
```

85                  90                  95
Ala Arg Gly Asp Tyr Tyr Gly Gly Phe Ala Val Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 54
<211> LENGTH: 1353
<212> TYPE: DNA
<213> ORGANISM: Artificial Sequence
<220> FEATURE:
<223> OTHER INFORMATION: synthetic polynucleotide

<400> SEQUENCE: 54
caggtgcagc tggtgcagtc tggcgccgag gtgaagaaac ctggcgcctc tgtgaaggtg      60

```
tcctgcaagg cctccggcta cgccttcacc aacaacctga tcgagtgggt cagacaggcc      120
ccaggccagg gcctggaatg gatcggcgtg atcaaccccg gctccggcga caccaactac      180
aacgagaagt tcaagggccg ggtgaccatg accgccgaca gtccatcag caccgcctac       240 atggagctgt ccagactgag gtccgacgac accgccgtgt actactgcgc cagaggcgac      300
tactacggcg gcttcgccgt ggattactgg ggccagggca ccaccgtgac cgtgtcctca      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagag agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggaagag     1080
atgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctat agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa tga                                  1353

<210> SEQ ID NO 55
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 55
caggtgcagc tggtgcagtc tggcgccgag gtgaagaaac ctggcgcctc tgtgaaggtg       60
tcctgcaagg cctccggcta cgccttcacc aacaacctga tcgagtgggt cagacaggcc      120
ccaggccagg gcctggaatg gatcggcgtg atcaaccccg gctccggcga caccaactac      180
aacgagaagt tcaagggccg ggtgaccatg accgccgaca gtccatcag caccgcctac       240 atggagctgt ccagactgag gtccgacgac accgccgtgt actactgcgc cagaggcgac      300
tactacggcg gcttcgccgt ggattactgg ggccagggca ccaccgtgac cgtgtcctca      360
gcttccacca agggcccatc cgtcttcccc ctggcgccct gctccaggag cacctccgag      420
agcacagccg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacgaagacc      600
tacacctgca atgtagatca caagcccagc aacaccaagg tggacaagag agttgagtcc      660
aaatatggtc ccccatgccc accatgccca gcacctgagt tcctgggggg accatcagtc      720
```

```
ttcctgttcc ccccaaaacc caaggacact ctcatgatct cccggacccc tgaggtcacg      780
tgcgtggtgg tggacgtgag ccaggaagac cccgaggtcc agttcaactg gtacgtggat      840
ggcgtggagg tgcataatgc caagacaaag ccgcgggagg agcagttcaa cagcacgtac      900
cgtgtggtca gcgtcctcac cgtcctgcac caggactggc tgaacggcaa ggagtacaag      960
tgcaaggtct ccaacaaagg cctcccgtcc tccatcgaga aaaccatctc caaagccaaa     1020
gggcagcccc gagagccaca ggtgtacacc ctgcccccat cccaggagga tgaccaag      1080 aaccaggtca gcctgacctg cctggtcaaa ggcttctacc ccagcgacat cgccgtggag     1140
tgggagagca atgggcagcc ggagaacaac tacaagacca cgcctcccgt gctggactcc     1200
gacggctcct tcttcctcta cagcaggcta accgtggaca agagcaggtg gcaggagggg     1260
aatgtcttct catgctccgt gatgcatgag gctctgcaca accactacac acagaagagc     1320 ctctcccctgt ctctgggtaa atga                                           1344
```

<210> SEQ ID NO 56
<211> LENGTH: 600
<212> TYPE: DNA
<213> ORGANISM: Artificial Sequence
<220> FEATURE:
<223> OTHER INFORMATION: synthetic polynucleotide

<400> SEQUENCE: 56

```
gacatccaga tgacccagag cccttccagc ctgtccgcct ccgtgggcga cagagtgacc       60
atcacctgcc ggacctccca ggacatcggc aactacctga actggtatca gcagaaaccc      120
ggcaaggccg tgaagctgct gatctactac acctcccggc tgcactccgg cgtgccctcc      180
agattctccg gctctggctc cggcaccgac tacaccctga ccatcagcag cctgcagcct      240
gaagatatcg ctacctactt ctgtcagcag ggcaagtctc tgcctcggac ctttggcgga      300
ggcaccaagg tggaaatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cacccctgacg      540 ctgagcaaag cagactacga gaaacacaaa gtctacgcct gcgaagtcac ccatcagggc      600
```

<210> SEQ ID NO 57
<211> LENGTH: 120
<212> TYPE: PRT
<213> ORGANISM: Artificial Sequence
<220> FEATURE:
<223> OTHER INFORMATION: synthetic peptide

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Asn
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Asp Thr Asn Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Gly Asp Tyr Tyr Gly Gly Phe Ala Val Asp Tyr Trp Gly Gln
                100                 105                 110

Gly Thr Thr Val Thr Val Ser Ser
            115                 120

<210> SEQ ID NO 58
<211> LENGTH: 107
<212> TYPE: PRT
<213> ORGANISM: Artificial Sequence
<220> FEATURE:
<223> OTHER INFORMATION: synthetic peptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Lys Ser Leu Pro Arg
                85                  90                  95

Thr Phe Gly Gly Gly Thr Lys Val Glu Ile Lys
            100                 105

<210> SEQ ID NO 59
<211> LENGTH: 450
<212> TYPE: PRT
<213> ORGANISM: Artificial Sequence
<220> FEATURE:
<223> OTHER INFORMATION: synthetic peptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Asn
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Asn Tyr Asn Glu Lys Phe
50                  55                  60

Lys Gly Arg Val Thr Met Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Gly Phe Ala Val Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
450
```

HUMANIZED ANTIBODIES AGAINST CEACAM1

CROSS-REFERENCE TO RELATED APPLICATIONS

The present application is a national stage filing under 35 U.S.C. § 371 of PCT/IL2015/050433, filed on Apr. 27, 2015, and claims the benefit of priority to U.S. Provisional Application No. 61/984,786, filed on Apr. 27, 2014 and 62/099,155, filed on Jan. 1, 2015. Each application is incorporated herein by reference in its entirety.

The present application includes a Sequence Listing filed in electronic format. The Sequence Listing is entitled "3596-204 ST25.txt" created on Jul. 18, 2018, and is 40,000 bytes in size. The information in the electronic format of the Sequence Listing is part of the present application and is incorporated herein by reference in its entirety.

FIELD OF THE INVENTION

The present invention mainly relates to humanized antibodies, capable of specific binding to human CEACAM molecules. More specifically, the present invention relates to antibodies against CEACAM1, comprising murine-derived CDRs and humanized heavy and light regions with specific back-mutations.

BACKGROUND OF THE INVENTION

Carcinoembryonic antigen-related cell adhesion molecule 1 (CEACAM1), also known as cluster of differentiation 66a (CD66a), is a member of the carcinoembryonic antigen (CEA) gene family and belongs to the immunoglobulin (Ig) superfamily CEACAM1 is upregulated in T and NK cells upon activation and its homophilic interactions lead to inhibition of lymphocytes cytotoxic effect. Studies of several human tumor types have suggested that the exploitation of the CEACAM1 pathway may permit immune evasion by tumors. Preclinical animal models of tumors have shown that blockade of CEACAM1 interactions by monoclonal antibodies (mAbs) can enhance the immune response to tumors. An estimated 1,660,290 new cases of cancer and 580,350 cancer-related deaths were seen in the United States in 2013.

Checkpoint Immunotherapy blockade has shown to be an exciting new venue of cancer treatment. Immune checkpoint pathways consist of a range of co-stimulatory and inhibitory molecules which work in concert in order to maintain self-tolerance and protect tissues from damage by the immune system under physiological conditions. Tumors take advantage of certain checkpoint pathways in order to evade the immune system. Therefore, the inhibition of such pathways has emerged as a promising anti-cancer treatment strategy (Pardoll, D. M., 2012, Nat Rev Cancer, 12, 252-264). Anti-tumor immunotherapy via CEACAM1 blockade is not limited in principle to any single tumor type, but may have activity in augmenting therapeutic immune response to a number of histologically distinct tumors.

The anti-cytotoxic T lymphocyte 4 (CTLA-4) antibody ipilimumab (approved in 2011) was the first immunotherapeutic agent that showed a benefit for the treatment of cancer patients (Robert et al., 2011, N. Engl. J. Med., Vol. 364, pages 2517-2526). The antibody interferes with inhibitory signals during antigen presentation to T cells. Anti-programmed cell death 1 (PD-1) antibody pembrolizumab (approved in 2014) blocks negative immune regulatory signaling of the PD-1 receptor expressed by T cells (Hamid, 2013, N. Engl. J. Med., Vol. 2, pages 134-144). Blocking antibodies of the PD-1/PL-L1 axis have shown promising results in several clinical trials in patients with various tumor types (Dolan and Gupta 2014, Cancer Control, Vol. 21, pages 231-237). An additional anti-PD-1 agent has been filed for regulatory approval in 2014 for the treatment of non-small cell lung cancer (NSCLC). Active research is currently exploring many other immune checkpoints, among them: lymphocyte activation gene 3 (LAG3), CD137, OX40 (also referred to as CD134), and killer cell immunoglobulin-like receptors (KIR) (Gelao et al., 2014, Toxins, Vol. 6, pages 914-933).

Humanized antibodies are antibodies from non-human species (e.g. murine antibodies) whose protein sequences have been modified to increase their similarity to antibody variants produced naturally in humans. The process of "humanization" is usually applied to monoclonal antibodies developed for administration to humans, and performed when the process of developing a specific antibody involves generation in a non-human immune system (such as in mice). The protein sequences of antibodies produced in this way are distinct from antibodies occurring naturally in humans, and are therefore immunogenic when administered to human patients. Humanized antibodies are considered distinct from chimeric antibodies, which have protein sequences similar to human antibodies, but carry large stretches of non-human protein.

It is possible to produce a humanized antibody without creating a chimeric intermediate. Direct creation of a humanized antibody can be accomplished by inserting the appropriate CDR coding segments (responsible for the desired binding properties) into a human antibody scaffold, a process known as "CDR grafting". In general, after an antibody is developed to have the desired properties in a mouse (or another non-human animal), the DNA coding for that antibody's CDRs can be sequenced. Once the precise sequences of the desired CDRs are known, these sequences are inserted into a construct containing the DNA for a human antibody framework.

WO 2010/125571 to the present inventors discloses a murine monoclonal antibody (MRG-1) produced by a specific hybridoma cell. The mAb is highly selective to CEACAM1 and does not cross-react with other members of the CEACAM family. WO 2013/054331 to the present inventors discloses a chimeric antibody (CM-10), also highly selective to CEACAM1.

Although there is progress in the field of immunotherapy, there remains a constant need for new treatments that are more effective and longer lasting and which involve novel targets and can work either as signal agents or in combination with known therapies in order to eventually generate long durable responses in cancer patients. There is an unmet need to provide humanized antibodies recognizing specific CEACAM proteins which are safer and more potent and can be used diagnostically and therapeutically in diseases involving CEACAM-proteins expression or activation.

SUMMARY OF THE INVENTION

The present invention provides humanized antibodies that recognized CEACAM1. Selected humanized antibodies according to the present invention contain numerous specific "back-mutations" in their variable region sequences, namely, mutations from the humanized sequence back to the mouse sequence. These back-mutations are made in residues critical for the maintenance of the original antibody's conformation and binding affinity, while having the lowest incidence of potential T cell epitopes, thus minimizing the risk of adverse immune response towards the antibodies.

In order to produce a humanized mAb which recognizes CEACAM1 having specific CDR sequences in desired orientation and conformation and human framework, the inventors of the present invention identified key residues in the human framework (outside the CDR sequences) that affect CDR presentation and designed an array of mutations is these key residues to restore the correct presentation of the CDRs, while minimizing the immunogenicity of the antibodies. The present invention thus provides, for the first time, a high-affinity, non-immunogenic, highly-specific humanized antibody against CEACAM1.

The present invention provides, according to one aspect, a humanized monoclonal antibody (mAb) which specifically recognizes human CEACAM1, or a fragment thereof comprising at least the antigenic-binding domain, comprising at least one variable region selected from the group consisting of: (i) a heavy-chain variable region comprising CDR1, CDR2 and CDR3 comprising the amino-acid sequences set forth in SEQ ID NO:1, SEQ ID NO:2 and SEQ ID NO:3, respectively; and (ii) a light-chain variable region comprising CDR1, CDR2 and CDR3 comprising the amino-acid sequences set forth in SEQ ID NO:4, SEQ ID NO:5 and SEQ ID NO:6, respectively; wherein at least one of (i) and (ii) contains 1-25 back-mutations of amino acid residues from a human to a murine sequence.

According to some embodiments, the invention provides a humanized monoclonal antibody (mAb) or a fragment thereof, which specifically recognizes human CEACAM1, comprising at least one variable region selected from the group consisting of (i) a heavy-chain variable region amino-acid sequence comprising the CDR sequences set forth in SEQ ID NO:1, SEQ ID NO:2 and SEQ ID NO:3, wherein the heavy-chain variable region amino-acid sequence differs from SEQ ID NO: 57 in 1-25 amino-acid residues in the framework sequences; and (ii) a light-chain variable region amino-acid sequence comprising the CDR sequences set forth in SEQ ID NO:4, SEQ ID NO:5 and SEQ ID NO:6, wherein the light-chain variable region amino-acid sequence differs from SEQ ID NO: 58 in 1-10 amino-acid residues in the framework sequences.

In certain embodiments, the invention provides a humanized monoclonal antibody (mAb) or a fragment thereof, which specifically recognizes human CEACAM1, comprising: (i) the CDR sequences set forth in SEQ ID NO:1, SEQ ID NO:2, SEQ ID NO:3, SEQ ID NO:4, SEQ ID NO:5 and SEQ ID NO:6; (ii) a heavy-chain variable region amino acid sequence that differs in 3-13 amino-acid framework residues from SEQ ID NO: 57; and (iii) a light-chain variable region amino-acid sequence that differs in 3-5 framework amino-acid residues from SEQ ID NO: 58.

According to certain embodiments, the heavy-chain variable region amino-acid sequence differs from SEQ ID NO: 57 in 3-13 amino-acid residues in the framework sequences. According to other embodiments, the light-chain variable region amino-acid sequence differs from SEQ ID NO: 58 in 3-5 amino-acid residues in the framework sequences.

According to other embodiments, the present invention provides a non-fully-humanized monoclonal antibody, comprising (i) a heavy-chain variable region comprising CDR1, CDR2 and CDR3 comprising the amino-acid sequences set forth in SEQ ID NO:1, SEQ ID NO:2 and SEQ ID NO:3, respectively, and a framework amino-acid sequence that differs in 2 to 9 amino-acids from the amino-acid sequence set forth in SEQ ID NO:9; and/or (ii) a light-chain variable region comprising CDR1, CDR2 and CDR3 comprising the amino-acid sequences set forth in SEQ ID NO:4, SEQ ID NO:5 and SEQ ID NO:6, respectively, and a framework amino-acid sequence that differs in 2 to 4 amino-acids from the amino-acid sequence set forth in SEQ ID NO:13; and analogs, derivatives and antigen-binding-fragments thereof which specifically recognize human CEACAM1.

According to some embodiments, the mAb sequence comprises 1-50 back-mutations to a murine sequence. According to other embodiments, the mAb sequence comprises 2-30 back-mutations to a murine sequence. According to yet other embodiments, the mAb sequence comprises 3-20 back-mutations to a murine sequence. According to other embodiments, the mAb sequence comprises 4-15 back-mutations to a murine sequence. According to other embodiments, the heavy chain of the mAb sequence comprises 1-15 back-mutations to a murine sequence. According to other embodiments, the light chain of the mAb sequence comprises 1-15 back-mutations to a murine sequence. According to other embodiments, the heavy chain of the mAb sequence comprises 2-9 back-mutations to a murine sequence and the light chain of the mAb sequence comprises 2-4 back-mutations to a murine sequence.

According to some specific embodiments, the humanized mAb comprises 1-25 mutations in the heavy chain sequence set forth in SEQ ID NO: 57 from human to murine sequence. According to some embodiments, the heavy chain of the humanized mAb comprises at least one mutation in a residue selected from the group consisting of: V11, R38, M48, V68, M70, R72, T74, S77, R85, R87, T91, Y95 and T115 of SEQ ID NO: 57. According to some embodiments, at least one back-mutation in SEQ ID NO: 57 is selected from the group consisting of: V11L, R38K, M48I, V68A, M70L, R72A, T74K, S77N, R85S, R87T, T91S, Y95F and T115S.

According to other some specific embodiments, the humanized mAb comprises 1-25 mutations in the light chain sequence set forth in SEQ ID NO: 58 from human to murine sequence. According to some embodiments, the light chain of the humanized mAb comprises at least one mutation in a residue selected from the group consisting of: P44, F71, F73, P80 and Y87 of SEQ ID NO: 58. According to some embodiments, the at least one back-mutation in SEQ ID NO: 58 is selected from the group consisting of: P44V, F71Y, F73L, P80Q, and Y87F.

According to some embodiments, the heavy chain of the humanized mAb comprises at least one mutation in a residue selected from the group consisting of: V11, R38, M48, V68, M70, R72, T74, S77, R85, R87, T91, Y95 and T115 of SEQ ID NO: 57, and the light chain of the humanized mAb comprises at least one mutation in a residue selected from the group consisting of: P44, F71, F73, P80 and Y87 of SEQ ID NO: 58. Each possibility represents a separate embodiment of the present invention.

According to some embodiments, the heavy chain of the humanized mAb comprises at least one mutation in a residue selected from the group consisting of: V68, M70, R72, T74, S77, R85, R87, T91, and Y95 of SEQ ID NO: 57, and the light chain of the humanized mAb comprises at least one mutation in a residue selected from the group consisting of: F71, F73, P80 and Y87 of SEQ ID NO: 58. Each possibility represents a separate embodiment of the present invention.

According to some embodiments, at least one back-mutation in SEQ ID NO: 57 is selected from the group consisting of: V11L, R38K, M48I, V68A, M70L, R72A, T74K, S77N, R85S, R87T, T91S, Y95F and T115S, and the at least one back-mutation in SEQ ID NO: 58 is selected from the group consisting of: P44V, F71Y, F73L, P80Q, and Y87F. Each possibility represents a separate embodiment of the present invention.

According to some embodiments, at least one back-mutation in SEQ ID NO: 57 is selected from the group consisting of: V68A, M70L, R72A, T74K, S77N, R85S, R87T, T91S, and Y95F, and the at least one back-mutation in SEQ ID NO: 58 is selected from the group consisting of: F71Y, F73L, P80Q, and Y87F. Each possibility represents a separate embodiment of the present invention.

In some embodiments, the monoclonal antibody comprises at least one heavy chain framework sequence set forth in a sequence selected from the group consisting of: SEQ ID NO:15, SEQ ID NO:16, SEQ ID NO:17, SEQ ID NO:18, SEQ ID NO:19, SEQ ID NO:20, SEQ ID NO:21, SEQ ID NO:12, and SEQ ID NO:23. In some embodiments, the monoclonal antibody comprises a heavy chain framework sequence set forth in a sequence selected from the group consisting of: SEQ ID NO:18, SEQ ID NO:19, SEQ ID NO:20, SEQ ID NO:21 and SEQ ID NO:22. Each possibility represents a separate embodiment of the present invention.

In some embodiments, the monoclonal antibody comprises heavy chain framework sequences set forth in SEQ ID NO:7 or SEQ ID NO:15; SEQ ID NO:16 or SEQ ID NO:17; SEQ ID NO:18, SEQ ID NO:19, SEQ ID NO:20, SEQ ID NO:21 or SEQ ID NO:22; and SEQ ID NO:10 or SEQ ID NO:23. Each possibility represents a separate embodiment of the present invention.

In some embodiments, the monoclonal antibody comprises a heavy chain variable region sequence set forth in a sequence selected from the group consisting of: SEQ ID NO:28, SEQ ID NO:29, SEQ ID NO:30, SEQ ID NO:31 and SEQ ID NO:32. Each possibility represents a separate embodiment of the present invention. In some specific embodiments, the monoclonal antibody comprises the heavy chain variable region sequence set forth in SEQ ID NO:32.

In some embodiments, the monoclonal antibody comprises a light chain framework sequence set forth in a sequence selected from the group consisting of: SEQ ID NO:24, SEQ ID NO:25, SEQ ID NO:26 and SEQ ID NO:27.

In some embodiments, the monoclonal antibody comprises a light chain framework sequence set forth in a sequence selected from the group consisting of: SEQ ID NO:25, SEQ ID NO:26 and SEQ ID NO:27. Each possibility represents a separate embodiment of the present invention.

In some embodiments, the monoclonal antibody comprises a light chain framework sequences set forth in a sequence selected from the group consisting of: SEQ ID NO:11; SEQ ID NO:24; SEQ ID NO:25, SEQ ID NO:26 and SEQ ID NO:27; and SEQ ID NO:14. Each possibility represents a separate embodiment of the present invention.

In some embodiments, the monoclonal antibody comprises the light chain variable region sequence set forth in a sequence selected from the group consisting of: SEQ ID NO:33, SEQ ID NO:34 and SEQ ID NO:35. Each possibility represents a separate embodiment of the present invention. In some specific embodiments, the monoclonal antibody comprises the light chain variable region sequence set forth in SEQ ID NO:34.

In certain embodiments, the monoclonal antibody comprises: (i) the heavy chain framework sequences set forth in: SEQ ID NO:7 or SEQ ID NO:15; SEQ ID NO:16 or SEQ ID NO:17; SEQ ID NO:18, SEQ ID NO:19, SEQ ID NO:20, SEQ ID NO:21 or SEQ ID NO:22; and SEQ ID NO:10 or SEQ ID NO:23, and (ii) the light chain framework sequences set forth in: SEQ ID NO:11; SEQ ID NO:24; SEQ ID NO:25, SEQ ID NO:26 or SEQ ID NO:27; and SEQ ID NO:14. Each possibility represents a separate embodiment of the present invention.

In some embodiments, the monoclonal antibody comprises a heavy chain variable region sequence set forth in SEQ ID NO:28, SEQ ID NO:29, SEQ ID NO:30, SEQ ID NO:31 or SEQ ID NO:32; and a light chain variable region sequence set forth in SEQ ID NO:33, SEQ ID NO:34 or SEQ ID NO:35. Each possibility represents a separate embodiment of the present invention. In some embodiments, the monoclonal antibody comprises the heavy chain variable region sequence set forth in SEQ ID NO:32, and the light chain variable region sequence set forth in SEQ ID NO:34.

In some embodiments, the monoclonal antibody comprises the heavy chain variable region sequence set forth in SEQ ID NO:28, and the light chain variable region sequence set forth in SEQ ID NO:33. In some embodiments, the monoclonal antibody comprises the heavy chain variable region sequence set forth in SEQ ID NO:29, and the light chain variable region sequence set forth in SEQ ID NO:33. In some embodiments, the monoclonal antibody comprises the heavy chain variable region sequence set forth in SEQ ID NO:30, and the light chain variable region sequence set forth in SEQ ID NO:33. In some embodiments, the monoclonal antibody comprises the heavy chain variable region sequence set forth in SEQ ID NO:31, and the light chain variable region sequence set forth in SEQ ID NO:33. In some embodiments, the monoclonal antibody comprises the heavy chain variable region sequence set forth in SEQ ID NO:32, and the light chain variable region sequence set forth in SEQ ID NO:33.

In some embodiments, the monoclonal antibody comprises the heavy chain variable region sequence set forth in SEQ ID NO:28, and the light chain variable region sequence set forth in SEQ ID NO:34. In some embodiments, the monoclonal antibody comprises the heavy chain variable region sequence set forth in SEQ ID NO:29, and the light chain variable region sequence set forth in SEQ ID NO:34. In some embodiments, the monoclonal antibody comprises the heavy chain variable region sequence set forth in SEQ ID NO:30, and the light chain variable region sequence set forth in SEQ ID NO:34. In some embodiments, the monoclonal antibody comprises the heavy chain variable region sequence set forth in SEQ ID NO:31, and the light chain variable region sequence set forth in SEQ ID NO:34.

In some embodiments, the monoclonal antibody comprises the heavy chain variable region sequence set forth in SEQ ID NO:28, and the light chain variable region sequence set forth in SEQ ID NO:35. In some embodiments, the monoclonal antibody comprises the heavy chain variable region sequence set forth in SEQ ID NO:29, and the light chain variable region sequence set forth in SEQ ID NO:35. In some embodiments, the monoclonal antibody comprises the heavy chain variable region sequence set forth in SEQ ID NO:30, and the light chain variable region sequence set forth in SEQ ID NO:35. In some embodiments, the monoclonal antibody comprises the heavy chain variable region sequence set forth in SEQ ID NO:31, and the light chain variable region sequence set forth in SEQ ID NO:35. In some embodiments, the monoclonal antibody comprises the heavy chain variable region sequence set forth in SEQ ID NO:32, and the light chain variable region sequence set forth in SEQ ID NO:35.

According to some embodiments, the humanized mAb heavy chain is selected from IgG4 and IgG1 isotype. According to some embodiments, the humanized mAb heavy chain is IgG4 isotype. According to some embodiments, the humanized mAb light chain is kappa isotype. According to some specific embodiments, the humanized mAb comprises a light chain kappa isotype and a heavy chain IgG4 isotype. According to other specific embodiments, the humanized mAb comprises a light chain kappa isotype and a heavy chain IgG1 isotype.

According to some embodiments, the mAb comprises a light chain set forth in SEQ ID NO:52. According to some embodiments, the mAb comprises a heavy chain set forth in SEQ ID NO:53 or SEQ ID NO:59. According to some embodiments, the mAb comprises a light chain set forth in SEQ ID NO: 52 and a heavy chain set forth in SEQ ID NO: 53. According to some embodiments, the mAb comprises a light chain set forth in SEQ ID NO: 52 and a heavy chain set forth in SEQ ID NO: 59.

According to some embodiments, the mAb comprises a light chain variable region set forth in SEQ ID NO: 58 and a heavy chain set forth in SEQ ID NO: 53. According to some embodiments, the mAb comprises a light chain variable region set forth in SEQ ID NO: 58 and a heavy chain set forth in SEQ ID NO: 59. According to some embodiments, the mAb comprises a light chain set forth in SEQ ID NO: 52 and a heavy chain variable region set forth in SEQ ID NO: 57.

The present invention also provides a mAb comprising a light chain variable region set forth in SEQ ID NO: 58 and a heavy chain variable region set forth in SEQ ID NO: 57.

In some embodiments, the humanized mAb or antigen-binding fragment thereof is capable of binding with an affinity of at least about $10^{-8}$M to a human CEACAM1 protein. In some embodiments, the humanized mAb or antigen-binding fragment thereof is capable of binding with an affinity of at least about $5 \times 10^{-7}$M to at least one of a human CEACAM3 and human CEACAM5 protein.

The present invention further provides, in another aspect, analogs and/or derivatives of the monoclonal antibody described above, having at least 90% sequence identity with the antigen-binding fragment of said monoclonal antibody.

Fragments of mAbs which recognize CEACAM1, comprising at least an antigen-binding domain, are also included within the scope of the present invention as long as they comprise the above-defined CDR sequences and at least one back-mutation of a human sequence to a murine sequence.

The present invention further provides, in another aspect, isolated polynucleotides encoding a monoclonal antibody described above or a fragment thereof, which specifically recognizes human CEACAM1.

In some embodiments, the isolated polynucleotide sequence comprises a DNA sequences set forth in any one of SEQ ID NOs:44 to 51 encoding a humanized mAb variable region, or analogs thereof having at least 90% sequence identity with said sequences. In some embodiments, the isolated polynucleotide sequence comprises a DNA sequences set forth in SEQ ID NO:54 or SEQ ID NO:55 encoding a humanized mAb heavy chain, or analogs thereof having at least 90% sequence identity with said sequences. In some embodiments, the isolated polynucleotide sequence comprises a DNA sequence set forth in SEQ ID NO:56 encoding a humanized mAb light chain, or analogs thereof having at least 90% sequence identity with said sequences.

The present invention further provides, in another aspect, a plasmid comprising the isolated polynucleotide described above.

The present invention further provides, in another aspect, a pharmaceutical composition comprising a therapeutically effective amount of the monoclonal antibody described above, and a pharmaceutically acceptable carrier, diluent or excipient.

According to some embodiments, the pharmaceutical composition comprises 1-50 mg/ml of humanized mAb to CEACAM1. According to some embodiments, the pharmaceutical composition comprises a basic amino acid. According to some embodiments, the pharmaceutical composition comprises a sugar. According to some embodiments, the pharmaceutical composition comprises a surfactant. According to some embodiments, the pharmaceutical composition comprises a basic amino acid, a sugar and a surfactant. According to some embodiments, the pharmaceutical composition comprises (i) 1-10 mg/ml of basic amino acid; (ii) 10/100 mg/ml of a sugar; (iii) 0.01-1 mg/ml of a surfactant; (iv) 1-50 mg/ml of humanized mAb to CEACAM1, 4-6 mg/ml of basic amino acid, 70-100 mg/ml of a sugar and a 0.1-1 mg/ml of non-anionic surfactant; or (v) 10 mg/ml of humanized mAb to CEACAM1, 4.65 mg/ml of L-Histidine, 82 mg/ml of sucrose and 0.20 mg/ml of polysorbate 20

According to some embodiments, the basic amino acid is selected from the group consisting of: Histidine, Arginine, Lysine and Ornitine. Each possibility represents a separate embodiment of the present invention. According to some embodiments, the composition comprises 1-10, 2-9, 3-7 or 4-6 mg/ml of basic amino acid. Each possibility represents a separate embodiment of the present invention.

According to some embodiments, the sugar is selected from the group consisting of: sucrose, trehalose, glucose, dextrose and maltose. Each possibility represents a separate embodiment of the present invention. According to some embodiments, the composition comprises 10-200, 10-100, 50-150 or 70-100 mg/ml of sugar. Each possibility represents a separate embodiment of the present invention.

According to yet other embodiments, the composition comprises polyol, including but not limited to mannitol and sorbitol. Each possibility represents a separate embodiment of the present invention.

According to some embodiments, the surfactant is a non-anionic. According to some embodiments, the surfactant selected from the group consisting of: polysorbates, sorbitan esters and poloxamers. Each possibility represents a separate embodiment of the present invention. According to some embodiments, the surfactant selected from the group consisting of: polysorbate 20, polysorbate 80. Each possibility represents a separate embodiment of the present invention. According to some embodiments, the composition comprises 0.01-10, 0.01-1, 0.05-5 or 0.1-1 mg/ml of surfactant. Each possibility represents a separate embodiment of the present invention. According to some embodiments, the pharmaceutical composition comprises 4-6 mg/ml of basic amino acid, 70-100 mg/ml of a sugar and a 0.1-1 mg/ml of surfactant.

According to some embodiments, the pharmaceutical composition is in a liquid form and comprises 1-50 mg/ml of humanized mAb to CEACAM1 comprising at least one back-mutation to a murine sequence. According to other embodiments, the pharmaceutical composition is lyophilized. According to some embodiments, the pharmaceutical composition comprises: 10 mg/ml of humanized mAb to CEACAM1, 4.65 mg/ml of L-Histidine, 82 mg/ml of sucrose and 0.20 mg/ml of polysorbate 20.

According to some embodiments, the pharmaceutical composition comprises at least one humanized mAb or fragment defined above and an additional immuno-modulator or a kinase inhibitor. According to some embodiments, a pharmaceutical composition comprising at least one humanized mAb or fragment defined above, and a pharmaceutical composition comprising an additional immuno-modulator or a kinase inhibitor, are used in treatment of cancer by separate administration.

According to some specific embodiments, the additional immuno-modulator is selected from the group consisting of: an anti-human programmed cell death protein 1 (PD-1), PD-L1 and PD-L2 antibody, an activated cytotoxic lymphocyte cell, a lymphocyte activating agent, and a RAF/MEK pathway inhibitor. Each possibility represents a separate embodiment of the present invention. According to some specific embodiments, the additional immuno-modulator is selected from the group consisting of: mAb to PD-1, mAb to PD-L1, mAb to PD-L2, Interleukin 2 (IL-2), lymphokine-activated killer (LAK) cell.

According to some embodiments, the invention provides a pharmaceutical composition comprising a humanized mAb containing back-mutations, as defined above or an antigen-binding fragment thereof, and a pharmaceutical composition comprising a mAb to at least one of human programmed cell death protein 1 (PD-1), PD-L1 and PD-L2 or an antigen-binding fragment thereof, for use in treatment of cancer by separate administration.

According to other embodiments a pharmaceutical composition is provided comprising a humanized mAb to CEACAM defined above or an antigen-binding fragment thereof, and an activated, cytotoxic lymphocyte cell. In certain embodiments, the activated, cytotoxic lymphocyte cell is selected from the group consisting of a LAK cell, a CIK cell, and any combination thereof. Each possibility represents a separate embodiment of the invention. In certain embodiments, the activated, cytotoxic lymphocyte cell is a lymphokine-activated killer (LAK) cell.

In other embodiments, the pharmaceutical composition comprises a humanized mAb to CEACAM1 or an antigen-binding fragment thereof, and a lymphocyte activating agent or a fragment, analog or fusion protein thereof. In certain embodiments, the lymphocyte activating agent is selected from the group consisting of IL-2, IFNγ, an anti-CD3 antibody and fragments, analogs or fusion proteins thereof. In certain embodiments, the lymphocyte activating agent is IL-2 or a fragment, analog or fusion protein thereof. Each possibility represents a separate embodiment of the invention.

In yet other embodiments, the pharmaceutical composition comprises an inhibitor of a kinase selected from the group consisting of a B-Raf kinase mutant, a MEK1 kinase and a MEK2 kinase, and a humanized mAb to human CEACAM1 defined above or an antigen-binding fragment thereof.

According to some specific embodiments, the B-Raf kinase inhibitor attenuates or prevents the phosphorylation of MEK1 or MEK2 by the B-Raf kinase mutant. In certain embodiments, the B-Raf kinase inhibitor attenuates or prevents the dimerization of the B-Raf kinase mutant. In certain embodiments, the MEK1 kinase inhibitor attenuates or prevents the phosphorylation of MAPK by the MEK1 kinase. In certain embodiments, the MEK2 kinase inhibitor attenuates or prevents the phosphorylation of MAPK by the MEK2 kinase.

The present invention further provides, according to other embodiments, an inhibitor of a kinase selected from the group consisting of a B-Raf kinase mutant, a MEK1 kinase and a MEK2 kinase, and a humanized mAb to human CEACAM1 or an antigen-binding fragment thereof, for use in treating cancer. The two active ingredients may be part of one or separate pharmaceutical compositions which can be administered simultaneously or by separate administrations.

The humanized mAb to CEACAM1 according to the present invention and the additional immuno-modulator may be contained in one pharmaceutical composition or in separate compositions for simultaneous or separate administration.

In some embodiments, the pharmaceutical composition is for treatment of a disease or disorder associated with expression, activation or function of a CEACAM protein family member, including but not limited to CEACAM1. Each possibility represents a separate embodiment of the present invention.

In some embodiments, the pharmaceutical composition is for treatment of a disease or disorder associated with CEACAM1 expression, activation or function. In some embodiments, the disease or disorder is a cell proliferative disease or disorder. Each possibility represents a separate embodiment of the present invention. In some embodiments, the cell proliferative disease or disorder is a cancer.

According to some embodiments the cancer is selected from the group consisting of: melanoma, colorectal, bladder, lung, non-small cell lung carcinoma (NSCLC), non-small cell lung adenocarcinoma (NSCLA), gastrointestinal, pancreatic, breast, prostate, thyroid, stomach, ovarian, myeloma and uterine cancer. Each possibility represents a separate embodiment of the present invention.

The present invention further provides, in another aspect, a diagnostic composition comprising at least one humanized mAb or a fragment thereof, which specifically recognizes human CEACAM1, as described above.

The present invention further provides, in another aspect, a method of preventing, attenuating or treating a disease or disorder associated with expression, activation or function of a CEACAM1 protein, comprising administering to a subject in need thereof a therapeutically effective amount of the pharmaceutical composition described above.

In some embodiments, the disease or disorder is a cancer. In some embodiments, the disease or disorder is an infection, for example a viral infection.

In some embodiments, the isolated antibody contained in the pharmaceutical composition is attached to a cytotoxic moiety.

In certain embodiments, the method described above comprises administering to the subject at least one dose of a humanized mAb to CEACAM1 ranging from 0.01 mg/kg to 10 mg/kg body weight. In certain embodiments, the method described above comprises administering (i) multiple, identical or different, doses of humanized mAb; (ii) multiple escalating doses; or (iii) the pharmaceutical composition once every week, one every 2 weeks, once every 3 weeks, once every 4 weeks, or once every 5 weeks. In certain embodiments, the method described above comprises 1-10 administration cycles, each cycle comprising 2-5 infusions every 1-4 weeks, with a humanized mAb, followed by a 2-8 weeks between each cycle.

In certain embodiments, the method described above further comprises administering a lymphocyte cell or a plurality of lymphocyte cells. In some embodiments, the method described above further comprises administering to the subject CEACAM1-expressing lymphocytes. In some embodiments, the lymphocytes comprise T cells, NK cells or Tumor Infiltrating Lymphocytes (TILs). Each possibility represents a separate embodiment of the present invention. In some embodiments, the lymphocyte cell expresses CEACAM1, PD-1, or both. Each possibility represents a separate embodiment of the present invention. In certain such embodiments, the lymphocyte cell expresses CEACAM1 and PD-1. In some embodiments, the lymphocyte cell is selected from the group consisting of a tumor-infiltrating-lymphocyte (TIL) cell, a lymphokine-activated killer (LAK) cell, a cytokine induced killer (CIK) cell, a T cell, a B cell, an NK cell, and any combination thereof. Each possibility represents a separate embodiment of the present invention. In certain such embodiments, the lymphocyte cell is selected from the group consisting of a tumor-infiltrating-lymphocyte (TIL) cell and a lymphokine-activated killer (LAK) cell. In certain such embodiments, the lymphocyte cell is a tumor-infiltrating-lymphocyte (TIL) cell or a plurality of TIL cells. In certain such embodiments, the lymphocyte cell is a lymphokine-activated killer (LAK) cell or a plurality of LAK cells. In certain embodiments, the lymphocyte cell is activated. In some embodiments, the lymphocyte cell is cytotoxic to a cancer cell. In some embodiments, the cancer cell expresses CEACAM1, PD-L1, PD-L2, or any combination thereof. Each possibility represents a separate embodiment of the present invention. In some embodiments, the cancer cell expresses CEACAM1, PD-L1, or both. Each possibility represents a separate embodiment of the present invention. In some embodiments, the cancer cell expresses CEACAM1, PD-L2, or both. Each possibility represents a separate embodiment of the present invention. In certain such embodiments, the cancer cell expresses CEACAM1 and PD-L1 and PD-L2.

In certain embodiments, the methods described above further comprise administering to the subject a lymphocyte activating agent. According to some embodiments, the lymphocyte activating agent is selected from the group consisting of IL-2, IFNγ, and an anti-CD3 antibody. In certain embodiments, the methods described above further comprise administering to the subject an additional anti-cancer composition.

The present invention further provides, in another aspect, a method of immunomodulation, the method comprising contacting a CEACAM1-expressing lymphocyte with the antibodies or fragments thereof described above.

The present invention further provides, in another aspect, a method of inhibiting migration of a CEACAM1-expressing tumor cell, the method comprising contacting said CEACAM1-expressing tumor cell with the antibodies or fragments thereof described above, thereby inhibiting migration of said CEACAM-expressing tumor cell.

The present invention further provides, in another aspect, a method of inhibiting CEACAM1 homotypic or heterotypic protein-protein interaction, the method comprising contacting a CEACAM1-expressing lymphocyte with the antibodies or fragments thereof described above, thereby inhibiting CEACAM1 homotypic or heterotypic protein-protein interaction.

The present invention further provides, in another aspect, a method for increasing the duration or progression of response or survival of a subject having cancer, comprising administering to the subject effective amounts of a composition comprising a monoclonal antibody as described above, and an anti-neoplastic composition, wherein said anti-neoplastic composition comprises at least one chemotherapeutic agent, whereby the co-administration of the antibody and the anti-neoplastic composition effectively increases the duration or progression of survival.

The method of the present invention may comprise administering a pharmaceutical composition defined above together with additional anti-cancer composition. According to a specific embodiment the anti-cancer composition comprises at least one chemotherapeutic agent. According to other specific embodiments, the anti-cancer composition comprises an immuno-modulatory agent. The anti-cancer agent, which could be administered together with the antibody according to the present invention, or separately, may comprise any such agent known in the art exhibiting anti-cancer activity.

According to some embodiments, a method of treating cancer is provided comprising administering to a subject in need thereof a pharmaceutical composition comprising a humanized antibody which recognizes CEACAM1 and comprises back-mutations to a murine sequence, and a pharmaceutical composition comprising an additional immuno-modulator or a kinase inhibitor.

According to some embodiments, the immuno-modulator is selected from the group consisting of: mAb to PD-1, mAb to PD-L1, mAb to PD-L2, Interleukin 2 (IL-2), lymphokine-activated killer (LAK) cell and the kinase inhibitor is a B-Raf/MEK inhibitor.

In some embodiments the method comprises administration of two or more pharmaceutical compositions. In some embodiments, the administration of two or more of the pharmaceutical compositions is done simultaneously. In some embodiments of the method, the administration of two or more of the pharmaceutical compositions is done sequentially. In some embodiments of the method, the additional immuno-modulator is administered before the humanized mAb to human CEACAM1 or the antigen-binding fragment thereof. In some embodiments of the method, the immuno-modulator is administered simultaneously with the mAb to human CEACAM1 or the antigen-binding fragment thereof. In some embodiments of the method, the immuno-modulator is administered after the humanized mAb to human CEACAM1 or the antigen-binding fragment thereof.

In some embodiments, the method comprises administering to said patient a pharmaceutical composition comprising a monoclonal antibody to human CEACAM1 or an antigen-binding fragment thereof, and a pharmaceutical composition comprising a monoclonal antibody to human PD-1 or an antigen-binding fragment thereof. Each possibility represents a separate embodiment of the present invention.

According to yet other embodiments, the methods described above of treating a patient having cancer, comprises the step of administering to the patient a pharmaceutical composition comprising an inhibitor of a kinase selected from the group consisting of B-Raf kinase mutant, a MEK1 kinase and a MEK2 kinase, and a pharmaceutical composition comprising a monoclonal antibody to human CEACAM1 or an antigen-binding fragment thereof, wherein the cancer cells express a B-Raf kinase mutant, thereby treating the cancer.

In some embodiments, the methods described above for treating cancer further comprises the step of administering to said patient a pharmaceutical composition comprising a lymphocyte cell. In some embodiments, the administration of the pharmaceutical composition comprising a lymphocyte cell is done simultaneously with at least one of the pharmaceutical compositions comprising antibodies. In some embodiments of the method, the administration of the two or more pharmaceutical compositions is done sequentially.

In some embodiments, the lymphocyte cell is pre-incubated with a humanized mAb to human CEACAM1, with an antigen-binding fragment thereof or with the additional immuno-modulator. Each possibility represents a separate embodiment of the present invention.

A pharmaceutical composition according to the present invention may be administered by any suitable means, such as intranasally, subcutaneously, intramuscularly, intravenously, intra-arterially, intraarticularly, intralesionally orally, or topically. According to some embodiments, the pharmaceutical composition is administered parenterally. According to some specific embodiments, intravenous (i.v.), administration is utilized.

A method according to the present invention, of treating cancer or other CEACAM1-associated disease or disorder, comprises according to some embodiments, administering to a subject in need thereof at least one dose of a humanized mAb to CEACAM1 ranging from 0.01 mg/kg to 10 mg/kg body weight.

According to some embodiments, the at least one dose is selected from the group consisting of: 0.01-0.1 mg/kg; 0.1-1 mg/kg; 1-10 mg/kg; and 10-50 mg/kg.

According to some embodiments, the method comprises administering of multiple doses of humanized mAb, wherein the multiple doses are identical or different. According to some embodiments, the method comprises administering multiple escalating doses. According to some embodiments, the method comprises at least one cycle of administration for at least 12 weeks.

According to other embodiments the treatment duration is 12-50 weeks. According to some specific embodiments the treatment duration is selected from the group consisting of: 12-20 weeks, 20-30 weeks and 30-50 weeks. According to yet other embodiments, the treatment regimen comprises several administration cycles each for at least 12 weeks.

According to some embodiments, the treatment regimen comprises 1-8 cycles, each cycle comprises 4 infusions of the humanized anti CEACAM mAb for a duration of at least 4 weeks. According to some embodiments the treatment regimen comprises 2-6 cycles.

According to some embodiments, administration is once every week, one every 2 weeks, once every 3 weeks, once every 4 weeks, or once every 5 weeks. Each possibility represents a separate embodiment of the present invention.

According to some embodiments, a treatment regimen comprises 1-10 cycles, each cycle comprising 2-5 infusions every 1-4 weeks, with a humanized mAb according to the invention, followed by a 2-8 weeks between each cycle.

According to some embodiments a dose escalation regimen is provided comprising administration starting with 0.01 mg/kg, and continuing to 0.03 mg/kg, 0.1 mg/kg, 0.3 mg/kg, 1 mg/kg, 3 mg/kg, and 10 mg/kg. According to yet other embodiments, the treatment regimen comprises 6 cycles of 4 infusions each administered every 2 weeks.

The present invention further provides, in another aspect, a method for diagnosing a cancer in a subject in need thereof, the method comprising contacting a biological sample derived or obtained from said subject with the diagnostic composition described above, wherein a complex formation beyond a predetermined threshold is indicative of the cancer in said subject.

The present invention further provides, in another aspect, a method for determining the expression of CEACAM1, the method comprising contacting a biological sample with the antibodies or fragments thereof described above, and measuring the level of immune complex formation. According to some embodiments, the method comprises comparing said level of immune complex to a standard curve obtained from known amounts of CEACAM1.

The present invention further provides, in another aspect, a method for diagnosing a disease or disorder associated with a CEACAM protein expression, comprising the steps of incubating a biological sample with a monoclonal antibody as described above; detecting the bound CEACAM protein using a detectable probe; comparing the amount of bound CEACAM protein to a standard curve obtained from reference samples containing known amounts of CEACAM protein; calculating the amount of the CEACAM protein in the biological sample from the standard curve; and comparing the amount of CEACAM protein to a normal CEACAM protein amount.

According to some embodiments, a humanized mAb according to the invention is used as a predictive biomarker associated with anti CEACAM1 treatment, based on levels of expression of CEACAM1 in tumor specimens prior to treatment. The expression of CEACAM1 levels is determined using methods known in the art utilizing a humanized mAb according to the invention.

The present invention further provides, in an aspect, the use of a monoclonal antibody as described above, for diagnosis, prevention or treatment of a cell proliferative or angiogenesis-related disease or disorder or an infection.

The present invention further provides, in an aspect, the use of a monoclonal antibody as described above, for preparation of a medicament for treatment of a disorder or disease associated with expression or activation of a CEACAM protein.

The present invention further provides, in an aspect, the use of a monoclonal antibody as described above, for preparation of a diagnostic composition for the diagnosis of a cell proliferative or angiogenesis-related disease or disorder or an infection.

The present invention further provides, in an aspect, a partly-humanized monoclonal antibody, comprising a heavy-chain variable region comprising a framework amino-acid sequence set forth in SEQ ID NO:18, SEQ ID NO:19, SEQ ID NO:20, SEQ ID NO:21 or SEQ ID NO:22, or a light-chain variable region comprising a framework amino-acid sequence set forth in SEQ ID NO:25, SEQ ID NO:26 or SEQ ID NO:27.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

| No. | | | | | | | |
|---|---|---|---|---|---|---|---|
| 1 | 2 | 3 | 4 | 5 | 6 | 7 | 8 |
| $V_H/V_L$ VH1/VK1 | VH1/VK2 | VH1/VK3 | VH2/VK1 | VH2/VK2 | VH2/VK3 | VH3/VK1 | VH3/VK2 |

| No. | | | | | | | |
|---|---|---|---|---|---|---|---|
| 9 | 10 | 11 | 12 | 13 | 14 | 15 | 16 |
| $V_H/V_L$ VH3/VK3 | VH4/VK1 | VH4/VK2 | VH4/VK3 | VH5/VK1 | VH5/VK2 | VH5/VK3 | Chimeric IgG |

FIG. 3 is a graphic illustration of the results of recombinant human CEACAM-1 competition binding ELISA assays. Varying concentrations of purified humanized IgG antibody variants were competed against a constant concentration of biotinylated anti-CEACAM-1 IgG (chimeric CM-10 IgG1): (A) IgG1 Variants; and (B) IgG4 (S241P) variants. Bound, biotinylated chimeric CM-10 was detected using streptavidin HRP and TMB substrate.

Figure 4:
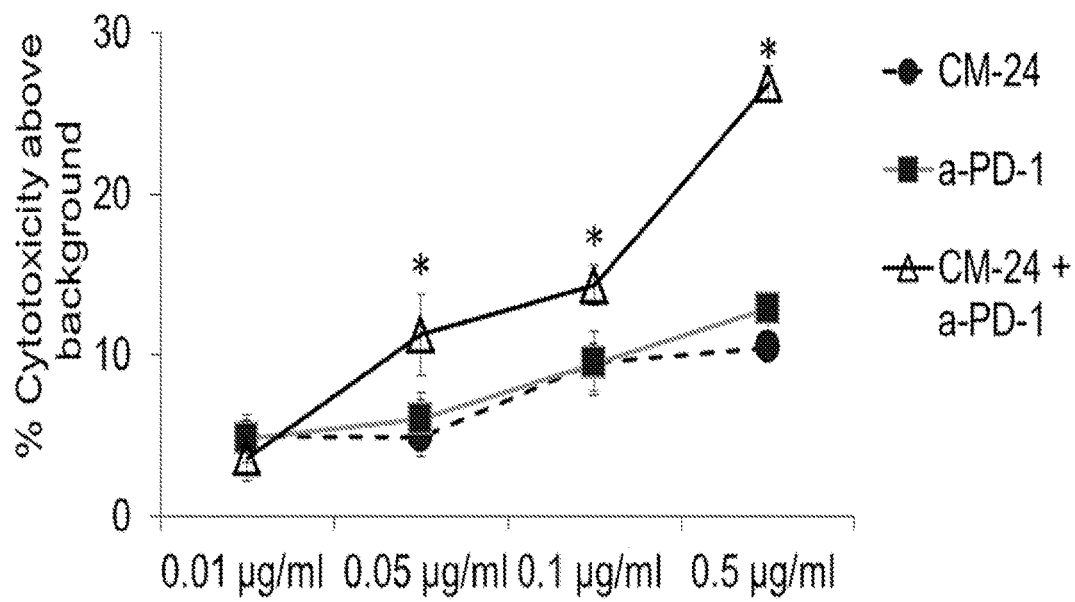

FIG. 4 represents synergistic effects of anti-CEACAM1 and anti-PD-1 antibodies on the cytotoxicity of human TIL cells against human melanoma cells. TIL cells were incubated with various concentrations of a humanized mAb to human CEACAM1 (dashed black line, sphere marker), a mAb to human PD-1 (solid gray line, rectangular marker) or a combination of both antibodies (solid black line, triangle marker). IFN-γ-treated melanoma cells were added for an overnight incubation. Results represent an average of % cytotoxicity±SE as determined by classical LDH release assay from triplicate wells per treatment. *P<0.05 paired T-test compared to the monoclonal antibody to human CEACAM1 only.

Figure 5A:
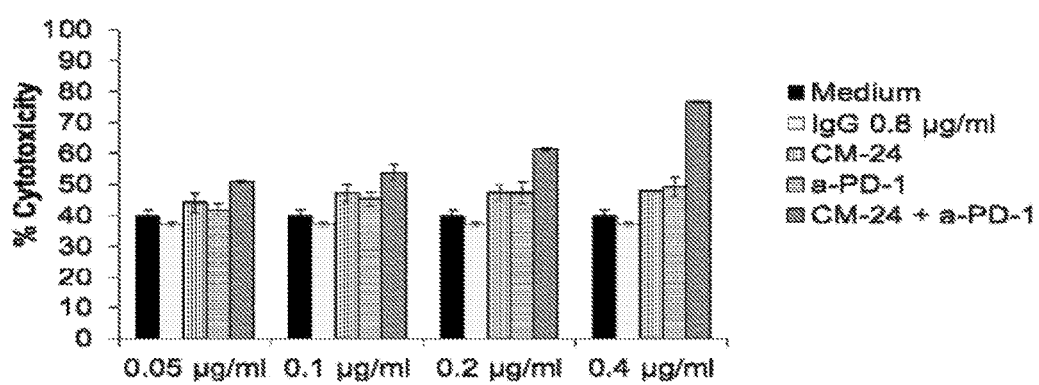
Figure 5B:
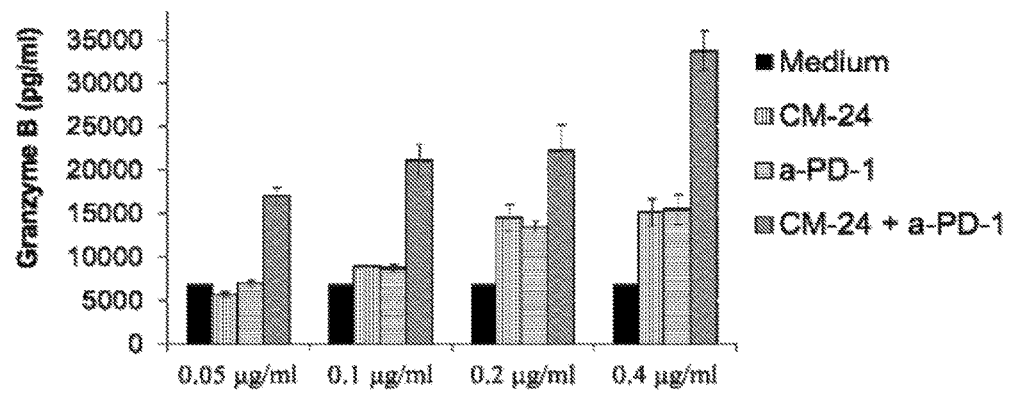

FIGS. 5A-B Synergistic effects of anti-CEACAM1 and anti-PD-1 antibodies on Granzyme B levels and the cytotoxicity of human TIL cells against human melanoma cells when anti-PD-1 antibodies are added prior to the addition of anti-CEACAM1 antibodies. Human melanoma cells were grown in the presence of IFN-d to induce PD-L1 expression. Human TIL cells were incubated with medium only (black), non-specific IgG antibody (white), various concentrations of a monoclonal antibody to human CEACAM1 (vertical lines), a monoclonal antibody to human PD-1 (horizontal lines) or a combination of both antibodies (dots). (A) Results represent an average of % cytotoxicity±SE as determined by classical LDH release assay from triplicate wells per treatment. *P≤0.05 paired T-test compared to a-PD-1 only. (B) Results represent Granzyme B levels±SE as determined by commercial Granzyme B ELISA kit from triplicate wells per treatment.

Figure 6:
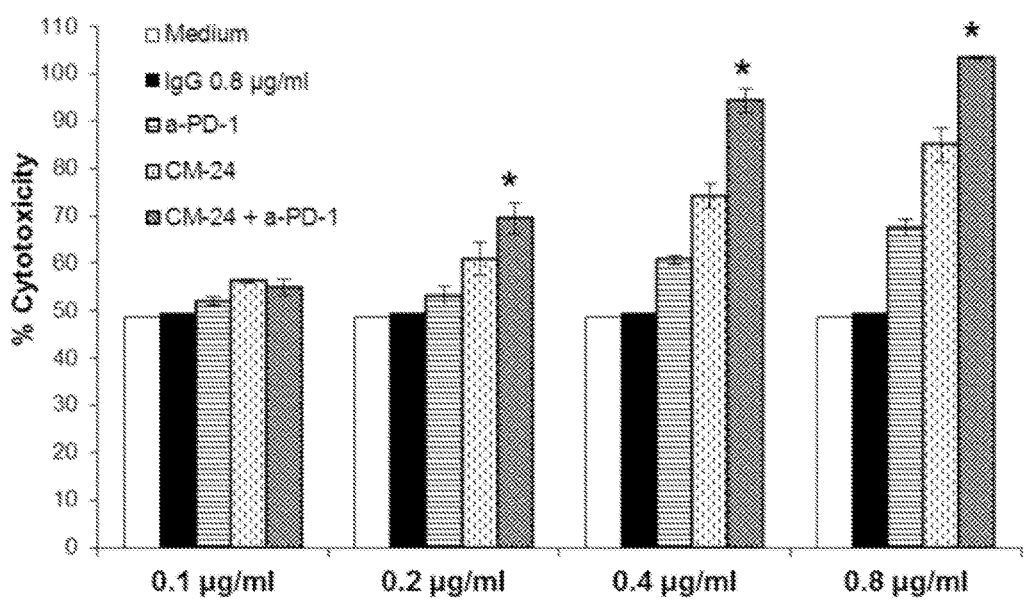

FIG. 6. Synergistic effects of anti-CEACAM1 and anti-PD-1 antibodies on the cytotoxicity of human LAK cells against human melanoma cells when anti-PD-1 antibodies are added prior to the addition of anti-CEACAM1 antibodies. Human melanoma cells were grown in the presence of IFN-d to induce PD-L1 expression. Human LAK cells generated by activation of PBMCs from a healthy human donor with IL-2 were incubated with medium only (white), non-specific IgG antibody (black), various concentrations of a monoclonal antibody to human CEACAM1 (vertical lines), a monoclonal antibody to human PD-L1 (horizontal lines) or a combination of both antibodies (dots). Results represent an average of % cytotoxicity±SE as determined by classical LDH release assay from triplicate wells per treatment. *P≤0.05 paired T-test compared to a-PD-L1 only. Combination index was calculated as described above.

Figure 7:
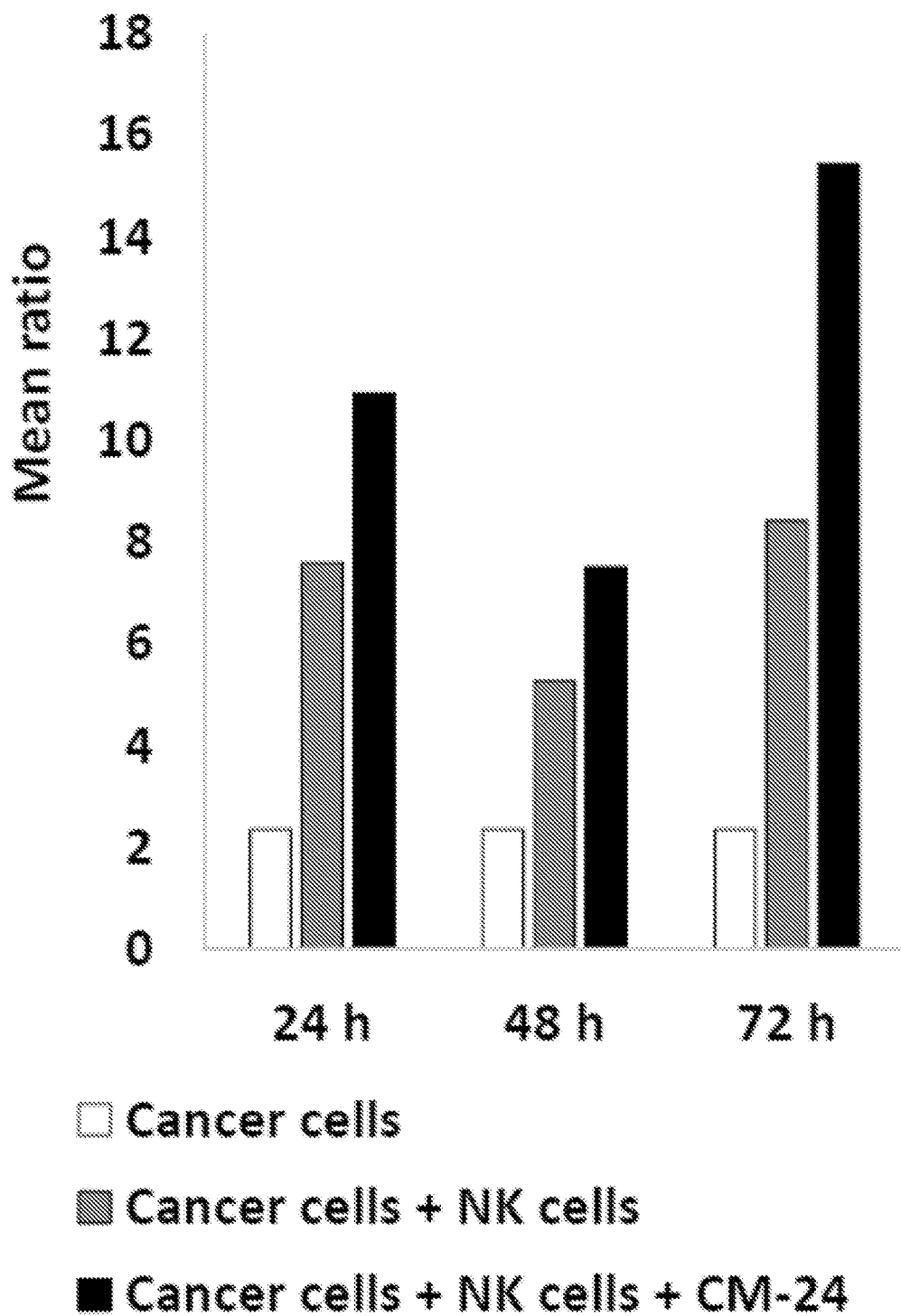

FIG. 7. Treatment with anti-CEACAM1 antibodies increases PD-L1 expression on target cancer cells. NK cells (NK92MI) were incubated with or without CM-24 (10 µg/ml), followed by the addition of human melanoma cells (SKMEL28). The cells were incubated for 24, 48 and 72 hours and PD-L1 levels were measured at each time point by FACS analysis. Mean ratio of anti-PD-L1 compared to an appropriate isotype control for the indicated treatments at the different time points.

Figure 8:
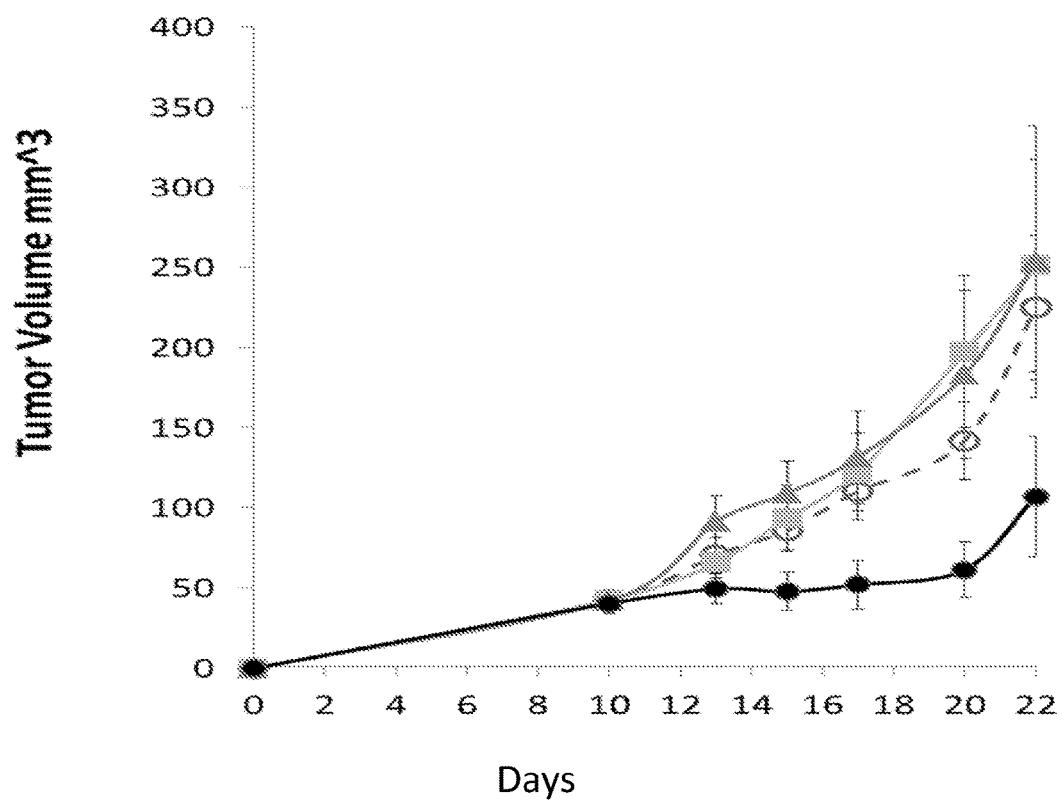

FIG. 8. Synergistic effects of anti-CEACAM1 and anti-PD-1 antibodies on tumor progression in immuno-competent mice. Murine lymphoma cells were implanted subcutaneously in the abdomen of BALB/C mice (Day 1). On days 10, 15 and 20, mice were intravenously administered with either PBS (dashed black line, empty circles), an anti-murine CEACAM1 antibody (solid gray line, gray rectangles), an anti-murine PD-1 antibody (solid gray line, gray triangles) or a combination of both antibodies (solid black line, black spheres).

Figure 9:
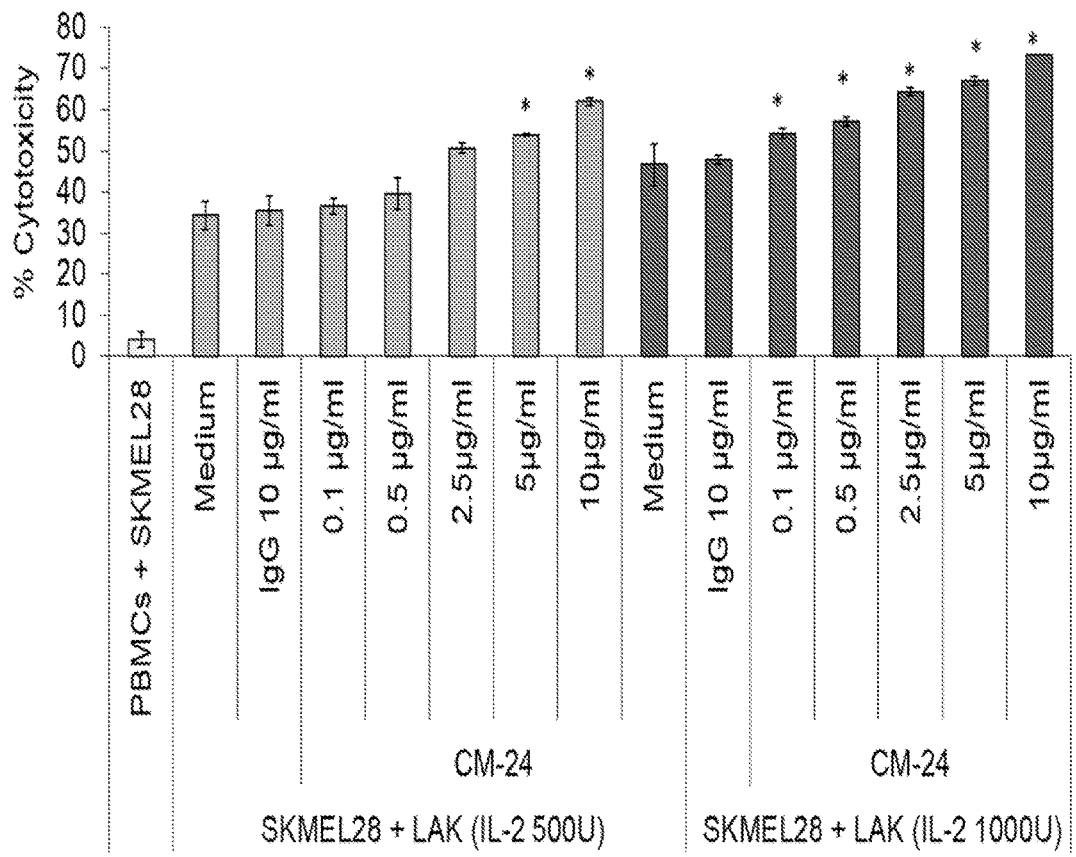

FIG. 9. Anti-CEACAM1 antibodies increase the cytotoxicity of human LAK cells against human melanoma cells. Human LAK cells were incubated with CM-24 in different concentrations for 30 minutes at 37° C. Human melanoma cancer cells (SKMEL28) were added for an incubation of 24 hours. Results represent an average of % cytotoxicity±SE as determined by classical LDH release assay from triplicate wells per treatment. *P<0.05 paired T-test compared to effectors+target cells with medium only.

Figure 10:
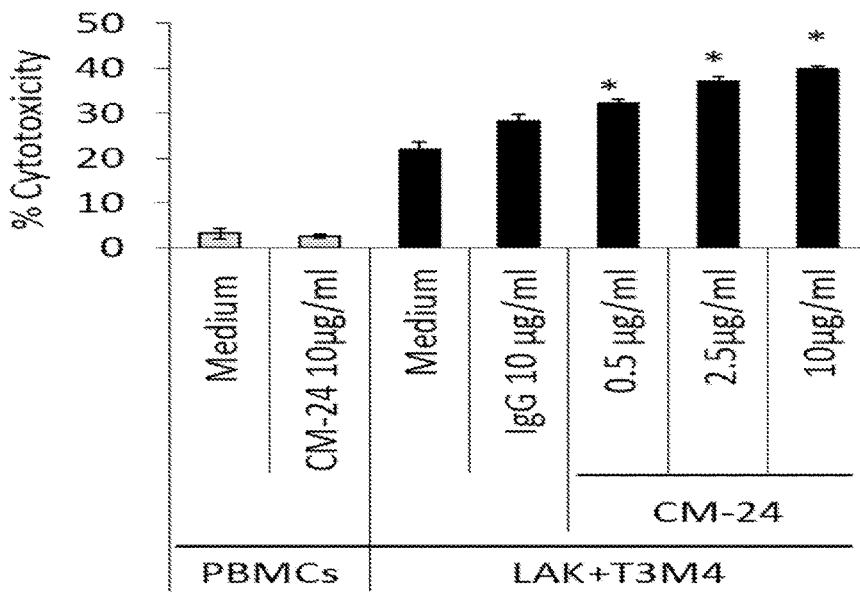

FIG. 10. Anti-CEACAM1 antibodies increase the cytotoxicity of human LAK cells against a human pancreatic cancer cells T3M4. Human LAK cells were incubated with CM-24 in different concentrations for 30 minutes at 37° C. Human pancreatic cancer cells T3M4 were added for an incubation of 24 hours. Results represent an average of % cytotoxicity±SE as determined by classical LDH release assay from triplicate wells per treatment. *P<0.05 paired T-test compared to effectors+target cells with medium only.

Figure 11A:
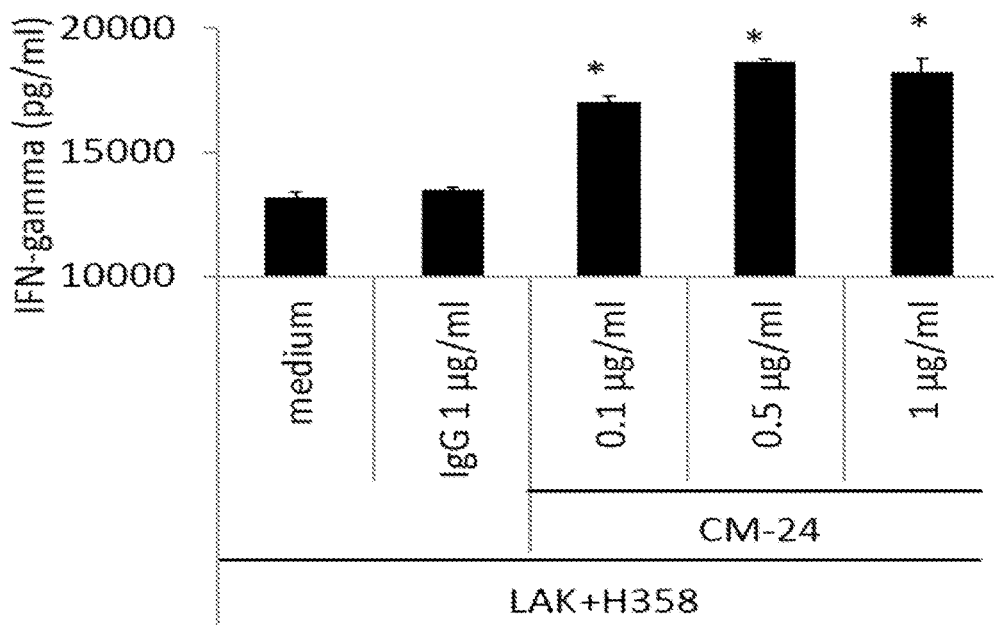
Figure 11B:
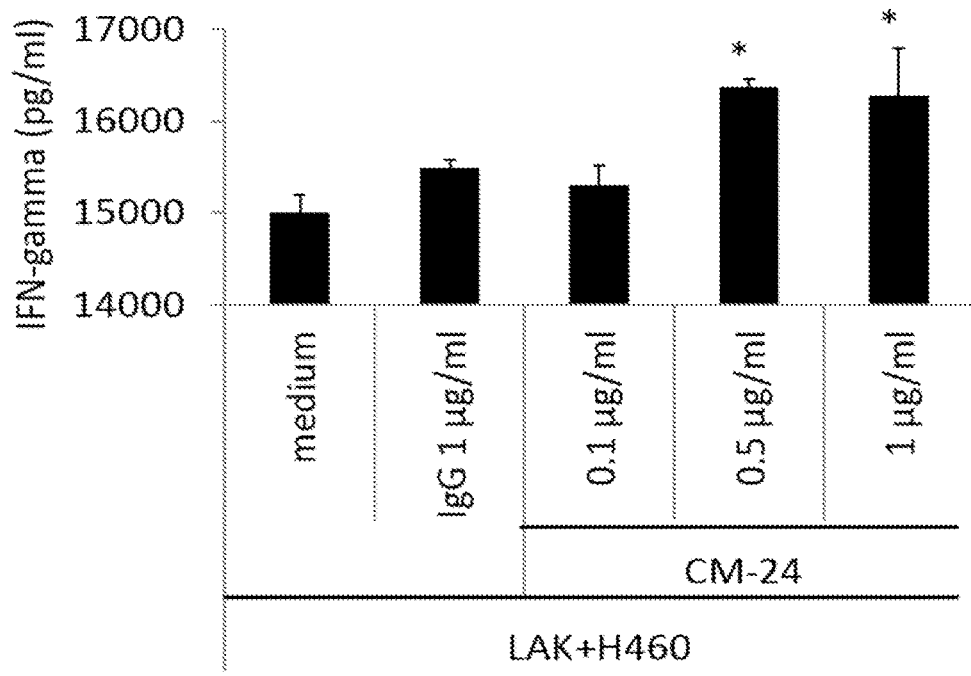

FIG. 11. Anti-CEACAM1 antibodies enhance IFN-γ secretion of human LAK cells in the presence of human cancer cells. Human LAK cells were incubated with CM-24 in different concentrations for 30 minutes at 37° C. Human lung cancer cells H358 (11A) or H460 (11B) were added for an incubation of 24 hours. IFN-γ secretion was measured by ELISA. Results represent the mean+S.E of Granzyme B release values from 3 repeats per treatment. *P<0.05 paired T-test, compared to effectors+target cells with medium only.

Figure 12A:
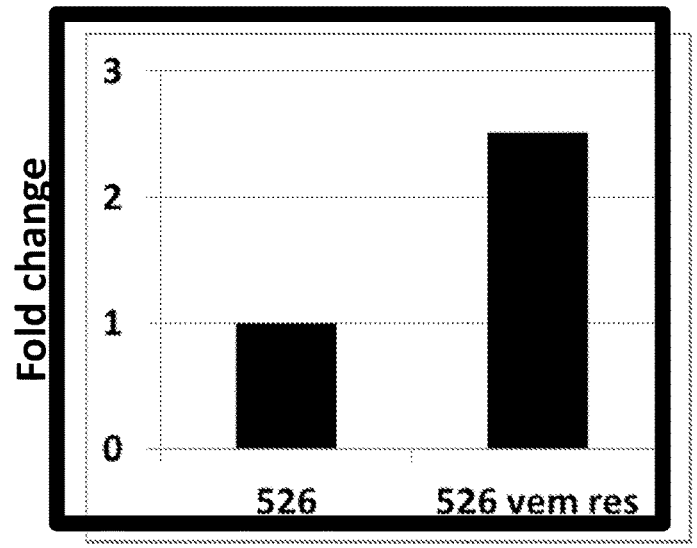
Figure 12B:
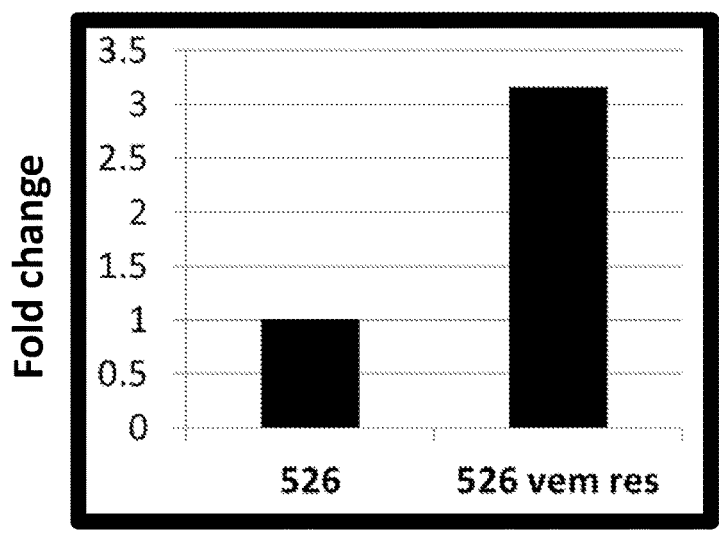

FIGS. 12A and 12B presents the correlation between expression of CEACAM1 types CEACAM1-long (A) and CEACAM1-short (B), and resistance to inhibitors of B-Raf mutants in cancer cells.

Figure 13A:
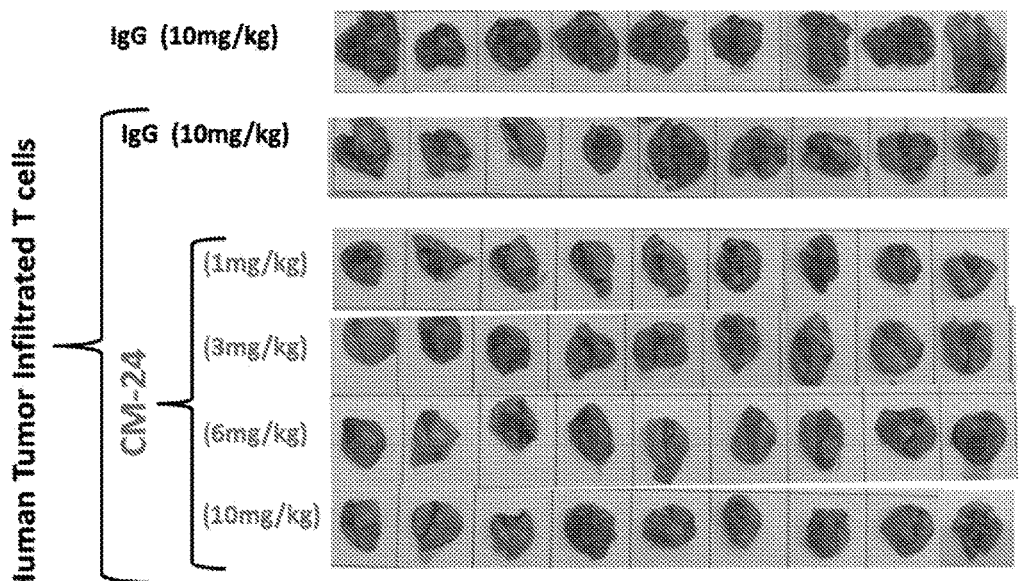
Figure 13B:
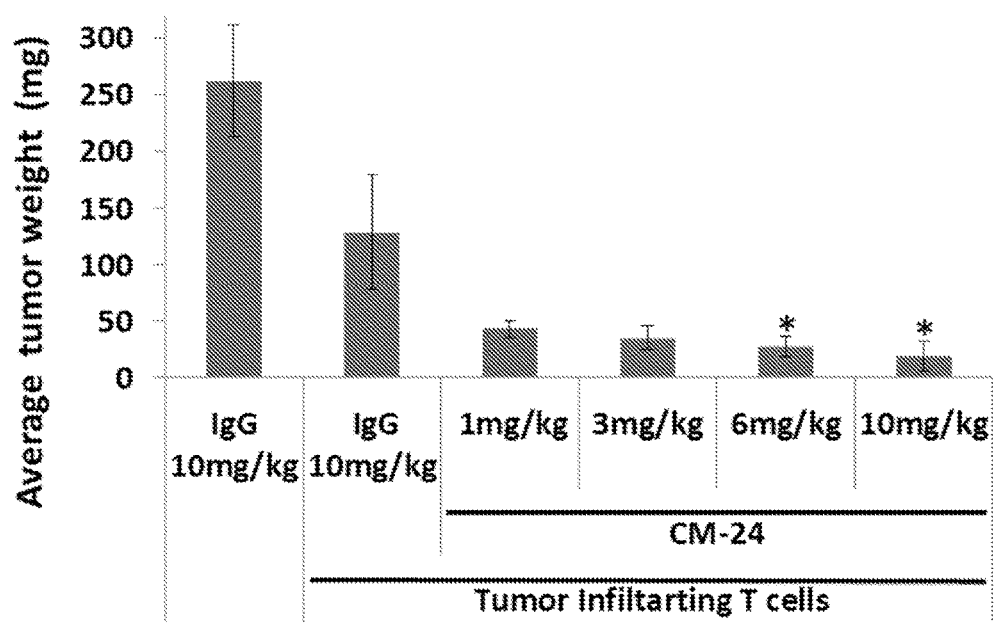
Figure 13C:
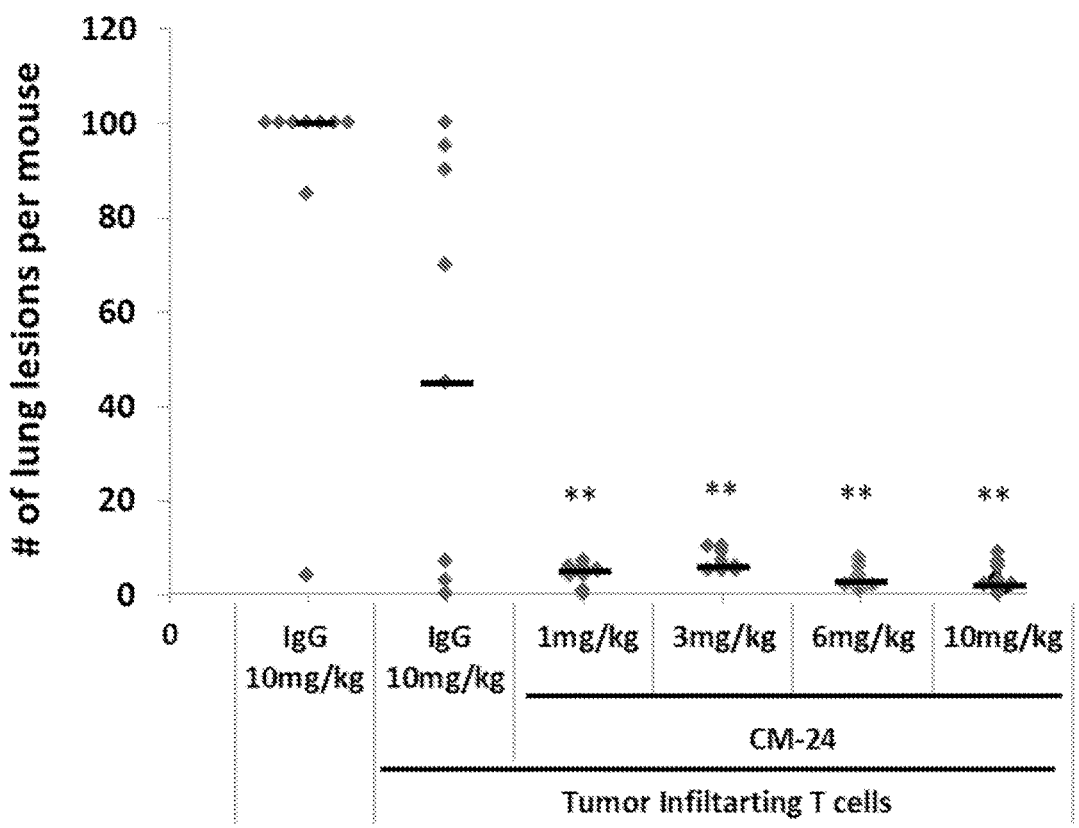

FIG. 13A presents pictograms of lungs removed from mice engrafted with melanoma cells and treated according to the treatment groups indicated in the figure; FIG. 13B presents the average tumor weight of each treatment group; and FIG. 13C presents the number of lesions per mouse of each treatment group.

Figure 14:
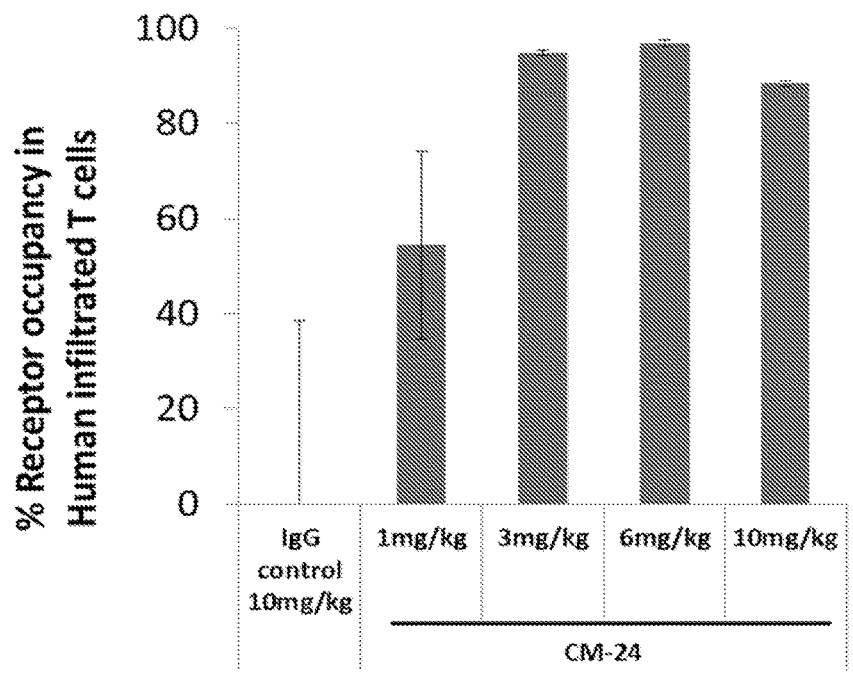

FIG. 14 is a bar histogram presenting the percentage of CEACAM1 receptor occupancy in TIL cells isolated from the lung lesions model.

FIGS. 15A and 15B represent the amino acid sequences of the light and heavy chain of the back-mutated humanized anti CEACAM1 mAb, denoted CM-24, currently in clinical trial. FIG. 15A contains the light chain sequence (SEQ ID NO: 52) wherein amino acid residues 1-107 are the variable region including CDRs and amino acid residues 108-214 (in bold) are kappa light chain constant region. FIG. 15B representing the heavy chain sequence (SEQ ID NO: 53), amino acid residues 1-120 are variable region, amino acid residues 121-447 (in bold) are IgG4 heavy chain constant region, and the predicted N-glycosylation site (Asparagine 297) is underlined. FIG. 15C representing the heavy chain sequence (SEQ ID NO: 59), amino acid residues 1-121 are variable region, amino acid residues 122-450 (in bold) are IgG1 heavy chain constant region, and the predicted N-glycosylation site (Asparagine 300) is underlined.

DETAILED DESCRIPTION OF THE INVENTION

The present invention discloses non-fully humanized monoclonal antibodies which recognize CEACAM1. Advantageously, the antibodies of the invention are almost fully humanized, thus avoiding the risk of adverse immune response towards the antibodies and are therefore safe for in-vivo use in humans. The antibodies of the invention are characterized by having unique CDR sequence and novel non-fully humanized framework sequences and design. The unique properties of the monoclonal antibodies of the present invention, broaden their therapeutic utility for treatment and diagnosis of additional types of malignancies and various infections. More specifically, the monoclonal antibodies provided by the present invention have specific combinations of CDRs and non-fully-humanized framework sequences, and possess unique properties and improved safety and potency over known non-human anti-CEACAM1 antibodies.

The unique properties of the antibodies provided by the present invention confer several advantages to the use of these antibodies in human, specifically in applications requiring long-term or repeated administration, when other, non-human antibodies cannot be administered in the fear of eliciting an immunogenic response towards the non-human antibodies themselves. Avoiding such an immune response becomes more crucial when the treated person is a patient inflicted with a disease, where further aggravating the patient's health should be avoided. The present invention yet further provides, in another aspect, a non-fully-humanized monoclonal antibody, comprising (i) a heavy-chain variable region comprising CDR1, CDR2 and CDR3 comprising the amino-acid sequences set forth in SEQ ID NO:1, SEQ ID NO:2 and SEQ ID NO:3, respectively, and a non-CDR (framework) amino-acid sequence that differs in 2 to 9 amino-acids from the amino-acid sequence set forth in SEQ ID NO:9; and/or (ii) a light-chain variable region comprising CDR1, CDR2 and CDR3 comprising the amino-acid sequences set forth in SEQ ID NO:4, SEQ ID NO:5 and SEQ ID NO:6, respectively, and a non-CDR amino-acid sequence that differs in 2 to 4 amino-acids from the amino-acid sequence set forth in SEQ ID NO:13; and analogs, derivatives and antigen-binding-fragments thereof which specifically recognize human CEACAM1.

In the interest of clarity, it should be emphasized that the variable regions of the antibodies provided by the present invention comprise (a) the CDR sequences previously described by the inventors of the present invention, and (b) framework sequences, also denoted herein non-CDR sequences, at least one of which is different in at least one residue from a corresponding fully human framework sequence.

In certain embodiments, the phrase "a sequence which differs from another sequence" as used herein means a sequence which contains a substitution of at least one amino-acid, an insertion of at least one amino-acid, a deletion of at least one amino-acid, or any combination thereof, in comparison to a respective sequence. In certain embodiments, the phrase "a sequence which differs from another sequence" as used herein means a sequence which contains a substitution of at least one amino-acid in comparison to a respective sequence. The term "non-CDR sequence" as used herein refers framework sequence, namely, any amino-acid sequence comprised in a variable region of an antibody, which is not a CDR sequence identified by the present invention. Examples of non-CDR sequence include sequences preceding or adjacent to CDR1, sequences between CDR1 and CDR2, sequences between CDR2 and CDR3, and sequences following or adjacent to CDR3.

Since the variable regions of the antibodies provided by the present invention differ in at least one amino-acid from the variable regions fully human antibodies, they are also labeled "non-fully-humanized" and "non-fully-human" antibodies.

The term "CEACAM1" is used to refer to the protein product of the CEACAM1 gene e.g., NP_001020083.1, NP_001703.2. In humans, 11 different CEACAM1 splice variants have been detected so far. Individual CEACAM1 isoforms differ with respect to the number of extracellular immunoglobulin-like domains (for example, CEACAM1 with four extracellular immunoglobulin-like domains is known as CEACAM1-4), membrane anchorage and/or the length of their cytoplasmic tail (for example, CEACAM1-4 with a long cytoplasmic tail is known as CEACAM1-4L and CEACAM1-4 with a short cytoplasmic tail is known as CEACAM1-4S). The N-terminal domain of CEACAM1 starts immediately after the signal peptide and its structure is regarded as IgV-type. For example, in CEACAM1 annotation P13688, the N-terminal IgV-type domain is comprised of 108 amino acids, from amino acid 35 to 142. This domain was identified as responsible for the homophilic binding activity (Watt et al., 2001, Blood. 98, 1469-79). All variants, including these splice variants are included within the term "CEACAM1".

The terms "anti-CEACAM1 antibody", "an antibody which recognizes CEACAM1", "an antibody against CEACAM1" and "an antibody to CEACAM1" are interchangeable, and used herein to refer to an antibody that binds to the CEACAM1 protein with sufficient affinity and specificity.

The term "antigen" as used herein refers to a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens. An antigen according to the present invention is a CEACAM1 protein or a fragment thereof.

The term "antigenic determinant" or "epitope" as used herein refers to the region of an antigen molecule that specifically reacts with a particular antibody. Peptide sequences derived from an epitope can be used, alone or in conjunction with a carrier moiety, applying methods known in the art, to immunize animals and to produce additional polyclonal or monoclonal antibodies. Isolated peptides derived from an epitope may be used in diagnostic methods to detect antibodies and as therapeutic agents when inhibition of said antibodies is required.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The antigen binding domains, Fab, include regions where the polypeptide sequence varies. The term $F(ab')_2$ represents two Fab' arms linked together by disulfide bonds. The central axis of the antibody is termed the Fe fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hyper-variable domains known as complementarity determining regions (CDRs 1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

The term "antibody" is used in the broadest sense and includes monoclonal antibodies (including full length or intact monoclonal antibodies), polyclonal antibodies, multivalent antibodies, multi-specific antibodies (e.g., bi-specific antibodies), and antibody fragments long enough to exhibit the desired biological activity.

The antibody according to the present invention is a molecule comprising at least the antigen-binding portion of an antibody. Antibody or antibodies according to the invention include intact antibodies, such as polyclonal antibodies or monoclonal antibodies (mAbs), as well as proteolytic fragments thereof, such as the Fab or F(ab')2 fragments. Single chain antibodies also fall within the scope of the present invention.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CHI domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) $F(ab')_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

The term "neutralizing antibody" as used herein refers to a molecule having an antigen-binding site to a specific receptor or ligand target capable of reducing or inhibiting (blocking) activity or signaling through a receptor, as determined by in-vivo or in-vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. Monoclonal Abs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The mAbs of the present invention may be of any immunoglobulin class including IgG, IgM, IgE, or IgA. A hybridoma producing a mAb may be cultivated in-vitro or in-vivo. High titers of mAbs can be obtained by in-vivo production where cells from the individual hybridomas are injected intra-peritoneally into pristine-primed Balb/c mice to produce ascites fluid containing high concentrations of the desired mAbs. Monoclonal Abs of isotype IgM or IgG may be purified from such ascites fluids, or from culture supernatants, using column chromatography methods well known to those of skill in the art.

The term "human antibody" as used herein refers to an antibody which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art.

The terms "molecule having the antigen-binding portion of an antibody" and "antigen-binding-fragments" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific mini-antibodies (see Muller et al., 1998) and single-chain antibodies incorporating such reactive fraction, as well as any other type of molecule in which such antibody reactive fraction has been physically inserted. Such molecules may be provided by any known technique, including, but not limited to, enzymatic cleavage, peptide synthesis or recombinant techniques.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved. The term "antibody analog" as used herein refers to an antibody derived from another antibody by one or more conservative amino acid substitutions.

The term "antibody variant" as used herein refers to any molecule comprising the antibody of the present invention. For example, fusion proteins in which the antibody or an antigen-binding-fragment thereof is linked to another chemical entity is considered an antibody variant.

The term "non-fully-humanized monoclonal antibody" as used herein refers to a monoclonal antibody, having a heavy chain and/or a light chain variable domains in which the amino-acid sequences flanking and/or immediately adjacent to the CDRs are not fully human, i.e. are not identical to any known homologous or corresponding sequences taken from natural human antibodies.

In pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the molecules of the present invention comprising the antigen binding portion of an antibody or comprising another polypeptide including a peptide-mimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly (ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), administration is used.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The term "sugar" refers to monosaccharides, disaccharides, and polysaccharides, Examples of sugars include, but are not limited to, sucrose, trehalose, dextrose, and others.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The pharmaceutical composition according to the present invention may be administered together with an anti-neoplastic composition. According to a specific embodiment the anti-neoplastic composition comprises at least one chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison vincas: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan, dacarbazin; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

According to a specific embodiment, the chemotherapeutic agent is selected from the group consisting of alkylating agents, antimetabolites, folic acid analogs, pyrimidine analogs, purine analogs and related inhibitors, vinca alkaloids, epipodophyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irenotecan, oxaliplatin, capecitabine, paclitaxel and doxetael. Two or more chemotherapeutic agents can be used in a cocktail to be administered in combination with administration of the anti-CEACAM1 antibody.

The term "treatment" as used herein refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include melanoma, lung, thyroid, breast, colon, prostate, hepatic, bladder, renal, cervical, pancreatic, leukemia, lymphoma, myeloid, ovarian, uterus, sarcoma, biliary, or endometrial cancer.

The term "anti-neoplastic composition" refers to a composition useful in treating cancer comprising at least one active therapeutic agent capable of inhibiting or preventing tumor growth or function, and/or causing destruction of tumor cells. Therapeutic agents suitable in an anti-neoplastic composition for treating cancer include, but are not limited to, chemotherapeutic agents, radioactive isotopes, toxins, cytokines such as interferons, and antagonistic agents targeting cytokines, cytokine receptors or antigens associated with tumor cells. Preferably the therapeutic agent is a chemotherapeutic agent.

The term "diagnosing" as used herein refers to determining presence or absence of a pathology, classifying a pathology or a symptom, determining a severity of the pathology, monitoring pathology progression, forecasting an outcome of a pathology and/or prospects of recovery.

The term "amino-acid residue mutation" as used herein refers to a substitution, an insertion, or a deletion of a single amino-acid residue. The term "amino-acid residue backmutation" as used herein refers to a substitution of a single amino-acid residue found in a human antibody framework to a corresponding amino-acid residue found in a murine antibody framework.

The following examples are presented in order to more fully illustrate some embodiments of the invention. They should, in no way be construed, however, as limiting the broad scope of the invention.

EXAMPLES

TABLE 1

CDR sequences. A humanized mAb according to the present invention comprises the following six CDRs:

| $V_L$ CDR3 | $V_L$ CDR2 | $V_L$ CDR1 | $V_H$ CDR3 | $V_H$ CDR2 | $V_H$ CDR1 |
|---|---|---|---|---|---|
| QQGKSLPRT SEQ ID NO: 6 | YTSRLHS SEQ ID NO: 5 | RTSQDIGNYLN SEQ ID NO: 4 | GDYYGGFAVDY SEQ ID NO: 3 | VINPGSGDTNYN EKFKG SEQ ID NO: 2 | GYAFTNNLIE SEQ ID NO: 1 |

TABLE 2

Non-CDR sequences of fully murine and fully human variable regions.

| CDR3-X | CDR2-X-CDR3 | CDR1-X-CDR2 | X-CDR1 | Chain |
|---|---|---|---|---|
| WGQGTSVTVSS (SEQ ID NO: 39) | KATLTADKSSNTAYM QLSSLTSDDSAVYFC AR (SEQ ID NO: 38) | WVKQRPGQGLEW IG (SEQ ID NO: 37) | QVQLQQSGAELVR PGTSVKVSCKAS (SEQ ID NO: 36) | Murine H |
| WGQGTTVTVSS (SEQ ID NO: 10) | RVTMTRDTSISTAYM ELSRLRSDDTAVYYC AR (SEQ ID NO: 9) | WVRQAPGQGLEW MG (SEQ ID NO: 8) | QVQLVQSGAEVK KPGASVKVSCKAS (SEQ ID NO: 7) | Human H |
| FGGGTKLEIK (SEQ ID NO: 43) | GVPSRFSGSGSGTDYS LTISNLEQEDIATYFC (SEQ ID NO: 42) | WYQQKPDGTVKL LIY (SEQ ID NO: 41) | DIQMTQTTSSLSAS LGDRVTISC (SEQ ID NO: 40) | Murine L |

TABLE 2-continued

Non-CDR sequences of fully murine and fully human variable regions.

| CDR3-X | CDR2-X-CDR3 | CDR1-X-CDR2 | X-CDR1 | Chain |
|---|---|---|---|---|
| FGGGTKVEIK (SEQ ID NO: 14) | GVPSRFSGSGSGTDFTFTISSLQPEDIATYYC (SEQ ID NO: 13) | WYQQKPGKAPKLLIY (SEQ ID NO: 12) | DIQMTQSPSSLSASVGDRVTITC (SEQ ID NO: 11) | Human L |

TABLE 3

Non-CDR sequences of humanized back-mutated heavy chain variable regions.

| CDR3-X | CDR2-X-CDR3 | CDR1-X-CDR2 | X-CDR1 | Variant |
|---|---|---|---|---|
| WGQGTSVTVSS (SEQ ID NO: 23) | RATLTADKSINTAYMELSSLTSDDSAVYFCAR (SEQ ID NO: 18) | WVKQAPGQGLEWIG (SEQ ID NO: 16) | QVQLVQSGAELKKPGASVKVSCKAS (SEQ ID NO: 15) | VH1 |
| WGQGTTVTVSS (SEQ ID NO: 10) | RATLTADKSINTAYMELSRLRSDDTAVYFCAR (SEQ ID NO: 19) | WVKQAPGQGLEWIG (SEQ ID NO: 16) | QVQLVQSGAEVKKPGASVKVSCKAS (SEQ ID NO: 7) | VH2 |
| WGQGTTVTVSS (SEQ ID NO: 10) | RATLTADKSINTAYMELSRLRSDDTAVYYCAR (SEQ ID NO: 20) | WVRQAPGQGLEWIG (SEQ ID NO: 17) | QVQLVQSGAEVKKPGASVKVSCKAS (SEQ ID NO: 7) | VH3 |
| WGQGTTVTVSS (SEQ ID NO: 10) | RATLTADKSISTAYMELSRLRSDDTAVYYCAR (SEQ ID NO: 21) | WVRQAPGQGLEWIG (SEQ ID NO: 17) | QVQLVQSGAEVKKPGASVKVSCKAS (SEQ ID NO: 7) | VH4 |
| WGQGTTVTVSS (SEQ ID NO: 10) | RVTMTADKSISTAYMELSRLRSDDTAVYYCAR (SEQ ID NO: 22) | WVRQAPGQGLEWIG (SEQ ID NO: 17) | QVQLVQSGAEVKKPGASVKVSCKAS (SEQ ID NO: 7) | VH5 |

* Bold and underlined amino-acids with back mutations to murine sequence.

TABLE 4

Non-CDR sequences of back-mutated humanized light chain variable regions.

| CDR3-X | CDR2-X-CDR3 | CDR1-X-CDR2 | X-CDR1 | Variant |
|---|---|---|---|---|
| FGGGTKVEIK (SEQ ID NO: 14) | GVPSRFSGSGSGTDYTLTISSLQQEDIATYFC (SEQ ID NO: 25) | WYQQKPGKAVKLLIY (SEQ ID NO: 24) | DIQMTQSPSSLSASVGDRVTTTC (SEQ ID NO: 11) | VL1 |
| FGGGTKVEIK (SEQ ID NO: 14) | GVPSRFSGSGSGTDYTLTISSLQPEDIATYFC (SEQ ID NO: 26) | WYQQKPGKAVKLLIY (SEQ ID NO: 24) | DIQMTQSPSSLSASVGDRVTTTC (SEQ ID NO: 11) | VL2 |
| FGGGTKVEIK (SEQ ID NO: 14) | GVPSRFSGSGSGTDYTFTISSLQPEDIATYFC (SEQ ID NO: 27) | WYQQKPGKAVKLLIY (SEQ ID NO: 24) | DIQMTQSPSSLSASVGDRVTTTC (SEQ ID NO: 11) | VL3 |

* Bold and underlined amino-acids with back mutations to murine sequence.

TABLE 5

Non-CDR sequences of back-mutated humanized variable regions.

| SEQ ID NO: | Amino acid sequence | Variable regions |
|---|---|---|
| 28 | SEQ ID NO: 15 - SEQ ID NO: 1 - SEQ ID NO: 16 - SEQ ID NO: 2 - SEQ ID NO: 18 - SEQ ID NO: 3 - SEQ ID NO: 23 | Heavy chain variable region #1 |
| 29 | SEQ ID NO: 7 - SEQ ID NO: 1 - SEQ ID NO: 16 - SEQ ID NO: 2 - SEQ ID NO: 19 - SEQ ID NO: 3 - SEQ ID NO: 10 | Heavy chain variable region #2 |
| 30 | SEQ ID NO: 7 - SEQ ID NO: 1 - SEQ ID NO: 17 - SEQ ID NO: 2 - SEQ ID NO: 20 - SEQ ID NO: 3 - SEQ ID NO: 10 | Heavy chain variable region #3 |

TABLE 5-continued

Non-CDR sequences of back-mutated humanized variable regions.

| SEQ ID NO: | Amino acid sequence | Variable regions |
|---|---|---|
| 31 | SEQ ID NO: 7 - SEQ ID NO: 1 - SEQ ID NO: 17 - SEQ ID NO: 2 - SEQ ID NO: 21 - SEQ ID NO: 3 - SEQ ID NO: 10 | Heavy chain variable region #4 |
| 32 | SEQ ID NO: 7 - SEQ ID NO: 1 - SEQ ID NO: 17 - SEQ ID NO: 2 - SEQ ID NO: 22 - SEQ ID NO: 3 - SEQ ID NO: 10 | Heavy chain variable region #5 |
| 33 | SEQ ID NO: 11 - SEQ ID NO: 4 - SEQ ID NO: 24 - SEQ ID NO: 5 - SEQ ID NO: 25 - SEQ ID NO: 6 - SEQ ID NO: 14 | Light chain variable region #1 |
| 34 | SEQ ID NO: 11 - SEQ ID NO: 4 - SEQ ID NO: 24 - SEQ ID NO: 5 - SEQ ID NO: 26 - SEQ ID NO: 6 - SEQ ID NO: 14 | Light chain variable region #2 |
| 35 | SEQ ID NO: 11 - SEQ ID NO: 4 - SEQ ID NO: 24 - SEQ ID NO: 5 - SEQ ID NO: 27 - SEQ ID NO: 6 - SEQ ID NO: 14 | Light chain variable region #3 |

The reference fully-humanized heavy chain sequence (SEQ ID NO: 57), to which back-mutations are introduced is composed of:

QVQLVQSGAEVKKPGASVKVSCKAS-(SEQ ID NO: 7)-GYAFTNN-LIE- (SEQ ID NO: 1)-WVRQAPGQGLEWMG-(SEQ ID NO: 8)

VINPGSGDTNYNEKFKG-(SEQ ID NO: 2)-

RVTMTRDTSISTAYMELSRLRSDDTAVYYCAR-(SEQ ID NO: 9)-

GDYYGGFAVDY-(SEQ ID NO: 3)-WGQGTTVTVSS (SEQ ID NO: 10).

The reference fully-humanized light chain sequence (SEQ ID NO: 58), to which back-mutations are introduced is composed of:

DIQMTQSPSSLSASVGDRVTITC-(SEQ ID NO: 11-RTSQDIGNYLN- (SEQ ID NO: 4)-WYQQKPGKAPKLLIY- (SEQ ID NO: 12)-YTSRLHS-(SEQ ID NO: 5)

GVPSRFSGSGSGTDFTFTISSLQPEDIATYYC-(SEQ ID NO: 13)-

QQGKSLPRT-(SEQ ID NO: 6)-FGGGTKVEIK-(SEQ ID NO: 14)

Example 1. Design of CDR-Grafted Antibody Variable Region Sequences

Figure 1A:
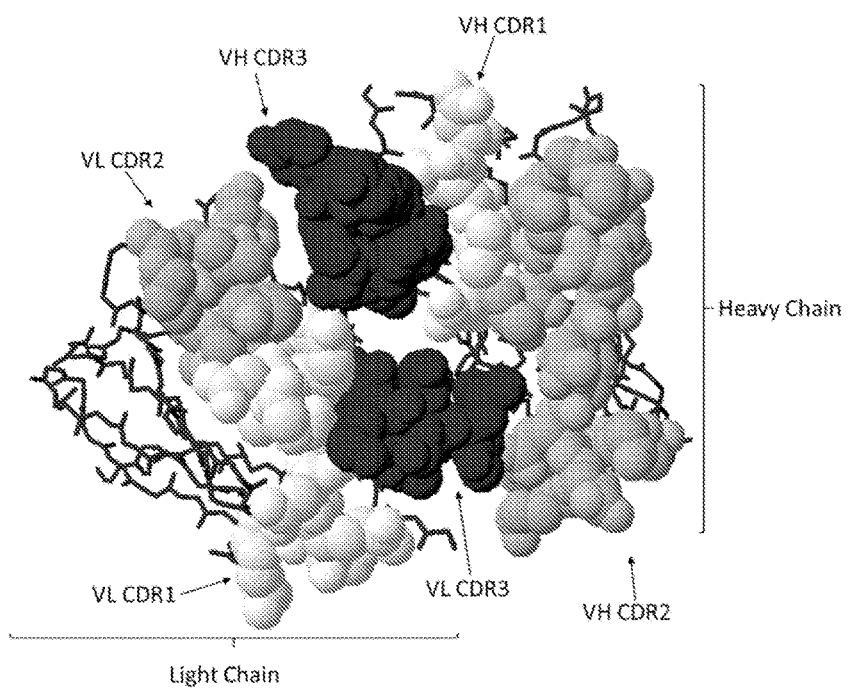
FIG. 1 is a structural model of the chimeric anti-CEACAM-1 antibody (CM-10) V regions in top view (A) and in stereo side views (B), produced by the protein structure homology-modelling program Swiss PDB.
Figure 1B:
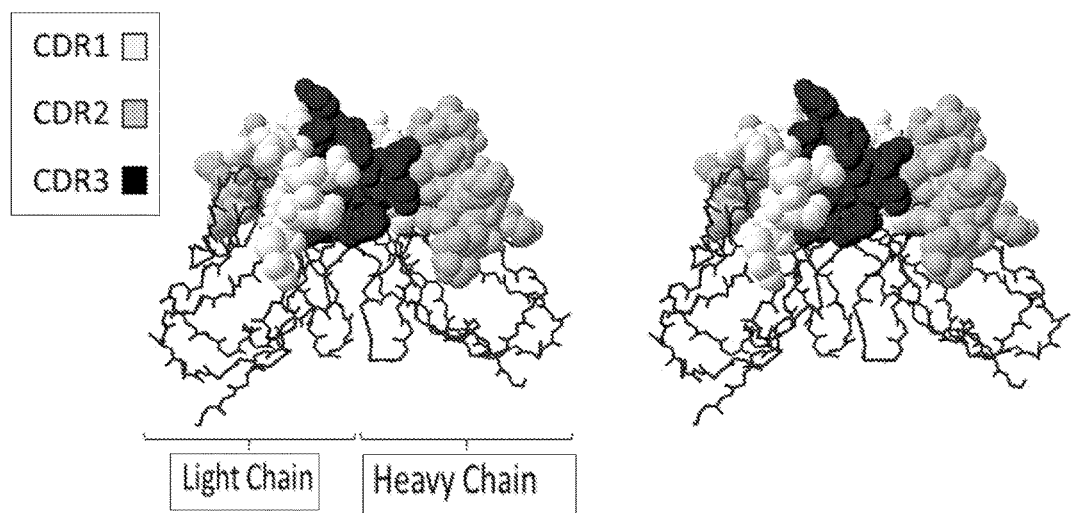

Structural models of the chimeric anti-CEACAM-1 antibody V regions were produced using Swiss PDB and analyzed in order to identify amino acids in the V region frameworks that may be important for the binding properties of the antibody (FIG. 1). These amino acids were noted for incorporation into one or more variant CDR-grafted antibodies. Both the VH and V, sequences of CM-10 contain typical framework residues and the CDR 1, 2 and 3 motifs are comparable to many murine antibodies. The CDRs were taken directly from the murine sequence. The Swiss PDB models were then analyzed, together with mouse/human homologies at critical positions, to highlight framework regions and individual residues which could potentially impact on the presentation of the CDRs.

Design of Variants

The heavy and light chain V region amino acid sequence were compared against a database of human germline V region sequences in order to identify the heavy and light chain human sequences with the greatest degree of homology for use as V region frameworks. A series of heavy and light chain V regions were then designed by grafting the CDRs onto the frameworks and, if necessary, by back-mutation to the murine sequence of residues identified above as potentially critical to the restoration of the chimeric antibody binding efficiency. It was considered that a small number of mouse residues needed to be retained in each variant. Variant sequences with lowest incidence of potential T cell epitopes were then selected as determined by application of Antitope's proprietary in-silico technologies, iTope™ and TCED™ (T Cell Epitope Database) (Perry et al 2008, Bryson et al 2010). The number of back mutations was determined by the starting murine sequence. From the structural analysis, a maximum of 13 positions were identified in the $V_H$ and 5 positions were identified in the $V_\kappa$ as residues which could be structurally important. These were prioritized and variants were designed which incorporated varying numbers of these. Although there is no theoretical limit to the number of back mutations, the more back mutations incorporated, the less human the sequence may be. Five $V_H$ chains and three $V_\kappa$ chains were designed with sequences set forth in SEQ ID NOs: 28 to 35.

iTope™ and TCED™

The iTope™ software predicts favorable interactions between amino acid side chains of a peptide and specific binding pockets (in particular pocket positions; p1, p4, p6, p7 and p9) within the binding grooves of 34 human MHC class II alleles. The location of key binding residues is achieved by the in silico generation of 9 mer peptides that overlap by one amino acid spanning the test protein sequence. In-house comparisons with physical MHC class II binding experiments has shown that iTope™ can be used to successfully discriminate with high accuracy between peptides that either bind or do not bind MHC class II molecules. However, the results should be assessed in the light of the fact that all predictive methods for MHC class II binding inherently over-predict the number of T cell epitopes since they do not allow for other important processes during antigen presentation such as protein/peptide processing, recognition by the T cell receptor or T cell tolerance to the peptide.

The TCED™ contains the sequences of all the peptides previously screened in EpiScreen™ T cell epitope mapping assays. The TCED™ is used to search any test sequence against a large (>10,000 peptides) database of peptides by BLAST search in order to specifically select segments that had previously been shown not to stimulate T cell responses. In addition, any regions with significant homology to T cell epitopes in the database were discarded.

Construction of CDR-Grafted Variants

All variant CDR-grafted VH and V, region genes for CM-10 were synthesized using a series of overlapping oligonucleotides that were annealed, ligated and PCR amplified to give full length synthetic V regions. The assembled variants were then cloned directly into an expression vector system for both IgG1 and IgG4 (S241P) $V_H$ chains and $V_\kappa$ chains. All constructs were confirmed by sequencing.

Construction, Expression and Purification of Antibodies

The chimeric antibody genes and all combinations of CDR-grafted VH and V, chains (i.e. a total of 15 pairings for each of IgG1 and IgG4 (S241P)) were transiently transfected into HEK293-EBNA (ATCC cat. no. CRL-10852) cells using calcium phosphate. The transient transfections were incubated for up to five days prior to harvesting supernatants.

Figure 2A:
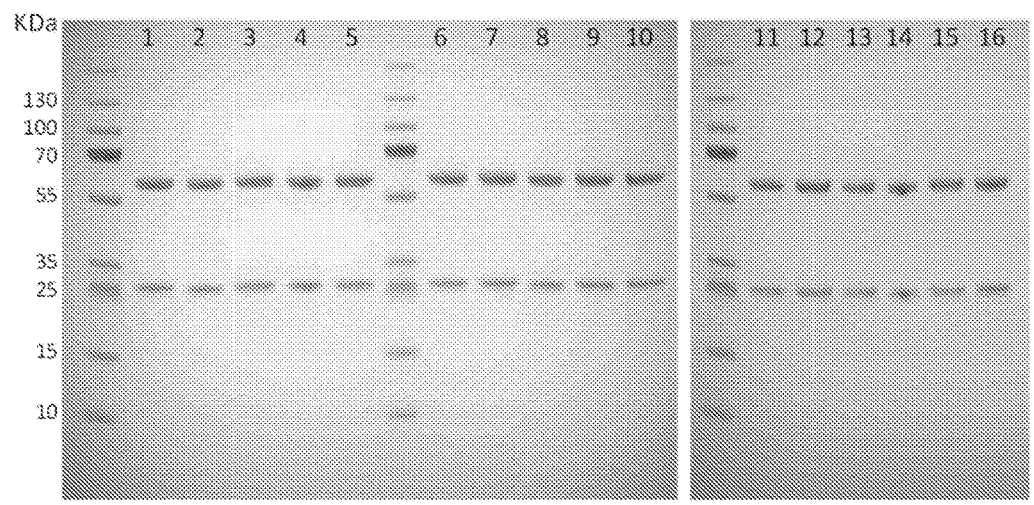
FIG. 2 is a Coomassie Blue-stained SDS-PAGE gel of Protein A-purified antibodies. Approximately 2 μg of each sample was loaded on a NuPage 4-12% Bis-Tris gel (Invitrogen cat. no. NP0322BOX) and run at 200 V for 40 min. (A) IgG1 CDR-grafted variants; (B) IgG4 (S241P) CDR-grafted variants. Fermentas Pageruler Plus (SM1811) was used as molecular weight standard (containing reference bands at 10, 25, and 70 kDa). The samples were numbered as follows.
Figure 2B:
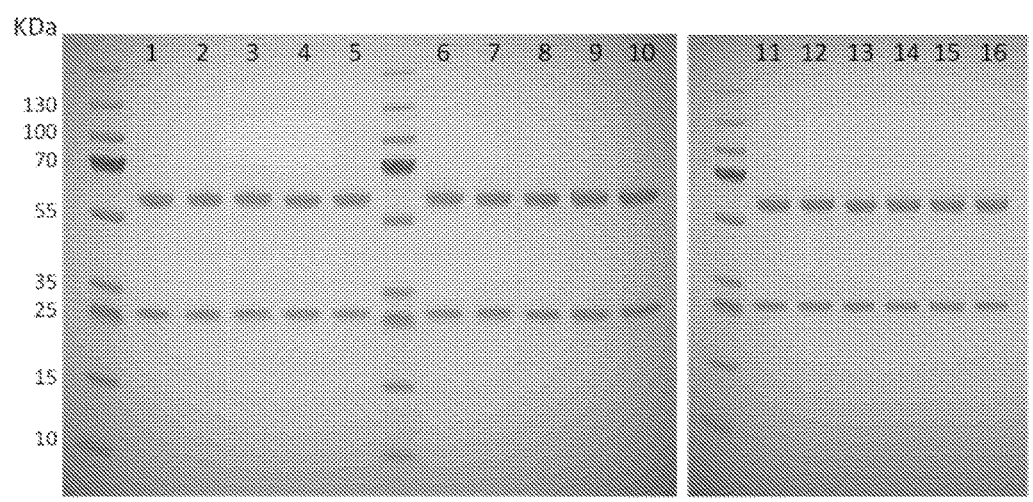
Figure 3A:
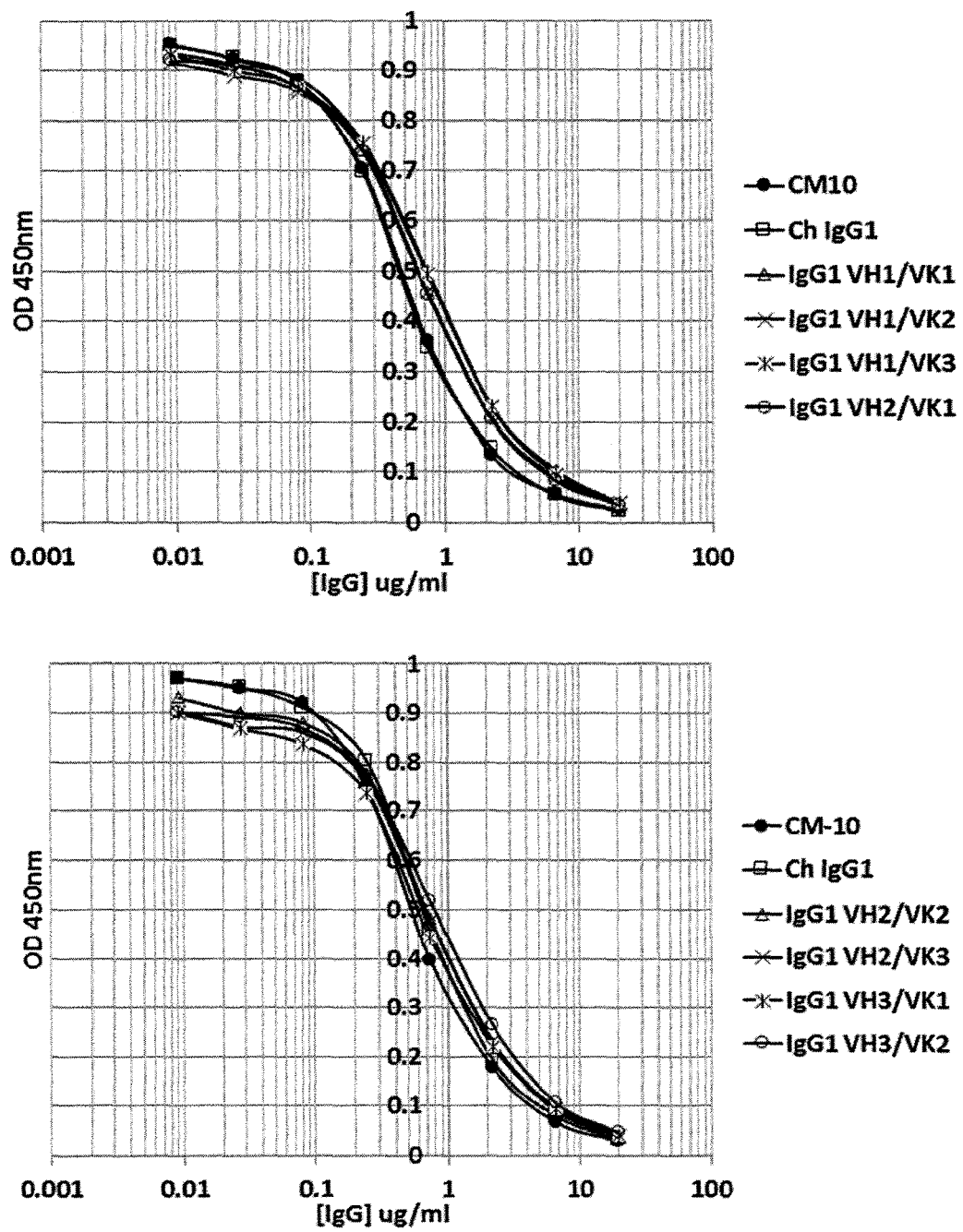
Figure 3A:
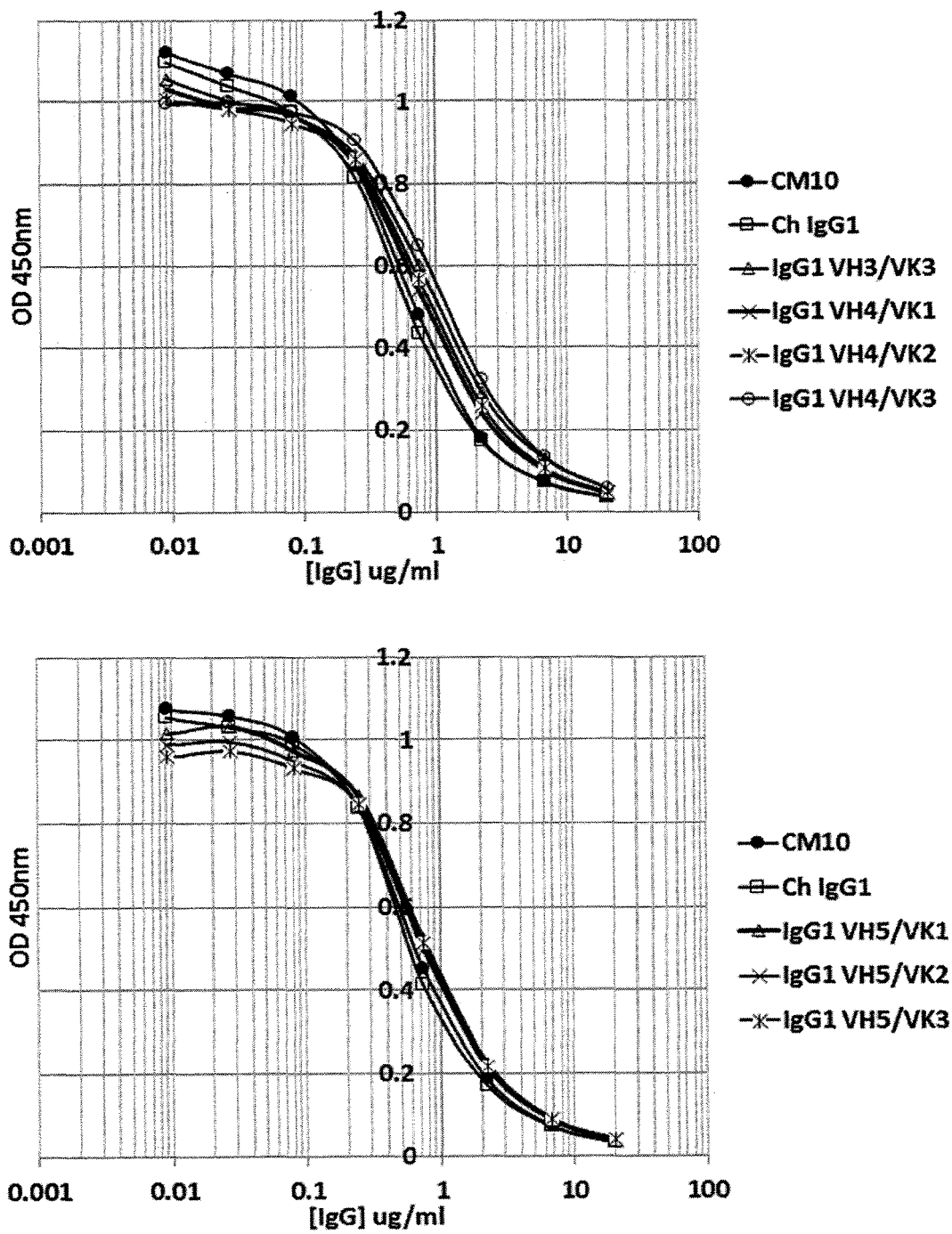
Figure 3B:
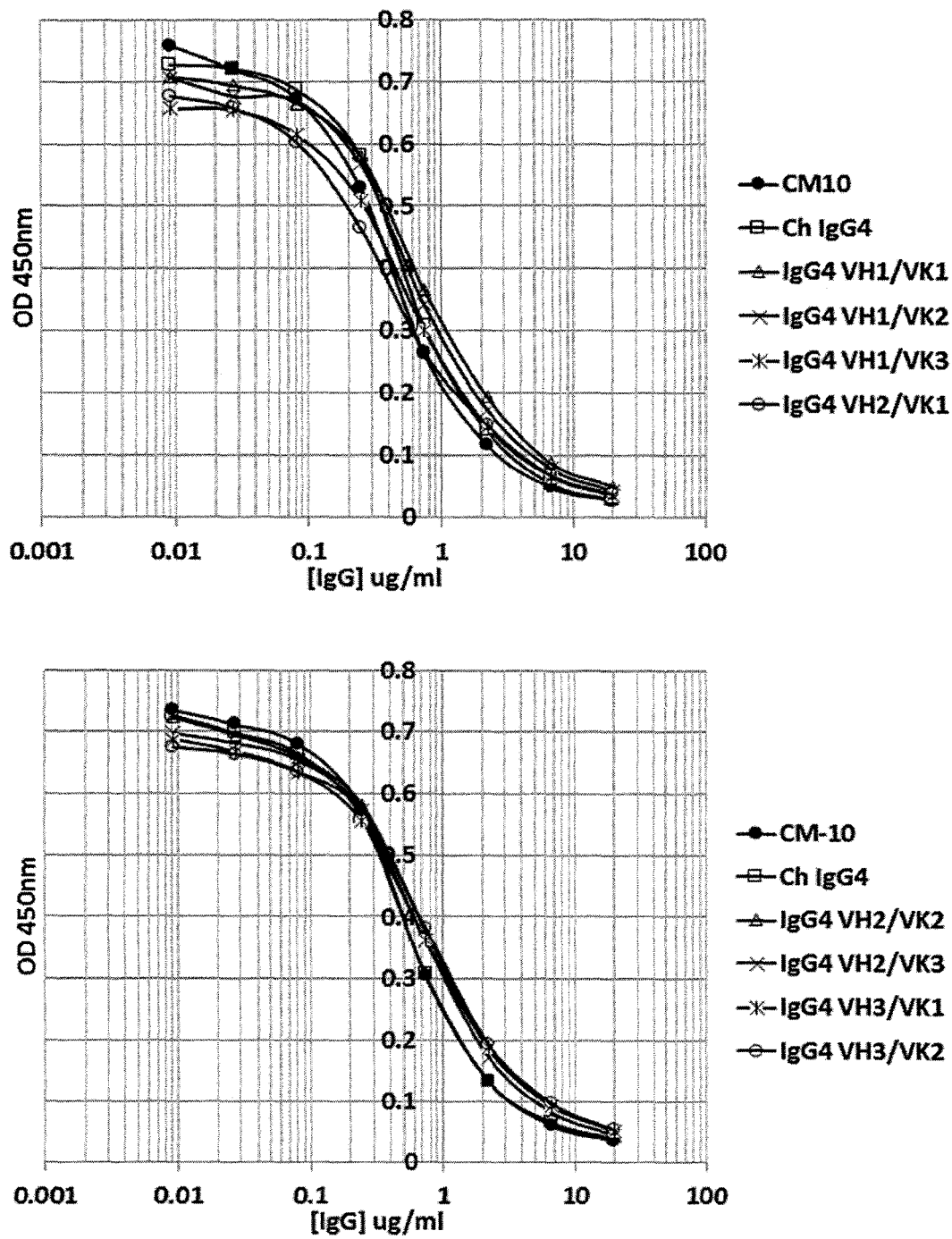
Figure 3B:
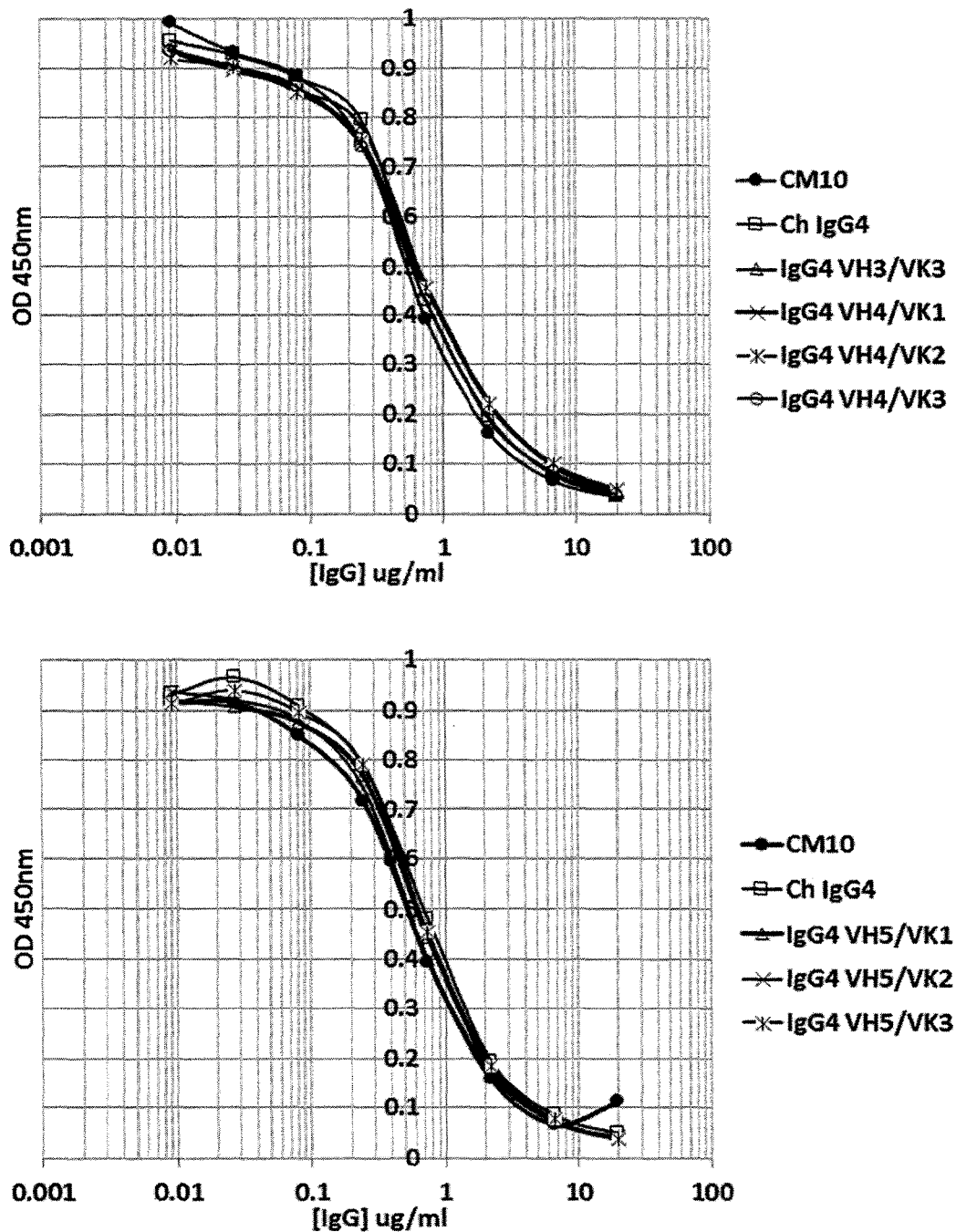

The chimeric antibodies and CDR-grafted variants of CM-10 were purified from transient cell culture supernatants on a Protein A sepharose column (GE Healthcare cat. no. 110034-93), buffer exchanged into 1×PBS pH 7.4 and quantified by $OD_{280\ nm}$ using an extinction coefficient based on the predicted amino acid sequence ($E_{c(0.1\%)}$=~1.37-1.40 for CM-10 chimeric antibody and variants). The chimeric antibodies and lead humanized variants were analyzed by reducing SDS-PAGE. Bands corresponding to the predicted sizes of the $V_H$ and $V_\kappa$ chains were observed with no evidence of any contamination (FIG. 2).

Example 2. Competition Binding of Purified Antibodies to Human CEACAM-1

The binding of purified chimeric CM-10 antibody together with the chimeric antibodies and each of the CDR-grafted variants to recombinant human CEACAM-1 were assessed in a competitive ELISA. A dilution series (three-fold) of chimeric or humanized antibodies from 20 µg/ml to 0.009 µg/ml was premixed with a constant concentration of biotinylated chimeric CM-10 (0.005 µg/ml, final concentration) before incubating for 1 hour at room temperature on a Nunc Immuno MaxiSorp 96 well flat bottom microtitre plate (Fisher cat. no. DIS-971-030J) pre-coated with 0.5 µg/ml recombinant human CEACAM-1 (R&D Systems cat. no. 2244-CM-050) diluted in 1×PBS pH 7.4. The binding of the biotinylated antibody was detected with streptavidin-HRP (Sigma cat. no. S5512) and TMB substrate (Invitrogen cat. no. 00-2023). The reaction was stopped with 3M HCl, absorbance read at 450 nm on a Dynex Technologies MRX TC II plate reader and the binding curves plotted.

All humanized variants gave similar binding profiles to chimeric CM-10 with the binding curves shown in FIG. 3. These data were used to calculate $IC_{50}$ values for each antibody and was normalized to the $IC_{50}$ of chimeric CM-10 as included on each ELISA and as shown in Tables 6 and 7.

TABLE 6

$IC_{50}$ values for humanized anti-CEACAM-1 variants.

| Construct | $IC_{50}$ [IgG] µg/mL | |
|---|---|---|
| | IgG1 Variants | IgG4 (S241P) Variants |
| VH1/VK1 | 0.78 | 0.78 |
| VH1/VK2 | 0.70 | 0.70 |
| VH1/VK3 | 0.77 | 0.54 |
| VH2/VK1 | 0.68 | 0.43 |
| VH2/VK2 | 0.78 | 0.76 |
| VH2/VK3 | 0.76 | 0.71 |
| VH3/VK1 | 0.69 | 0.71 |
| VH3/VK2 | 0.85 | 0.77 |
| VH3/VK3 | 0.86 | 0.73 |
| VH4/VK1 | 0.73 | 0.69 |
| VH4/VK2 | 0.78 | 0.69 |
| VH4/VK3 | 0.99 | 0.63 |
| VH5/VK1 | 0.77 | 0.74 |
| VH5/VK2 | 0.72 | 0.70 |
| VH5/VK3 | 0.74 | 0.70 |

TABLE 7

Calculated relative $IC_{50}$ values for humanized anti-CEACAM-1 variants.

| Construct | $IC_{50}$ normalized to CM-10 | |
|---|---|---|
| | IgG1 Variants | IgG4 Variants |
| VH1/VK1 | 1.46 | 1.52 |
| VH1/VK2 | 1.32 | 1.36 |
| VH1/VK3 | 1.44 | 1.05 |
| VH2/VK1 | 1.29 | 0.84 |
| VH2/VK2 | 1.24 | 1.26 |
| VH2/VK3 | 1.21 | 1.16 |
| VH3/VK1 | 1.10 | 1.16 |
| VH3/VK2 | 1.36 | 1.26 |
| VH3/VK3 | 1.37 | 1.23 |
| VH4/VK1 | 1.15 | 1.15 |
| VH4/VK2 | 1.24 | 1.17 |
| VH4/VK3 | 1.56 | 1.06 |
| VH5/VK1 | 1.17 | 1.23 |
| VH5/VK2 | 1.09 | 1.16 |
| VH5/VK3 | 1.12 | 1.17 |

The normalized $IC_{50}$ data showed a range of 0.84 to 1.56 for all variants tested indicating that the binding efficiencies of all CDR-grafted antibodies to human CEACAM-1 were comparable to that of the chimeric CM-10.

Example 3. Combination of Humanized mAb to CEACAM1 and Anti PD-1/PD-L Antibodies A. Synergistic effects of anti-CEACAM1 and anti-PD-1 antibodies on the cytotoxicity of human TIL cells against human melanoma cells was demonstrated. Human melanoma cancer cells (MALME 3M) were grown in the presence of IFN-ã to induce PD-L1 expression. Human TIL cells (TIL14) were incubated with a monoclonal antibody to human CEACAM1 (CM-24) (0.01 µg/ml, 0.05 µg/ml, 0.1 µg/ml, 0.5 µg/ml), a monoclonal antibody to human PD-1 (clone E12.2H7) or with a combination of both antibodies (0.005, 0.025, 0.05 and 0.25 µg/ml of each antibody) for 30 minutes at 37° C. IFN-ã-treated human melanoma cancer cells were added for overnight incubation, prior to cytotoxicity evaluation. FIG. 4 demonstrates that both anti-CEACAM1 antibodies and anti-PD-1 antibodies were able to bind their respective targets on human lymphocytes such as TIL cells, and that this binding significantly increased the toxicity of the human TIL cells against human cancer cells over each monotherapy alone. It was therefore concluded that protecting lymphocytes from immuno-suppressive signals from target cancer cells results in substantial cytotoxicity toward these cancer cells.

B. Synergistic effects of anti-CEACAM1 and anti-PD-1 antibodies on Granzyme B levels and the cytotoxicity of human TIL cells against human melanoma cells when anti-PD-1 antibodies are added prior to the addition of anti-CEACAM1 antibodies was also shown: Human melanoma cancer cells (MALME 3M) were grown in the presence of IFN-ã to induce PD-L1 expression. Human TIL cells (TIL14) were incubated with medium only (black), non-specific IgG antibody (0.8 µg/ml, white), various concentrations (0.05 µg/ml, 0.1 µg/ml, 0.2 µg/ml, 0.4 µg/ml, 0.8 µg/ml) of CM-24, a mAb to human PD-1 (clone E12.2H7) or a combination of both antibodies (0.05 µg/ml each, 0.1 µg/ml each, 0.2 µg/ml each, 0.4 µg/ml each, 0.8 µg/ml each). The monoclonal antibody to human PD-1 was added first for 30 minutes at 37° C., followed by the addition of the mAb to human CEACAM1. IFN-ã-treated human melanoma cancer cells were added for overnight incubation, prior to cytotoxicity evaluation. The combination index (CI) was calculated to be 0.15. In the same assay, the level of the cytotoxic protein granzyme B that is secreted upon cytotoxic cell activation was evaluated by commercial granzyme B ELISA Kit. FIG. 5 demonstrates that anti-CEACAM1 antibodies and anti-PD-1 antibodies are able to bind their respective targets on human lymphocytes such as TIL cells, and that this binding increases the granzyme B secretion and toxicity of the human TIL cells against human cancer cells. FIG. 5 indicates again that protecting lymphocytes from immuno-suppressive signals from target cancer cells results in substantial cytotoxicity toward target cancer cells and suggests that timing could be a critical factor in the combined therapy.

C. Synergistic effects of anti-CEACAM1 and anti-PD-L1 antibodies on Granzyme B levels and the cytotoxicity of human TIL cells against human melanoma cells when anti-PD-L1 antibodies are added prior to the addition of anti-CEACAM1 antibodies (data not shown). Human melanoma cells (MALME 3M) were grown in the presence of IFN-ã to induce PD-L1 expression. Human TIL cells (TIL14) were incubated with medium only (black), non-specific IgG antibody (0.8 µg/ml, white), various concentrations (0.05 µg/ml, 0.1 µg/ml, 0.2 µg/ml, 0.4 µg/ml, 0.8 µg/ml) of a monoclonal antibody to human CEACAM1 (CM-24), a monoclonal antibody to human PD-L1 (clone 29E.2A3) or a combination of both antibodies (0.05 µg/ml each, 0.1 µg/ml each, 0.2 µg/ml each, 0.4 µg/ml each, 0.8 µg/ml each). The anti-PD-L1 antibody was added first for 30 minutes at 37° C., followed by the addition of the monoclonal antibody to human CEACAM1. IFN-ã-treated human melanoma cancer cells were added for overnight incubation prior to cytotoxicity evaluation. The combination index (CI) was calculated to be 0.67. Results represent an average of % cytotoxicity±SE as determined by classical LDH release assay from triplicate wells per treatment. *P≤0.05 paired T-test compared to a-PD-L1 only. In the same assay, the levels of the cytotoxic protein granzyme B that is secreted upon cytotoxic cell activation was evaluate by commercial granzyme B ELISA Kit. Results represent average granzyme B level from triplicate wells per treatment. The results demonstrate that anti-CEACAM1 antibodies and anti-PD-L1 antibodies are able to bind their respective targets on human lymphocytes (such as TIL cells) and on human cancer cells (such as melanoma cells), and that this binding increases the granzyme B secretion and toxicity of the human TIL cells against human cancer cells. It was further demonstrates that blocking the PD-1/PD-L1 and CEACAM1/CEACAM1 interactions can result in synergistic affect and that protecting lymphocytes from the PD-1$^{lymphocyte}$/PD-Ligand$^{cancer\ cell}$ immuno-suppressive signal results in substantial cytotoxicity toward these cancer cells, regardless to the antigen targeted, either PD-1, PD-L1 or PD-L2.

D. Synergistic effects of anti-CEACAM1 and anti-PD-1 antibodies on the cytotoxicity of human LAK cells against human melanoma cells when anti-PD-1 antibodies are added prior to the addition of anti-CEACAM1 antibodies. Human melanoma cells (SK-MEL28, CEACAM1 positive, PD-L1 positive) were grown in the presence of IFN-ã to induce PD-L1 expression. Human LAK (lymphokine-activated killer) cells generated by activation of PBMCs from a healthy human donor with IL-2 (500 units/ml) for 7 days were incubated with medium only (white), non-specific IgG antibody (0.8 µg/ml, black), various concentrations (0.1 µg/ml, 0.2 µg/ml, 0.4 µg/ml, 0.8 µg/ml) of a monoclonal antibody to human CEACAM1 (CM-24), a monoclonal antibody to human PD-1 (clone E12.2H7) or a combination of both antibodies (0.1 µg/ml each, 0.2 µg/ml each, 0.4 µg/ml each, 0.8 µg/ml each). The monoclonal antibody to human PD-1 was added first for 30 minutes at 37° C., followed by the addition of the monoclonal antibody to human CEACAM1. IFN-ã-treated human melanoma cells were added for 24 hour incubation, prior to cytotoxicity evaluation. FIG. 6 demonstrates that anti-CEACAM1 antibodies and anti-PD-1 antibodies are able to bind their respective targets on activated human lymphocytes such as LAK cells, and that this binding increases the toxicity of the human LAK cells against human cancer cells. The combination index (CI) was calculated to be <0.8. FIG. 6 further demonstrates that the binding of these antibodies to LAK cells is somehow interrelated, warranting a further study of their binding mechanism, and that this mechanism is present in variety of activated lymphocytes.

E. Treatment with anti-CEACAM1 antibodies increases PD-L1 expression on target cancer cells. Human NK cells (NK92MI) were incubated with or without a monoclonal antibody to human CEACAM1 (10 µg/ml CM-24), followed by the addition of human melanoma cancer cells (SKMEL28). The cells were incubated for 24, 48 and 72 hours and PD-L1 levels were measured at each time point by FACS analysis. The mean ratio levels of anti-PD-L1 compared to an appropriate isotype control for the indicated treatments at different time points is shown in FIG. 7 demonstrating that the expression of CEACAM1 and PD-L1 on cancer cells is indeed interrelated. The addition of anti-CEACAM1 antibodies results in increased PD-L1 expression on surviving cancer cells thus providing additional support for combined treatment with both agents. It may be beneficial to treat cancer by first administering anti CEACAM1 antibodies, and then further administering anti-PD-L1 and/or anti-PD-L2 antibodies, since the number of PD-L1 proteins on the cancer cells remains relatively high, making the cells more sensitive for anti PD-1/PD-L1 antibodies treatment, implying that the combinational therapy may improve the clinical outcome. Administration of different antibodies at separate times, rather than concurrently, maximizes the cytotoxic effect of lymphocytes against cancer cells. Without being bound to any theory or mechanism, this finding may be linked to another surprising finding of the present invention, according to which treatment with anti-CEACAM1 antibodies increases PD-L1 expression on target cancer cells. Hypothetically, this would support the need for a plurality of antibodies to obtain improved efficacy for cytotoxic lymphocytes. It may be envisioned that the administration of anti-PD-1 antibodies first blocks PD-1 molecules on lymphocytes, the later administration of anti-CEACAM1 antibodies blocks CEACAM1 molecules on lymphocytes and/or target cancer cells and increases expression of PD-1 ligands on target cancer cells. However, since PD-1 molecules on lymphocytes are already blocked, the elevated expression levels of PD-1 ligands on target cancer cells do not prevent lymphocytes from efficiently exerting their full cytotoxic potential.

F. Synergistic effects of anti-CEACAM1 and anti-PD-1 antibodies on tumor progression in immuno-competent mice. Murine lymphoma cells ($5*10^6$, A20) were allografted into the abdomen of Balb/C mice by subcutaneous injection on Day 1. On day 10, tumors reached an average volume of 45 mm$^3$, and mice were randomized into 4 separate groups (11-12 mice per group), and intravenously administered with either PBS, CC-1 (anti murine CEACAM1 antibody, 6 mg/kg, PRM-1 (anti murine PD-1 antibody, 6 mg/kg) or a combination of CC-1 and PRM-1 (6 mg/kg each). Treatments were repeated on days 15 and 20. The effect of a monoclonal antibody to human CEACAM1 alone, a monoclonal antibody to human PD-1 alone, and a combination of both antibodies on tumor growth inhibition was followed Immuno-competent Balb/C mice were selected for this experiment to allow evaluation of anti-murine-CEACAM1 and anti-murine-PD-1 antibodies' biological activity in mice with intact immune system and to evaluate the entire immune system reaction against the murine cancer cells. As a whole, this model simulates therapies in humans, in which cancer patients would receive combinations of anti-human-CEACAM1 and anti-human-PD-1/PD-L1/PD-L2 antibodies. Without being bound to any theory or mechanism, it is hypothesized that a combination of anti-CEACAM1 and anti-PD-1/PD-L1/PD-L2 antibodies would prohibit cancer cells to circumvent the activation and cytotoxicity of the patient's immune system, thus producing a significant anti-cancer response. FIG. 8 demonstrates that anti-CEACAM1 antibodies and anti-PD-1/PD-L1/PD-L2 antibodies are able to bind their respective targets on tumor cells and/or immune cells in-vivo, and that this combined binding significantly attenuates tumor progression compared to each mono-therapy. This result is highly important, as it attests to the efficacy and potential of the use of a combined anti-CEACAM1 and anti-PD-1/PD-L1/PD-L2 even in established tumors of considerable volumes, which mimic the clinical setting where patients with established tumors are being treated.

Example 4. Combination Treatment with Humanized mAb to CEACAM1 and LAK Cells

A. Anti-CEACAM1 antibodies increase the cytotoxicity of human LAK cells against human melanoma cells: PBMC cells were isolated from a healthy donor followed by activation with IL-2 (500 or 1000 units/ml) for 3 days to generate a population of human LAK cells. Then, the human LAK cells were incubated with 0.1 µg/ml, 0.5 µg/ml, 2.5 µg/ml, 5 µg/ml or 10 µg/ml of an anti-CEACAM1 antibody (CM-24) for 30 minutes at 37° C. Human melanoma cells (SKMEL28) were added for an incubation of 24 hours, after which cytotoxicity was determined. FIG. 9 demonstrates that while human LAK cells are cytotoxic to human melanoma cancer cells on their own (compare e.g. two left bars), the addition of anti-CEACAM1 antibodies significantly increases cytotoxicity to these human melanoma cancer cells in a dose-dependent manner B. Anti-CEACAM1 antibodies increase the cytotoxicity of human LAK cells against a variety of human pancreatic and lung cancer cells. PBMC cells were isolated from a healthy donor followed by activation with IL-2 (500 units/me for 7 days to generate a population of human LAK cells. Then, the human LAK cells were incubated with 0.1 µg/ml to 10 µg/ml of an anti-CEACAM1 antibody (CM-24) as indicated, for 30 minutes at 37° C. Three different human pancreatic cancer cells, T3M4, SU8686 and PANC2, and two different human lung cancer cells, H358 and H460, were added for an incubation of 24 hours. FIG. 10 demonstrates that while human LAK cells are cytotoxic to human pancreatic T3M4 cancer cells on their own, the addition of anti-CEACAM1 antibodies significantly increases cytotoxicity to these human cancer cells in a dose-dependent manner Similar results were obtained for the other pancreatic and lung cancer cell.

C. Anti-CEACAM1 antibodies enhance granzyme B secretion of human LAK cells in the presence of human pancreatic and lung cancer cells. Human LAK cells were incubated with an anti-CEACAM-1 antibody (CM-24) in different concentrations for 30 minutes at 37° C. Human pancreatic cancer cells T3M4 (A) or human lung cancer cells H358 (B) were then added for an incubation of 24 hours. Granzyme B secretion was measured by ELISA. The results demonstrate that while human LAK cells produce high levels of Granzyme B on their own, the addition of anti-CEACAM1 antibodies significantly increases Granzyme B levels in a dose-dependent manner D. Anti-CEACAM1 antibodies enhance enhances IFN-γ secretion of human LAK cells in the presence of human cancer cells. Human LAK cells were incubated with an anti-CEACAM-1 antibody (CM-24) in different concentrations for 30 minutes at 37° C. Human lung cancer cells H358 or H460 were then added for an incubation of 24 hours. IFN-γ secretion was measured by ELISA. FIG. 11 demonstrates that while human LAK cells produce high levels of IFN-γ on their own, the addition of anti-CEACAM1 antibodies significantly increases IFN-γ levels in a dose-dependent manner.

Example 5. CEACAM1 Expression Correlates with the Presence of B-Raf Mutations in Cancer Cells A. Evaluating of biopsy samples from 24 Melanoma cancer patients for CEACAM1 expression levels and for BRAF genotype revealed that there is a statistically significant correlation between B-Raf V600E mutation and expression of CEACAM1. More specifically, whereas only 50% (3/6) of the melanoma cells having a wild type B-Raf, i.e a valine in position 600, expressed detectable levels of CEACAM1 (Ct of 36 and less), 100% (18/18) of the melanoma cells having a mutated B-Raf, i.e a glutamic acid in position 600, expressed detectable levels of CEACAM1 (Ct of 36 and less).

B. CEACAM1 extracellular staining of cancer cells treated with B-Raf or MEK inhibitors. $1.0*10^6$ cells of a B-Raf W.T. cell sample (076mel) and two B-Raf V600E cell samples (526mel, 624mel) were incubated with different concentrations of vemurafenib or selumetinib (0.1 µM or 1 µM) for 2 to 48 hours. At each time point, CEACAM1 expression on the cells was determined by FACS. Volume equivalents of DMSO (vehicle) were used as control. The results demonstrated while 0.1 µM and 1 µM vemurafenib did not have any effect on CEACAM1 expression levels on cells having W.T. B-Raf (076mel), 0.1 µM and 1 µM vemurafenib had a dose-dependent effect on CEACAM1 expression levels on cells having mutated B-Raf (526mel, 624mel). The results further demonstrate that selumetinib had a similar effect to vemurafenib on cells having mutated B-Raf (526mel, 624mel), and that while 1 µM selumetinib significantly decreased CEACAM1 expression levels on cells having W.T. B-Raf but mutated N-Ras (sk-mel-2), 1 µM vemurafenib had no effect on CEACAM1 expression levels. These results further support the regulation of CEACAM1 via the constitutively activated MAPK pathway, which is driven in this case by mutated N-Ras, and not by mutated B-Raf.

C. Inhibitor-resistant cancer cells show increase in CEACAM1 expression and restored activity of MAPK pathway. Two vemurafenib-sensitive B-Raf V600E cell samples (526mel, 624mel) and vemurafenib-resistant cell lines derived therefrom were incubated for 2 days with 1 µM vemurafenib. Cells were then analyzed for CEACAM1 protein expression by FACS as described above. Vemurafenib-resistant cell lines were generated by gradual increase of the inhibitor's concentration in culture, up to 0.32 µM. It was demonstrated that vemurafenib-resistant cell lines expressed higher levels of CEACAM1 than vemurafenib-sensitive cell lines. MAPK activity was measured in vemurafenib-sensitive and vemurafenib-resistant B-Raf V600E (624mel) cell samples by immunoblotting for phosphorylated ERK1/2 (pERK, Thr202/Tyr204), total ERK1/2 and actin after 24 hours of exposure to 160 nM vemurafenib. In vemurafenib-sensitive B-Raf V600E cells vemurafenib almost completely abolishes the phosphorylation of ERK1/2, wherein MAPK activity was practically uninterrupted by vemurafenib in vemurafenib-resistant B-Raf V600E cells.

D. Inhibitor-resistant cancer cells upregulate CEACAM1 expression. B-Raf V600E 526mel melanoma cells were cultured in the presence of 1 µM vemurafenib. Cultivation was performed in RPMI 1640 supplemented with 1 mM Na-Pyruvate, 1 mM Pen-Strep, 1 mM L-Glutamine, 1 mM non-essential amino acids, and 10% heat inactivated fetal calf serum. Initial vemurafenib concentration was 0.01 of the determined $IC_{50}$ (0.64 nM). Each week, the concentration was doubled up to 5 times the $IC_{50}$ (320 nM), to generate vemurafenib-resistant melanoma cells. Cells were then tested for CEACAM1 expression using MRG1 (murine antibody to human CEACAM1) in flow cytometry as described above. Total RNA was extracted with TRIZOL and cDNA was generated with a reverse transcriptase, according to routine protocols. While vemurafenib down regulates CEACAM1 expression in B-Raf V600E melanoma cells, these cells upregulate CEACAM1 expression levels upon acquiring resistance to vemurafenib. It is important to note that CEACAM1 levels in B-Raf V600E melanoma cells after acquiring resistance to vemurafenib are higher than CEACAM1 levels in untreated (vemurafenib-naïve) B-Raf V600E melanoma cells.

E. Inhibitor-resistant cancer cells upregulate expression of both types of CEACAM1. The vemurafenib-sensitive and vemurafenib-resistant B-Raf V600E 526mel melanoma cells mentioned above were tested for the type of CEACAM1 over-expressed upon acquiring resistance to vemurafenib by qPCR. The data presented in FIGS. 12A and 12B demonstrates that the expression of both types of CEACAM1, CEACAM1-long (12A) and CEACAM1-short (12B) is about three-fold upregulated in vemurafenib-resistant cells compared to vemurafenib-sensitive cells.

F. B-Raf/MEK inhibitors increase T-cell induced cytotoxicity. Two vemurafenib-sensitive B-Raf V600E cell samples (526mel, 624mel) were tested for viability in the presence of cytotoxic T cells, with or without 1 µM vemurafenib. Melanoma cells were pre-incubated with 1 µM vemurafenib and then co-incubated overnight with HLA-A2 matched antigen-matched T cells in effector-target ratio of 5:1. Cell killing was determined by LDH release. It was demonstrated that vemurafenib significantly sensitizes melanoma cells to cytotoxic T cells. B-Raf/MEK inhibitors and antibodies to CEACAM1 increase T-cell induced cytotoxicity to cancer cells in-vitro.

Example 6. The Anti-Cancer Effect of CM-24 at Different Doses In-Vivo

SCID-NOD mice were engrafted IV with $5\times10^6$ melanoma cells (cell line MEL526) and were treated for 44 days according to the treatment groups indicated in FIG. 13. Antibodies were given twice a week by IV injection and $10\times10^6$ TIL were administered IV every 10 days. At day 49 the mice were sacrificed and the lungs were removed, photographed (FIG. 13A), weighed (FIG. 13B) and the lesions were counted (FIG. 13C). FIG. 13A—Digital photos of the mice lungs immediately after harvest. FIG. 13B—Tumor weight was calculated by subtracting the lung weight of the naïve mice from the average lung weight of the different treatment groups. The results represent the average of tumor weight±SE from 7-8 mice per treatment group. FIG. 13C—The number of lung lesions in individual mice in the various groups; the black lines represent group medians; lungs with uncountable lesions were scored as 100. Paired T test was used to calculate statistical significance between the groups *P<0.05, **P<0.025.

Treatment with CM-24 in the presence of TIL resulted in robust tumor growth inhibition as can be appreciated by lung morphology (FIG. 13A), tumors' weight (FIG. 13B) and the number of the lung lesions (FIG. 13C), while mice treated with an IgG control showed massive tumor burden and numerous lung melanoma lesions. Only moderate tumor growth inhibition (TGI 47%) was observed in the group administrated with human reactive T cells against melanoma with a control antibody (TIL+IgG), but when CM-24 was added a substantial and dose dependent anti-cancer activity in all doses examined was demonstrated (TGI of 84%, 87%, 90% and 93% in doses of 1, 3, 6 and 10 mg/kg respectively) with statistical significance in the 6 and 10 mg/kg doses (FIG. 13B). Digital photo recordings of the lungs at the assay termination day (FIG. 13A) showed nearly normal lung morphology in mice treated with CM-24 in the presence of TIL, thus indicating that CM-24 in the presence of TIL eliminates almost completely the malignant cells.

In the group administered with TIL and the IgG control some anti-tumor effect was also observed, as was expected. However, when comparing the effect to the CM-24 treated mice in terms of TGI, number of lung lesions and lung morphology, considerable differences were observed.

Evaluation of the number of lung lesions revealed very low numbers of lung lesions in all mice treated with TIL and the various doses of CM-24 and none of these lungs showed more than 10 lesions. On the other hand, in the IgG or TIL+IgG groups several animals showed high number of lesions (>100) and the groups medians were considerably higher than the CM-24 treated mice (FIG. 13C) (100 and 45 in the IgG and TIL+IgG groups compared to 5, 6, 3 and 2, in the CM-24 treated groups; P<0.025).

These effects were observed at concentrations as low as 1 mg/ml but were statistically significant in terms of lung weight at CM-24 concentrations of 6 and 10 mg/kg.
Special notes: 1 mouse from the IgG group showed severe morbidity including limb paralysis and was sacrificed on day 33 (massive tumor burden in the lung was detected); 1 mouse from the TIL+IgG group showed morbidity signs and died on day 49, assay termination day (several lesions were detected); 1 mouse from the TIL+CM-24 group showed severe morbidity and reduced body weight and was sacrificed on day 39 (no evidence of lesions was detected); 3 mice from PBS group showed severe morbidity during the experiment and were sacrificed on day 42 and the other two mice on day 48 (massive tumor burden including high number of lesions in the lung were detected in all mice).

At termination day, a flow cytometry based assay in combination with a QuantiBrite KIT was used in order to determine CEACAM1 receptor occupancy by CM-24 in human TIL isolated from the lungs of the treated mice. Receptor occupancy (RO) values in mice treated with the various CM-24 doses demonstrated (FIG. 14) that RO of 50% could be attributed to concentrations of 1 mg/kg (CM-24 serum level in the blood) and >90% RO was demonstrated in doses of 3, 6 and 10 mg/kg (CM-24 serum levels 0.3, 48.5 and 111 µg/ml, respectively). Examination of CEACAM1 RO values was performed using a flow cytometry based assay using PE conjugated CM-24 antibody and a QuantiBrite Kit (BD) Results represent average±SE of RO values on TIL isolated from the lung of 8-9 mice per treatment group. Data was analyzed using Kaluza software.

From the data above it is clear that substantial tumor growth inhibition was observed in mice treated with CM-24 in the presence of TIL, leading to almost complete elimination of the malignant cells. Although all CM-24 doses demonstrated effective anti-cancer responses, the increasing doses showed correlation to higher values of tumor growth inhibition (TGI of 84, 87, 90 and 93 corresponding to doses of 1, 3, 6 and 10 mg/kg respectively), which were also statistically significant. Ex vivo RO results demonstrate an RO>90% in doses of 3, 6 and 10 mg/kg (CM-24 serum levels 0.3, 48.5 and 111 µg/ml respectively) while RO of 50% was detected in the 1 mg/kg dose. When evaluating the RO data from mice treated with CM-24 at a dose of 1 mg/kg, although CM-24 serum concentrations are very low, the RO data demonstrates that CM-24 is still bound to the TIL in the lungs, implying that CM-24 can mediate a long lasting effect in vivo in the tumor microenvironment.

These results support the mode of action of CM-24 as an enhancer of the cytotoxic activity of the effector cells against malignant cells and show that CM-24 is a potent anti-cancer agent.

Example 7. Summary of Pre-Clinical Data

CM-24 is a humanized IgG4 anti human CEACAM1 monoclonal antibody that binds the N terminal domain of CEACAM1 and blocks intercellular CEACAM1 interaction between activated lymphocytes and tumor cells; blockade of CEACAM1 interactions by CM-24 is therefore proposed to enhance the killing activity of lymphocytes and is a promising avenue to pursue for immunotherapy of cancer.

CM-24 shows high affinity and selective binding to human CEACAM1, which is expressed by activated lymphocytes or tumor cells. Data in in vitro immuno-modulatory models demonstrated that CM-24 is a potent blocker of intercellular CEACAM1-CEACAM1 interactions and can enhance the cytotoxic killing of various human CEACAM1-positive tumor cells by CEACAM1-positive NK and lymphokine-activated killer (LAK) cells and tumor infiltrating lymphocytes (TIL). The enhanced killing activity induced by CM-24 may be mediated by granzyme B and IFNγ secretion as demonstrated in various models.

CM-24 enhances the cytotoxic activity of effector cells in the presence of CEACAM1 positive tumor cells and in the context of a specific human leukocyte antigen (HLA)-restricted T cell reaction. CM-24 does not enhance the cytotoxic activity of effector lymphocytes against CEACAM1 positive non-target cells (human normal cells). In addition, the data shows that CM-24 does not have ligand-like agonistic effects, Fc-related effector functions or direct effects. Binding of CM-24 to CEACAM1 does not induce agonistic activity, and no effect of CM-24 on effector cells could be observed in the absence of target cells as demonstrated in in vitro functional assays. CM-24 is also not expected to induce antibody-dependent cell-mediated cytotoxicity (ADCC) or complement-dependent cytotoxicity (CDC) because it is an IgG4 is unable to bind the complement component—C1q and the ADCC mediator—Fcγ-RIIIa and has no direct effect on the proliferation rate or viability of CEACAM1-positive primary cells (lymphocytes, epithelial and endothelial cells).

Various in vivo tumor xenograft models demonstrate that CM-24 has clear anti-cancer activity, which is accompanied by an increase in immunological activity of T cells within the tumor.

CEACAM1 blockade would alleviate CEACAM1-mediated inhibition of CEACAM1-positive tumor-infiltrating lymphocytes encountering CEACAM1-positive cancer cells within the tumor microenvironment. The immunological effect is expected to be enhancement of the local immune response against tumor cells, which is expected to result in their elimination and subsequent clinical regression.

Pre-clinical evaluation of the safety of CM-24 included assessment of the effect of CM-24 on T cell proliferation and pro-inflammatory cytokine secretion. Human peripheral blood mononuclear cells (PBMCs) and whole blood from 10 healthy donors were evaluated and the antibody was presented by both soluble and immobilized form. There was no apparent CM-24-induced proliferation and no significant pro-inflammatory cytokine secretion in soluble or dry-coated immobilized stimulation formats.

A 6 week repeat dose study was performed in rhesus monkeys to evaluate the toxicity and toxicokinetics of CM-24. CM-24 was administered via intravenous (IV) infusion (the intended clinical route of administration) once every two weeks for a total of 4 doses (mimicking the intended treatment cycle in oncology patients) at doses representing 2.5× (25 mg/kg) and 10× (100 mg/kg) the projected maximal dose in humans (10 mg/kg). No obvious treatment related adverse reactions, no gross or microscopic pathological findings, and no mortality were observed. Ophthalmoscopy and electrocardiography indicated no findings related to the treatment. In addition, all blood and urine tests were found to be within normal ranges for Rhesus monkeys. Taken together, the pivotal GLP repeat-dose toxicology study in Rhesus monkeys showed no treatment-related toxicities at any dose level, and the No Observed Effect Level (NOEL) was determined to be 100 mg/kg. The toxicokinetics evaluation showed a dose-proportional increase in CM-24 exposure (Cmax, AUC) when administered by IV infusion. A slight increase in Cmax and AUC on Day 42 as compared to Day 0 might suggest the potential for some CM-24 accumulation when the mAb is administered by this ROA and dosing regimen at these dose levels. Only a single animal in Group 2 (25 mg/kg) showed a positive anti-CM-24 antibody response, suggesting that ADA response most likely had no effect on either pharmacokinetics or toxicity study. This result does not represent a strong immunogenicity response to repeated dosing with CM-24 results.

The safe clinical starting dose for CM-24 based on the MABEL determined from the in vivo experiments in the mouse tumor xenograft models results is in the range of 0.2-1 mg/kg, comprising a 10 fold safety factor. The pivotal GLP repeat-dose toxicology study in Rhesus monkeys showed no treatment-related toxicities at any dose level, and the No Observed Effect Level (NOEL) was determined to be 100 mg/kg (human equivalent dose (HED) of 100 mg/kg on a weight-to-weight basis), which clearly supports the range determined by the MABEL evaluation. The results of the in vitro/ex vivo PBMC proliferation and pro-inflammatory cytokine production assay demonstrated no substantial CM-24 related induction of T cell proliferation and pro-inflammatory cytokine production.

Example 8. A Phase 1, Open-Label, Multicenter, Multi-Dose Escalation Study of CM-24 in Subjects with Selected Advanced or Recurrent Malignancies Six tumor types—melanoma, non-small cell lung cancer adenocarcinoma, gastric, colorectal, bladder and ovarian cancer—have been selected for the current study, as they are representative of tumors for which a high medical need for new therapies exist; those for which there is a precedent for clinical responses to other immunotherapies; and those for which there is supportive correlative pathologic data suggesting that the CEACAM1 pathway is important for tumor progression.

The study includes 2 phases: The Dose Escalation Portion and the Expansion Cohort Portion. The Dose Escalation Portion last at least 12 weeks beginning with 4 infusions (Cycle 1) for each subject. Subjects with no Dose Limiting Toxicity (DLT) and who show evidence of clinical benefit (Complete response—CR, Partial Response—PR, Stable Disease—SD) as well as subjects with Progressive Disease—PRD on imaging assessment who are otherwise clinically stable are treated for up to a total of 5 additional cycles (Continued Treatment Period) that last up to an additional 38 treatment weeks and at least 25 weeks of follow up (total 75 weeks/approx. 15 months). The Expansion Portion last up to 46 treatment weeks and at least 25 weeks of follow up (total 71 weeks/approx. 14 months) in cutaneous melanoma subjects.

Primary Objectives:
1. Assess the safety and tolerability of escalating multiple doses of CM-24 (administered intravenously) and
2. Determine the recommended Phase 2 dose of CM-24, in subjects with advanced or recurrent malignancies including melanoma, non-small cell lung adenocarcinoma, and gastric, colorectal, bladder and ovarian cancers.

Secondary Objectives Include:
1. Characterize the pharmacokinetic profile of multiple doses of CM-24.
2. Characterize the immunogenicity of CM-24.
3. Evaluate preliminary efficacy on the basis of objective tumor response and duration of response in subjects treated with CM-24.

Explorative Objectives Include:
1. Explore a potential predictive biomarker associated with CM-24 clinical activity based on levels of expression of CEACAM1 in tumor specimens prior to treatment.
2. Investigate the immuno-modulatory activity of CM-24 on selected immune cell populations and soluble factors in tumors and peripheral blood.
3. Assess the overall survival in subjects treated with CM-24.

The Dose Escalation Portion:
Study drug dosing is scheduled to be administered in a staggered manner starting with 0.01 mg/kg, and continuing to 0.03 mg/kg, 0.1 mg/kg, 0.3 mg/kg, 1 mg/kg, 3 mg/kg, and 10 mg/kg. Subjects will be assigned to a dose level in the order of study entry. For the first two dose levels (0.01 mg/kg and 0.03 mg/kg) 1 patient in each cohort is enrolled in an accelerated design in which a single grade 2 drug related toxicity results in expansion to a 3+3 design at the dose and all subsequent doses. For subjects in the lower two cohorts (0.01 mg/kg and 0.03 mg/kg) Dose escalation from the first single patient low dose cohort (0.01 mg/kg) to the next cohort (0.03 mg/kg), and from the second single dose cohort (0.03 mg/kg) to the next cohort (0.1 mg/kg) commence after a 6 week DLT window, if no Grade 2 or greater toxicity has occurred. For dose levels of 0.1 mg/kg and above, at least 3 patients per cohort are enrolled in a standard 3+3 design unless a DLT occurs, in which case the cohort is expanded to 6 patients. Escalation to the next cohort only commence after an 8 week DLT window, beginning from the first study drug administration of the first subject of each cohort.

The Dosing Period includes three periods: Screening, Dosing and Follow-up: 1) 4 repeat doses that comprise the first Cycle followed by a 6 week observation period), 2) a Continued Treatment Period (cycles 2-6) and 3), a Follow-Up Period including assessment of overall survival. Each treatment Cycle comprises of 4 doses of study drug administration every 2 weeks. At least 3 subjects per cohort are enrolled in a standard 3+3 design. The minimum planned number of subjects enrolled in this portion is 17 but can increase if Dose Limiting Toxicities (DLTs) occur. If a DLT occurs at a given dose level, this dose level is expanded to 6 subjects, thus the maximum number of subjects in the Dose Escalation Portion is 42.

Enrolled subjects receive 4 treatments, once every 2 weeks (Cycle 1) followed by a 6 week Observation Window; when appropriate subjects enter Continued Treatment period during which they receive additional Cycles (2-6). During this Continued Treatment Period, subjects undergo clinical and laboratory assessments including physical examination (body weight, vital signs and oxygen saturation), pharmacokinetics and pharmacodynamics, cytokine collection as well as safety laboratory testing and immune safety assays and ECG is being recorded. All subjects undergo response evaluation one week and five weeks following Cycle 1, based on imaging and clinical assessments. Once eligible to continue in the study, additional response evaluations is performed immediately before the beginning of the next cycle. After the last continued treatment cycle, subjects are followed for safety, efficacy and survival.

The Expansion Portion:

Up to 20 metastatic cutaneous melanoma subjects are enrolled and treated at the recommended Phase 2 dose (RP2D). It includes 3 periods: Screening, Dosing and Follow-Up. The Dosing Period consists of 6 cycles of 4 treatments each administered every 2 weeks. The Follow-Up Period includes assessing overall survival.

Enrolled subjects receive the recommended Phase 2 dose every 2 weeks in each cycle. Four treatments are administered and the subjects continue treatment up to 6 cycles. During the Dosing Period, subjects undergo clinical and laboratory assessments as detailed above.

Subjects must have a "wash out" period of at least 4 weeks prior to first study drug administration from all previous chemotherapy and experimental agents except for immuno-modulators (for example, but not limited to: anti-CTLA4, anti-PD-L1, anti-PD-1 antibodies, IL-2) which must have a "wash out" period of at least 6 weeks prior to first study drug administration, and all adverse events have either returned to baseline or stabilized at Grade 1 or less.

Melanoma subjects with B-Raf V600E or V600K mutation-positive melanoma must have progressed on, or were intolerant to, prior B-Raf- and/or MEK-inhibitor therapy.

Dose Escalation Portion

Cycle 1 will consist of a 6-week Repeat Dosing Period (4 doses, each 2 weeks apart); and a 6-week observation period.

A minimum of 1 week must elapse between the first treatment of any subject in a dose cohort and the first treatment for the subsequent subject in that dose cohort.

Subjects are followed closely during the 12-week Initial Study Period. All subjects undergo response evaluation one week and five weeks after the end of Cycle 1 for evidence and confirmation of clinical benefit, defined as stable disease (SD), partial response (PR) or complete response (CR) by Week 12. Subjects with evidence of Progressive Disease (PRD) on either Week 7 or 11 imaging after being reconsented on the Informed Consent Form (ICF), can continue study participation and continued CM-24 treatment, if investigator deems it is clinically warranted according to Stopping Rules of Clinical Deterioration Section and further evaluated at week 15. If follow-up imaging at Week 15 confirms PRD, the subject does not continue treatment due to confirmed disease progression.

All subjects with DLTs, including delayed DLTs, will discontinue further dosing with CM-24 but are not withdrawn from the study.

Subjects who are withdrawn from the study before completion of the first 3 study drug administrations in the Initial Study Period (Cycle 1) are replaced. Subjects who are withdrawn for any other reason other than withdrawal of consent are followed over 4 follow-up visits for a period of six months.

Cycles 2-6 are referred to as the Continued Treatment Period. Following the Initial Study Period, subjects with evidence of clinical benefit, defined as SD, PR or CR according to modified RECIST 1.1 criteria and no evidence of Dose Limiting Toxicity (DLT) by Week 12, may continue treatment with CM-24 at the same dose level received during the Initial Study Period for 5 additional treatment cycles. Subjects with PRD that has been confirmed but is not worsening and with otherwise stable or improved clinical status should continue to be treated with study drug until there is further progression or clinical deterioration.

Each full treatment cycle of the Continued Treatment Period comprises 4 doses of study drug administered 2 weeks apart, on Days 1, 15, 29, and 43. A response assessment is performed between Days 52 and 56 of each treatment cycle. The response assessment must be completed before the first dose of the next cycle is administered.

During the Continued Treatment Period, subjects with PRD that has been confirmed but is not worsening and with otherwise stable or improved clinical status should continue to be treated with study drug until there is further progression or clinical deterioration.

After the last administration of CM-24 in the Continued Treatment Period, each subject is followed over 4 follow-up visits for a period of six months.

All subjects with DLTs, including delayed DLTs, discontinue further dosing with CM-24 but are not withdrawn from the study.

All subjects are followed indefinitely for survival.

Cohort Expansion

For the first two dose levels (0.01 mg/kg and 0.03 mg/kg) 1 patient in each cohort is enrolled in an accelerated design in which a single grade 2 drug related toxicity results in expansion to a 3+3 design at the dose and all subsequent doses. For subjects in the lower two cohorts (0.01 mg/kg and 0.03 mg/kg) Dose escalation from the first single patient low dose cohort (0.01 mg/kg) to the next cohort (0.03 mg/kg), and from the second single dose cohort (0.03 mg/kg) to the next cohort (0.1 mg/kg) are commence after a 6 week DLT window, if no Grade 2 or greater toxicity has occurred. For dose levels of 0.1 mg/kg and above, at least 3 patients per cohort will be enrolled in a standard 3+3 design unless a DLT occurs, in which case the cohort is expanded to 6 patients. Escalation to the next cohort will only commence after an 8 week DLT window, beginning from the first study drug administration of the first subject of each cohort.

If no additional subject in the 6-subject cohort has a DLT, then following review of safety data for all subjects by the Safety Committee, dose escalation may proceed.

If 2 or more subjects in a 3- or 6-subject dose cohort develop DLTs, dose escalation is stopped, and:

If the preceding dose level cohort was not already been expanded to 6 subjects, it will be expanded to 6 subjects.

If the previous dose level cohort was already expanded to 6 subjects, the Safety Committee, after review of all safety data to date, may:

Deem the (previous) dose level to be the recommend Phase 2 dose (RP2D), or

Recommend evaluation of a new cohort at an intermediate dose.

The recommended Phase 2 dose (RP2D) is defined as the highest dose level at which no more than 1 out of 6 subjects experiences a DLT.

Dose Escalation

If no DLTs are encountered in the 6 week DLT window for lower two cohorts, and for remaining cohorts, an 8 week DLT window, then the next cohort is started and the same pattern repeated. There is a one-week waiting period between subject enrollments within each cohort dose level. Prior to dose escalation the available safety data for all subjects treated in the study to date, including the current cohort, are evaluated by the Safety Committee.

The dosing (cycle 1) of the next dose cohort is initiated only after the repeat dosing (cycle 1) for all subjects in the preceding dose cohort has been completed. The timing of the Safety Committee review is based upon data suggesting that irAEs in patients treated with other immuno-modulators occur within 5-10 weeks following administration. Should a DLT occur, necessitating expansion of the treatment dose cohort to six subjects, the DLT window is expanded to encompass full repeat dosing (Cycle 1) of all six subjects.

If, after the dose is escalated, if 2 or more delayed DLT's are encountered at a lower dose, and that AE could be a possible delayed DLT related to CM-24, accrual is temporarily suspended and the Safety Committee notified within 24 hours. The Safety Committee will promptly evaluate the event and relevant information, including PK data, and makes any necessary adjustment in dose and/or the dose escalation scheme. The same steps are to be undertaken 2 or more delayed DLT's occur in a previously tested, 6-subject expanded cohort.

Delayed DLTs will be reviewed by the Safety Committee following guidelines and decisions are made on a case-by-case basis. Such actions could include applying the standard DLT escalation rules, returning to a lower or intermediate dose, or taking no action if the dose-related event being examined is not serious enough to halt dose escalation and current dosing is not considered a risk to subjects.

Expansion Portion

The Expansion Portion of this study allows enrollment of up to 20 subjects with advanced cutaneous melanoma. Other expansion arms of up to 20 subjects may be opened, subject to protocol amendment, in the indications previously studied during the Dose Escalation Portion of the trial, if early efficacy signals warrant this. Enrolled subjects are treated at the RP2D for up to six cycles, with treatment administered on Days 1, 15, 29, and 43. A response assessment is performed between Days 52 and 56. The response assessment must be completed before the first dose administration in the next cycle.

Enrolment may be held in the Expansion Portion if the rate of DLTs is ≥33%. Subjects who are tolerating study drug are not automatically precluded from continued dosing until the Safety Committee review, and are allowed to continue dosing for as long as tolerated unless directed otherwise as a result of the safety review. After safety analysis, a decision is made whether to resume enrolment and continue dosing at the current dose or continue enrolment of further subjects at a lower dose. For DLTs, enrolment is held and/or restarted following review of the Safety Committee.

Treatment Decision Guidelines

Tumor response is evaluated using Response Evaluation Criteria in Solid Tumors (RECIST 1.1). End of cycle tumor response assessments for all subjects occur within Days 52 to 56 of each treatment cycle (results of assessments must be reviewed and documented before the first dose of the next cycle). Following each (continued or expansion) treatment cycle, the decision to treat a subject with an additional cycle of CM-24 is based on tumor assessment, unless the subject develops a ≥Grade 3 (CTCAE) adverse event or other adverse event related to CM-24 that precludes further treatment. Subjects are treated until confirmed complete response (CR) or progressive disease (PRD) that is both confirmed and then further progresses as described below. Subjects with PRD that has been confirmed but is not worsening and with otherwise stable or improved clinical status (i.e. no reduction in ECOG performance status) should continue to be treated with study drug until there is further progression or clinical deterioration, as further elaborated below.

Subjects with a Best Overall Response (BOR) of CR, PR or SD continue to receive CM-24 treatment until the first occurrence of either:
Achievement of a confirmed CR;
Clinical deterioration suggesting that no further benefit from treatment is likely;
Meets criteria for discontinuation of study therapy (DLT) or other intolerability to therapy; or
Receipt of the maximum number of cycles.

Follow-Up Period

Subjects are followed for a period of at least six months beginning from the last treatment infusion. The $1^{st}$ follow-up visit will take place within 7 days of the last imaging scan. Follow-up visits 2-4 will take place at 56 day intervals. In addition, survival status is assessed approximately every 3 months, indefinitely, by either a telephone call or in-person contact, following completion or discontinuation of the treatment, and follow-up of the study. Dates of death are reported for any subjects that are deceased. Overall survival assessments are made until study completion or termination by the Sponsor. No other data (e.g., subsequent therapies, performance status etc.) other than survival is collected during these calls or visits.

When a subject discontinues study drug treatment, the date and reason for study drug discontinuation should be documented in the source documents, and the subject should enter the Follow-up Period. When a subject withdraws from the study (during the Treatment or Follow-up Period), all efforts should be made in order to ensure that all evaluations associated with that study visit are performed and the date and reason for study discontinuation are documented in the source documents.

Following completion of the treatment and follow-up periods, all surviving subjects are followed for survival status every 3 months, indefinitely.

Physical Description of Study Drug

CM-24 is supplied in a single-use 10 mL vial. Each vial contains a concentrated solution with the equivalent of 100 mg CM-24 (10 mg/mL).

CM-24 is administered as an intravenous infusion, with a 0.2 micron in-line filter at the protocol-specified doses.

Instructions for Preparation of the Different Doses:

For subjects receiving doses of 0.1 mg/kg, 0.3 mg/kg and 1.0 mg/kg, a 50 mL 0.9% sodium chloride IV bag is used for the preparation. Infusion should proceed at a rate of 1.0 mL/minute. Rounding during dose preparation should be performed only when absolutely necessary and should only be done in a manner that will allow the minimum concentration of 0.25 mg/mL to be maintained.

For subjects receiving dose of 3 mg/kg, a 100 mL 0.9% sodium chloride IV bag is used for the preparation. Infusion should proceed at a rate of 2.0 mL/minute. Rounding during dose preparation should be performed only when absolutely necessary.

For subjects receiving dose of 10 mg/kg, a 250 mL 0.9% sodium chloride IV bag is used for the preparation. Infusion should proceed at a rate of 3.0 mL/minute. Rounding during dose preparation should be performed only when absolutely necessary.

Pharmacodynamic (PD) Markers

Blood samples are taken and tested for immune assays and other evaluations at the following time points: pre-dose of 1st study drug administration, 48 hours after the 1st and 4th dose of Cycle 1 study drug administration, and pre-dose of 4th (last) dose of each complete cycle (cycles 2-6 of dose escalation, and all cycles of the expansion cohort), Follow-up Visits 2-4, and include:

- lymphocyte subtypes (CD4, CD8 and CD56) in combination with activation markers (CD69, CD107a and HLA-DR), Regulatory T cells by fluorescence-activated cell sorting (FACS)
- CEACAM1 expression in lymphocyte subtypes
- soluble CEACAM1 and Granzyme B in serum
- percent CEACAM1 receptor occupancy by CM-24
- myeloid derived suppressor cells (MDSCs) (CD14+, HLADR low, CD11b+) immune checkpoint proteins, for example PD-1, TIM-3, LAG, Vista Pharmacokinetics (PK)

Pharmacokinetics is initially studied during the Dose Escalation Portion during the first infusion (first dose of Cycle 1) and during the fourth infusions (last dose of Cycle 1). Pre-dose levels are also taken before each treatment in the 1st cycle. Additional Dose Expansion subjects (up to 6) may be tested for PK evaluation at the preliminary RP2D if more robust PK characterization of CM-24 is deemed warranted.

The PK profile of CM-24 is assessed in plasma up to 15 days post dose for the first dose and 36 days post-infusion for the fourth dose. The following PK parameters are derived from the plasma concentration versus time profiles: $C_{max}$, $t_{1/2}$, $T_{max}$, $AUC_{0-t}$, and $AUC_{0-28}$.

Samples are taken at the first and fourth infusions at the following time points: pre-infusion (baseline); at the end of the infusion and at 1, 4, 8, 24 hours post-infusion. For the 1st and 4th doses only: on Days 3, 5, 8, 15 (or pre-dose of next treatment) and for the 4th dose also on 22 and 36 days post infusion. Pre-dose levels will be taken before each treatment in the 1st cycle. Refer to the Schedule of Events and the Laboratory Manual for further information on sample collection and shipment of samples.

Fresh Tumor Biopsies

Tumor samples are evaluated for the following: CD4, CD8, CD56, FOXp3, CEACAM1, Granzyme B, CM-24, % CEACAM1 receptor occupancy by CM-24.

Dose Escalation Portion:

Subjects are asked to provide an optional fresh biopsy tissue (or archived if taken within the past six months) sample at baseline and a week after the second treatment of the 1st cycle.

Expansion Portion:

Two fresh tumor samples are taken, at Screening and one week after the 2nd dosing administration of the 1st cycle. In addition, subjects are encouraged but not required to provide one additional biopsy a week after the fourth treatments of the Pt cycle.

Efficacy Endpoints

The following endpoints are used to assess preliminary efficacy, and are derived from the modified RECIST 1.1 criteria:

- Objective Response Rate (ORR)
- Duration of Response (DOR)
- Tumor Response Status
- Disease Control Rate (DCR)
- Durable Response (DR)
- Best Overall Response (BOR)—Complete Response (CR), Partial Response (PR), Stable Disease (SD) and Progressive Disease (PRD).
- Progression Free Survival (PFS)
- Time to Response (TTR)
- Overall Survival (OS)
- Percent Change in Tumor Burden (PCTB), assessed by CT or MRI.

The listed above efficacy endpoint will be evaluated at:

Dose Escalation Cohorts:

Week 7, one week after the fourth dose of the first cycle was administered.

Week 11, five weeks after the fourth dose of the first cycle was administered

Week 18-19, Week 26-27, Week 34-35, Week 42-43, Week 48-49 and

Week 50-51, after the five additional cycles, plus follow-up visits 2-4.

Dose Expansion Cohort:

Week 7-8, Week 14-15, Week 22-23, Week 30-31, Week 38-39, Week 46-47, plus follow-up visits 2-4.

Immune-Related Efficacy Endpoints

Additional exploratory efficacy evaluations may include the application of an immune-related response criteria (irRC) based on modifications to the RECIST 1.1 (referred to as irRECIST) and include the following endpoints.

Immune-related best overall response (irBOR) with response categories irCR, irPR, irSD, irPD;

Immune-related objective response rate (irORR) during the entire study period;

Duration of ir responses (DOirR) for those subjects with ir-responses;

The irORR based on the irBOR outcomes in any number of cycles may also be derived.

Pharmacokinetic (PK) Endpoints

Pharmacokinetic is studied during the Dose Escalation Portion during the following PK time points: Samples will be taken at the first, and fourth infusions at the following time points: pre-infusion (baseline); at the end of the infusion and at 1, 4, 8, 24 hours post-infusion. For the 1st and 4th doses: on Days 3, 5, 8, 15 (pre-dose of next treatment) and for the 4th dose also at, 22 and 36 days post infusion. Pre-dose levels are taken before each treatment in the 1st cycle.

Additional Dose Expansion subjects (up to 6) may be tested for PK evaluation at the preliminary RP2D if more robust PK characterization of CM-24 is deemed warranted.

Example 7. Formulation

An exemplary formulation of a humanized mAb according to the present invention comprises the following:

| Concentration (mg/ml) | Ingredient |
| --- | --- |
| 10.00 | CM-24 Drug Substance |
| 4.65 | L-Histidine |
| 82.00 | Sucrose |
| 0.20 | Polysorbate 20 |

The invention claimed is:

1. A humanized monoclonal antibody (mAb) or a fragment thereof, which specifically recognizes CEACAM1, comprising:
   i. a heavy chain variable region sequence selected from the group consisting of: SEQ ID NO:28, SEQ ID NO:29, SEQ ID NO:30, SEQ ID NO:31 and SEQ ID NO:32, and
   ii. a light chain variable region sequence selected from the group consisting of: SEQ ID NO:33, SEQ ID NO:34 or SEQ ID NO:35.

2. The humanized mAb of claim 1, comprising the heavy chain variable region sequence set forth in SEQ ID NO:32, and the light chain variable region sequence set forth in SEQ ID NO:34.

3. The humanized mAb according to claim 1, comprising a heavy chain sequence selected from the sequence set forth in SEQ ID NO:53 and the sequence set forth in SEQ ID NO:59 and a light chain set forth in SEQ ID NO: 52.

4. The humanized mAb according to claim 1, comprising a light chain set forth in SEQ ID NO: 52, and a heavy chain set forth in SEQ ID NO: 53.

5. A method of attenuating or treating a disease or disorder associated with expression, activation or function of a CEACAM1 protein, comprising administering to a subject in need thereof a therapeutically effective amount of the humanized monoclonal antibody or fragment thereof of claim 1.

6. The method of claim 5, wherein the disease or disorder is a cancer.

7. The method of claim 6, wherein the cancer is selected from the group consisting of: melanoma, colorectal, bladder, lung, non-small cell lung carcinoma (NSCLC), non-small cell lung adenocarcinoma (NSCLA), gastrointestinal, pancreatic, breast, prostate, thyroid, stomach, ovarian, myeloma and uterine cancer.

8. The method of claim 5, further comprising administering to the subject lymphocyte cells, a lymphocyte activating agent, or an additional anti-cancer composition.

9. The method of claim 5, comprising administering to the subject at least one dose of the humanized mAb to CEACAM1 ranging from 0.01 mg/kg to 10 mg/kg body weight.

10. The method of claim 9, comprising administering
(i) multiple, identical or different, doses of the humanized mAb;
(ii) multiple escalating doses; or
(iii) the humanized monoclonal antibody or fragment thereof once every week, one every 2 weeks, once every 3 weeks, once every 4 weeks, or once every 5 weeks.

11. The method of claim 10, comprising 1-10 administration cycles, each cycle comprising 2-5 infusions every 1-4 weeks, with the humanized mAb, followed by a 2-8 weeks between each cycle.

12. A method of immunomodulation, the method comprising contacting a CEACAM1-expressing lymphocyte with the humanized monoclonal antibody or fragment thereof of claim 1.

13. A method of inhibiting CEACAM1 homotypic or heterotypic protein-protein interaction, the method comprising contacting a CEACAM1-expressing lymphocyte with the humanized monoclonal antibody or fragment thereof of claim 1, which specifically recognizes human CEACAM1, thereby inhibiting CEACAM1 homotypic or heterotypic protein-protein interaction.

14. A method for detecting a cancer in a subject, the method comprising: obtaining a biological sample from the subject; contacting the biological sample with a diagnostic composition comprising the humanized monoclonal antibody or fragment thereof of claim 1, detecting whether the subject has cancer by detecting complex formation between the diagnostic composition and CEACAM1 protein beyond a predetermined threshold.

15. A method for measuring expression of CEACAM1 in a biological sample, the method comprising detecting whether CEACAM1 is present in the biological sample by contacting the biological sample with the humanized monoclonal antibody or fragment thereof of claim 1, determining that CEACAM1 is present in the biological sample, and measuring the level of immune complex formation between CEACAM1 and the mAb or a fragment thereof.

16. The method of claim 5, comprising administering to the subject at least one dose of the humanized mAb to CEACAM1 ranging from 10 mg/kg to 50 mg/kg body weight.

* * * * *